(12) United States Patent
Mayall

(10) Patent No.: US 8,398,968 B2
(45) Date of Patent: Mar. 19, 2013

(54) ADENOVIRAL EXPRESSION VECTORS

(75) Inventor: Timothy P. Mayall, Encinitas, CA (US)

(73) Assignee: Canji Inc., Palo Alto, CA (US)

( * ) Notice: Subject to any disclaimer, the term of this patent is extended or adjusted under 35 U.S.C. 154(b) by 269 days.

(21) Appl. No.: 12/410,194

(22) Filed: Mar. 24, 2009

(65) Prior Publication Data

US 2010/0008889 A1 Jan. 14, 2010

Related U.S. Application Data

(63) Continuation of application No. 11/636,902, filed on Dec. 11, 2006, now abandoned.

(60) Provisional application No. 60/750,012, filed on Dec. 12, 2005.

(51) Int. Cl.
*A61K 48/00* (2006.01)
*A61K 35/76* (2006.01)
*C12N 15/00* (2006.01)

(52) U.S. Cl. ............ 424/93.2; 514/44 R; 435/320.1
(58) Field of Classification Search ........... 424/93.2; 514/44 R; 435/320.1
See application file for complete search history.

(56) References Cited

U.S. PATENT DOCUMENTS

| | | | |
|---|---|---|---|
| 5,837,520 A | 11/1998 | Shabram et al. | |
| 5,891,690 A | 4/1999 | Massie | |
| 5,932,210 A | 8/1999 | Gregory et al. | |
| 5,994,134 A | 11/1999 | Giroux et al. | |
| 6,146,891 A | 11/2000 | Condon et al. | |
| 6,165,779 A | 12/2000 | Engler et al. | |
| 6,210,939 B1 * | 4/2001 | Gregory et al. | 435/456 |
| 6,248,514 B1 | 6/2001 | Hutchins et al. | |
| 6,261,823 B1 | 7/2001 | Tang et al. | |
| 6,312,681 B1 | 11/2001 | Engler et al. | |
| 6,392,069 B2 | 5/2002 | Engler et al. | |
| 6,395,519 B1 | 5/2002 | Fallaux et al. | |
| 6,430,595 B1 | 8/2002 | Ferguson et al. | |
| 6,544,769 B1 | 4/2003 | Frei et al. | |
| 6,649,158 B1 | 11/2003 | LaFace | |
| 6,783,983 B1 | 8/2004 | Condon et al. | |
| 6,835,557 B1 | 12/2004 | Weissmann | |
| 7,001,770 B1 | 2/2006 | Atencio et al. | |
| 7,074,618 B2 | 7/2006 | Li et al. | |
| 7,851,218 B2 | 12/2010 | Howe et al. | |
| 2002/0064860 A1 | 5/2002 | Cannon-Carlson et al. | |
| 2002/0150557 A1 | 10/2002 | Ramachandra et al. | |
| 2005/0074885 A1 | 4/2005 | Vogels et al. | |
| 2006/0270041 A1 | 11/2006 | Howe et al. | |

FOREIGN PATENT DOCUMENTS

| | | |
|---|---|---|
| WO | WO 99/41416 | 8/1999 |
| WO | WO 2004/108088 | 12/2004 |
| WO | WO 2005/058368 | 6/2005 |
| WO | WO 2006/065827 | 6/2006 |
| WO | WO 96/27677 | 9/2006 |

OTHER PUBLICATIONS

Carbone et al. Seminars in Cancer Biology, 2004, 14: 399-405.*
Vile et al Gene Therapy, 2000, 7: 2-8.*
Rubanyi et al Molecular Aspects of Medicine, 2001, 22, 113-142.*
Lu et al Cancer Gene Ther. Jan.-Feb. 1999; 6(1): 64-72.*
Kerbel et al Cancer Biology & Therapy, 2003, 2: 4 suppl. 1, S134-139.*
Gura et al Science, 1997, 278: 1041-1042.*
Kelland et al European Journal of Cancer, 2004, 40, 827-836.*
Ecke et al, Goodman & Gilman's The Pharmacological basis of Therapeutics, McGraw-Hill, New York, NY. 1996, pp. 77-101.*
Xu et al Biochim Biophys Acta. Jun. 11, 2003; 1621(3):266-71.*
Dermers et al (Molecular Therapy, 2002, 50-56.*
Benedict et al (Mol Ther. 2004; 10(3): 525-32.*
Ahmad et al (Cancer Gene therapy, 2001, 8, 788-795.*
Pagliaro et al Journal of Clinical Oncology, 2003 15;21(12):2247-53.*
Connor et al 2001, Gene Ther. 8: 41-48.*
Amalfitano et al., "Production and Characterization of Improved Adenovirus Vectors with the E1, E2b, and E3 Genes Deleted", *Journal of Virology* 72(2):926-933 (Feb. 1998).
Appleby et al., "A novel combination of promoter arid enhancers increases transgene expression in vascular smooth muscle cells in vitro and coronary arteries in vivo after adenovirus-mediated gene transfer", *Gene Therapy* 10:1616-1622 (2003).
Aurisicchio et al., "Liver-Specific Alpha 2 Interferon Gene Expression Results in Protection from Induced Hepatitis". *Journal of Virology*,74(10):4816-4823 (May 2000).
Bell et al., "The Protein CTCF Is Required for the Enhancer Blocking Activity of Vertebrate Insulators", *Cell* 98:387-396 (Aug. 6, 1999).
Bell et al., "Insulators and Boundaries: Versatile Regulatory Elements in the Eukaryotic Genome", *Science* 291:447-450 (Jan. 19, 2001).
Benedict at al., "Intravesical Ad-IFN-a Causes Marked Regression of Human Bladder Cancer Growing Orthotopically in Nude Mice and Overcomes Resistance to IFN-a Protein", *Molecular Therapy* 10(3):525-532, (Sep. 2004).
Benoist at al., "In vivo sequence requirements of the SV40 early promoter region", Nature 290:304-310 (Mar. 26, 1981).
Berkner at al., "Expression of dihydrofolate reductase, and of the adjacent Elb region, in an Ad5-ihydrofolat reductase recombinant virus", *Nucleic Acids Research* 12(4):1925-1941 (1984).
Berkner et al., "Generation of adenovirus by transfection of plasmids". *Nucleic Acids Research* 11(17):6003-6020 (1983).
Boschetti, "Advanced sorbents for preparative protein separation purposes", *Journal of Chromatography A* 658:207-236 (1994).

(Continued)

*Primary Examiner* — Anoop Singh

(57) ABSTRACT

The present invention provides a recombinant adenovirus vector characterized by the partial or total deletion of adenoviral E2B function and having an expression cassette containing a heterologous sequence encoding a protein of interest inserted into the E1 region. Such vectors are designed to reduce or eliminate the occurrence of replication competent adenovirus contamination. Additionally, the expression cassette of the vector may contain one or more regulatory elements capable of increasing the expression of the heterologous sequence and/or reducing the expression of viral proteins. Such a reduction in expression of viral proteins reduces the cytotoxicty and immunogenicity of the adenovirus vectors when administered in vivo. Transformed production host cells and a method of producing recombinant proteins and gene therapy also are included within the scope of this invention.

4 Claims, 22 Drawing Sheets

OTHER PUBLICATIONS

Brasset et al., "Insulators are fundamental components of the eukaryotic genomes", *Heredity* 94:571-576 (2005).
Breckpot et al., "Lentivirally transduced dendritic cells as a tool for cancer immunotherapy", *The Journal of Gene Medicine* 5:654-667 (Apr. 23, 2003).
Brinster et al., "Regulation of metallothionein-thymidine kinase fusion plasmids injected into mouse eggs", *Nature* 296:39-42 (Mar. 4, 1982).
Brough et al., "Construction, Characterization, and Utilization of Cell Lines Which Inducibty Express the Adenovirus DNA-Binding Protein" *Virology*, 190624-634 (1992).
Brun et al., "Optimization of Transgene Expression at the Post-transcriptional Level in Neural Cells: Implications for Gene Therapy" 7(6):782-789 (Jun. 2003).
Buchwald et al., "Long-term, continuous intravenous heparin administration by an implantable infusion pump in ambulatory patients with recurrent venous thrombosis", *Surgery* 88:507-516 (Oct. 1980).
Cheng et al., "A Novel TARP-Promoter-Based Adenovirus against Hormone-Dependent and Hormone-Refractory Prostate Cancer", *Molecular Therapy* 10(2):355-364 (Aug. 2004).
Choi et al., "A Generic Intron Increases Gene Expression in Transgenic Mice", *Molecular and Cellular Biology* 11(6):3070-3074 (Jun. 1991).
Connor et al., "Sustained Intravesical'Interferon Protein Exposure Is Achieved Using an Adenoviral-Mediated Gene Delivery System: A Study in Rats Evaluating Dosing Regimens", Urology 66(1):224-229 (2005).
Davison et al., "Genetic content and evolution of adenoviruses", *Journal of General Virology* 84:2895-2908 (2003).
Demers et al., "Tumor Growth Inhibition by Interferon-α using PEGytated Protein or Adenovirus Gene Transfer with Constitutive or Regulated Expression", *Molecular Therapy* 6(1):50-56 (Jul. 2002).
Demers et al., "Interferon-α2b Secretion by Adenovirus-Mediated Gene delivery in Rat, Rabbit, and Chimpanzee Results in Similar Pharmacokinetic Profiles", Toxicology and Applied Pharmacology 180:36-42 (2002).
Di Simone et al.. "The Sear Urchin sns Insulator Blocks CMV Enhancer following Integration in Human Cells", Biochemical and Biophysical Research Communications, 284:987-992 (2001).
Donello et al., "Woodchuck Hepatitis Virus Contains a Tripartite Posttranscriptional Regulatory Element", *Journal of Virology* 72(6):5085-5092 (Jun. 1998).
Dunn et al., "The many roles of the transcriptional regulatory CTCF", *Biochem. Cell Biology* 81:161-167 (2003).
Dunn et al., "The insulator binding protein CTCF associates with the nuclear matrixx", *Experimental Cell Research* 288:218-223 (2003).
During et al., "Controlled Releasse of Dopamine from a Polymeric Brain Implant: In Vivo Characterization", *Annals of Neurology* 25(4):351-356 (Apr. 1989).
Emery et al., "Development of virus vectors for gene therapy of β chain hemoglobinopathies: flanking with a chromatin insulator reduces γ-globin gene silencing in vivo", *Blood* 100(6):2012-2019, 2002.
Farrell et al., "Conserved CTCF Insulator Elements Flank the Mouse and Human β-Globin Loci", *Molecular and Cellular Biology* 22(11):3820-3831 (Jun. 2002).
Glover et al., "Adenoviral-Mediated, High-Level, Cell-Specific Transgene Expression: A *SYN1*-WPRE Cassette Mediates Increased Transgene Expression with No Loss of Neuron Specificity", *Molecular Therapy* 5(5):509-516 (May 2002).
Glover et al., "Long-term transgene expression can be mediated in the brain by adenoviral vectors when pow3erful neuron-specific promoters are used", *The Journal of Gene Medicine* 5:554-559 (May 2003).
Graham et al., "Transformation of Rat Cells by Can of Human Adenovirus 5", *Virology* 54:536-539 (1973).
Gropp et al., "Stable Genetic Modification of Human Embryonic Stem Cells by Lentiviral Vectors", *Molecular Therapy*7(2):281-287 (Feb. 2003).
Hardy et al., "Construction of Adenovirus Vectors through Cre-*lox* Recombination". *Journal of Virology* 71(3):1842-1849 (Mar. 1997).
Haruna et al., "Separation of Adenovirus by Chromatography on DEAE-Cellulose", *Virology* 13(2):264-267 (Feb. 1961).

Hermening et al., "Increased protein expression from adenoviral shuttle plasmids and vectors by insertion of a small chimeric intron sequence", *Journal of Virological Methods* 122:73-77 (2004).
Howard et al., "Intracerebral drug delivery in rats with lesion-induced memory deficits", *J. Neurosurgery* 71:105-112 (1989).
Huang et al., "Hepatitis B Virus RNA Element That Facilitates Accumulation of Surface Gene Transcripts in the Cytoplasm", *Journal of Virology* 68(5):3193-3199 (May 1994).
Huyghe et al., "Purification of a Type 5 Recombinant Adenovirus Encoding Human p53 by Column Chromatography", *Human Gene Therapy* 6:1403-1416 (Nov. 1995).
Iqbal Ahmed et al., "Interferon α2b gene delivery using adenoviral vector causes inhibition of tumor growth in xenograft models from a variety of cancers", *Cancer Gene Therapy* 8(10):788-795 (2001).
Jakobsson et al., "Dynamics of transgene expression in a neural stem cell line transduced with lentiviral vectors incorporating the cHS4 insulator", *Experimental Cell Research* 298:611-623 (2004).
Jerne et al., "Towards A Network Theory of the Immune System", *Ann. Immunol.*, 125C:373-389 (1974).
Jerne et al., "Recurrent idiotopes and internal images", The EMBO Journal, 1(2):243-247 (1982).
Kanduri et al., "Multiple Nucleosome Positioning Sites Regulate the CTCF-Mediated Insulator Function of the H19 Imprinting Control Region", *Molecular and Cellular Biology* 22(10):3339-3344 (May 2002).
Klemperer et al., "Study of Adenovirus Antigens Fractionated by Chromatography on DEAE-Celllulose", *Virology* 9:536-545 (1959).
Kochanek et al., "A new adenoviral vector: Replacement of all viral coding sequences with 28 kb of DNA independently expressing both full-length dystrophin and β-galactosidase", *Proceedings of the National Academy of Sciences USA* 93:5731-5736 (Jun. 1996).
Kumar-Singh et al., "Encapsidaed adenovirus minichromosomes allow delivery and expression of a 14 kb dystrophin cDNA to muscle cells", *Human Molecular Genetics* 5(7):913-921 (1996).
Langer, "New Methods of Drug Delivery", *Science* 249:1527-1533 (Sep. 28, 1990).
Langer, Chemical and Physical Structure of Polymers as Carriers for Controlled Release of Bioactive Agents: A Review, *J. Macromol. Sci Rev Macromol. Chem.. Phys.* C23(1):61-126 (1983).
Langer, "Implantable Controlled Release Systems", *Pharmacol. Ther.* 21:35-51 (1983).
Lee et al., "Comparison of Various Expression Plasmids for the Induction of Immune Response by DNA Immunization", *Mol. Cells* 7(4):495-501 (Mar. 21, 1997).
Levy, "Inhibition of Calcification of Bioprosthetic Heart Valves by Local Controlled-Release Diphosphonate", *Science* 228:190-192 (Apr. 12, 1985).
Lewis et al., "Geonomic Imprinting: CTCF Protects the Boundaries", *Current Biology* 14:R284-R286 (Apr. 6, 2004).
Liu et al., "HnRNP L binds a *cis*-acting RNA sequence element that enables intron-independent gene expression", *Genes & Development* 9:1766-1780 (1995).
Lutz et al., "Transcriptional repression by the insulator protein CTCF involves histone deacetylases", *Nucleic Acids Research* 28(8):1707-1713 (2000).
Mangeot et al., "High Levels of Transduction of Human Dendritic Cells with Optimized SIV Vectors", *Molecular Therapy* 5(3):283-290 (Mar. 2002).
Martin-Duque et al., "Direct Comparison of the Insulating Properties of Two genetic Elements in an Adenoviral Vector Containing Two Different Expression Cassettes", *Human Gene Therapy* 15:995-1002 (Oct. 2004).
McCutchan et al., "Enhancement of the Infectivity of Simian Virus 40 Deoxyribonucleic Acid with Diethyl-aminoethyl-Dextran", *Journal of the National Cancer Institute* 41:351-357 (Mar. 6, 1968).
Mitani et al., "Rescue, propagation, and partial purificastion of a heler virus-dependent adenovirus vector", *Proceedings of the National Academy of Sciences USA* 92:3854-3858 (Apr. 1995).
Mukhopadhyay et al., "The Binding Sites for the Chromatin Insulator Protein CTCF Map to DNA Methylation-Free Domains Genome-Wide", *Genome Research* 14:1594-1602 (Jul. 2004).
Pannell et al., "Silencing of gene expression: implications for design of retrovirus vectors", *Rev. Med. Virol.* 11:205-217 (2001).

Parks et al., "A helper-dependent adenovirus vector system: Removal of helper virus by Cre-mediated excision of the viral packaging signal", *Proceedings of the National Academy of Sciences USA* 93:13565-13570 (Nov. 1996).

Philipson, "Separation on DEAE Cellulose of Components Associated with Adenovirus Reproduction", *Virology* 10:459-465 (1960).

Pluta et al., "Tight control of transgene expression by lentivirus vectors containing second-generation tetracycline-responsive promoters", *The Journal of Gene Medicine* 7:803-817 (Jan. 17, 2005).

Puthenveetil et al., "Successful correction of the human β-thalassemia major phenotype using a lentiviral vector", *Blood* 104(12):3445-3453 (Dec. 1, 2004).

Qu et al., "Homogeneity and long-term stability of tetracycline-regulated gene expression with low basal activity by using the rtTA2S-M2 transactivator and insulator-flanked reporter vectors", *Gene* 327:61-73 (2004).

Recillas-Targa et al., "Position-effect protection and enhancer blocking by the chickenβ-globin insulator are separable activities". *Proceedings of the National Academy of Sciences USA* 99(10)6883-6888 (May 14, 2002).

Rincón-Arano et al., "Sustained Heterologous Transgene Expression in Mammalian and Avian Cell Lines", *Methods in Molecular Biology* 267:435-450 (2004).

Robert et al., "A SIN Lentiviral Vector Containing PEGA cDNA Allows Long-Term Phenotypic Correction of CD34+-Derived Cells from Patients with Paroxysmal Nocturnal Hemoglobinuria", *Molecular Therapy* 7(3):304-316 (Mar. 2003).

Rodrigues, "Permeable packings and perfusion chromatography in protein separation", *Journal of Chromatography B* 699:47-61 (1997).

Saitoh et al., "Structural and functional conversation at the boundaries of the chicken β-globin domain", *The EMBO Journal* 19(10):2315-2322 (2000).

Saudek et al., "A Preliminary Trial of the Programmable Implantable Medication System for Insulin Delivery", *The New England Journal of Medicine* 321(9):574-579 (Aug. 31, 1989).

Schwenter et al., "Optimization of human erythropoietin secretion from MLV-infected human primary fibroblasts used for encapsulatd cell therapy", *The Journal of Gene Medicine* 5:246-257 (2003).

Sefton, "Implantable Pumps", *Critical Reviews in Biomedical Engineering* 14(3):201-240 (1987).

Shabram et al., "Analytical Anion-Exchange HPLC of Recombinant Type-5 Adenoviral Particles". *Human Gene Therapy* 8:453-465 (Mar. 1, 1997).

Simon et al., "Adenovirus-Mediated Transfer of the CFTR Gene to Lung of Nonhuman Primates: Toxicity Study", *Human Gene Therapy* 4:771-780 (1993).

Steinwaerder et al., "Insulation from viral transcriptional regulatory elements improves inducible transgene expression from adenovirus vectors in vitro and in vivo", *Gene Therapy* 7:556-567 (2000).

Szabó et al., "The chicken β-globin insulator element conveys chromatin boundary activity but not imprinting at the mouse *Igf2/H19* domain", *Development* 129:897-904 (2002).

Takada et al., "Evaluation of Heterologous Insulator Function with Regard to Chromosomal Position Effect in the Mouse blastocyst and Fetus", *Molecular Reproduction and Development* 57:232-237 (2000).

Thorvaldsen et al., "Analysis of Sequence Upstream of the Endogenous *H19* Gene Reveals Elements Both Essential and Dispensable for Imprinting", *Molecular and Cellular Biology* 22(8):2450-2462 (2002).

Valadez-Graham et al., "CTCF-dependent enhancer blockers at the upstream region of the chicken α-globin gene domain", *Nucleic Acids Research* 32(4):1354-1362 (Feb. 23, 2004).

Vassaux et al., "Insulation of a conditionally expressed transgene in an adenoviral vector", *Gene Therapy* 6:1192-1197 (Jan. 9, 1999).

Wagner et al., "The human β-globin gene and a functional viral thymidine kinase gene in developing mice". *Proceedings of the National Academy of Sciences USA* 78(8):5016-5020 (Aug. 1981).

Werner et al., "B-cell-specific transgene expression using a self-inactivating retroviral vector with human CD19 promoter and viral post-transcriptional regulatory element", *Gene Therapy* 11:992-1000 (2004).

Xu et al., "Woodchuck hepatitis virus post-transcriptional regulation element enhances transgene expression from adenovirus vectors", *Biochimica of Biophysica Acta* 1621:266-271 (2003).

Xu et al., "Strength evaluation of transcriptional regulatory elements for transgene expression by adenovirus vector". *Journal of Controlled Release* 81:155-163 (2002).

Yam et al., "Design of HIV Vectors for Efficient Gene Delivery into Human Hematopoietic Cells", *Molecular Therapy* 5(4):479-484 (Apr. 2002).

Yamamoto et al., "Identification of a Functional Promoter in the Long Terminal Repeat of Rous Sarcoma Virus", *Cell* 22:787-797 (Dec. 1980).

Yannaki et al., "Topological Constraints Governing the Use of the Chicken HS4 Chromatin Insulastor in Oncoretrovirus Vectors", *Molecular Therapy* 5(5):589-598 (May 2002).

Yao et al., "Retrovirus silencer blocking by the cHS4 insulator is CTCF independent", *Nucleic Acids Research* 31(18):5317-5323 (2003).

Ye et al., "Insulation from viral transcriptional regulatory elements enables improvement to hepatoma-specific gene expression from adenovirus vectors", *Biochemical and Biophysical Research Communications* 307:759-764 (2003).

Youil et al.. "Comparative Analysis of the Effects of Packaging Signal, Transgene Orientation, Promoters. Polyadenylation Signals, and E3 Region on Growth Properties of First-Generation Adenoviruses", *Human Gene Therapy* 14:1017-1034 (Jul. 1. 2003).

Yusufzai et al., "CTCF Tethers an Insulator to Subnuclear Sites, Suggesting Shared Insulator Mechanisms across Species", *Molecular Cell* 13:291-298 (Jan. 30, 2004).

Yusufzai et al., "The 5'-HS4 chicken β-globin insulator is a CTCF-dependent nuclear matrix-associated element", *Proceedings of the National Academy of Sciences USA* 101(23):8620-8624 (Jun. 8, 2004).

Zhang et al., "Dynamic association of the mammalian insulator protein CTCF with centrosomes and the midbody", *Experimental bell Research* 294:86-93 (2004).

Zhao et al., "An insulator blocks spreading of histone acetylation and interferes with RNA polymerase II transfer between an enhancer and gene", *Nucleic Acids Research* 32(16):4903-414(2004).

Zufferey et al., "Woodchuck Hepatitis Vrius Posttranscriptional Regulatory element Enhances Expression of Transgenes Delivered by Retroviral Vectors". *Journal of Virology* 73(4):2886-2892 (Apr. 1999).

GenBank Accession No. AC000008 (Human Adenovirus C Serotype 5) dated Oct. 31, 1996 (Replaced by AC003656).

GenBank Database Accession No. AY339865 (Human adenovirus C serotype 5) dated Aug. 13, 2007.

PCT International Search Report dated Feb. 29, 2008 for corresponding PCT Application No. PCT/US2006/046942.

Babiss et al, "Adenovirus E1B Proteins Are Required for Accumulation of Late Viral mRNA and for Effects on Cellular mRNA Translation and Transport", Molecular and Cellular Biology, vol. 5, No. 10, pp. 2552-2558 (1985).

Bayley et al, "Adenovirus E1A proteins and transformation (Review)", International Journal of Oncology, vol. 5, pp. 425-444 (1994).

Branton et al, "Transformation by Human Adenoviruses", Biochimca et Biophysica Acta, vol. 780, pp. 67-94 (1985).

Condon et al, "Development of a Chinese Hamster Ovary Cell Line for Recombinant Adenovirus-Mediated Gene Expression", Biotechnol. Prog., vol. 19, pp. 137-143 (2003).

Demers et al, "Pharmacologic Indicators of Antitumor Efficacy for Oncolytic Virotherapy", Cancer Research, vol. 63, pp. 4003-4008 (2003).

Doronin et al, "Tumor-specific, Replication-Competent Adenovirus Vectors Overexpressing the Adenovirus Death Protein", J. Virol., vol. 74, No. 13, pp. 6147-6155 (2000).

Fallaux et al, "New Helper Cells and Matched Early Region 1-Deleted Adenovirus Vectors Prevent Generation of Replication-Competent Adenoviruses", Human Gene Therapy, vol. 9, pp. 1909-1917 (1998).

Frisch et al, "Adenovirus-5 E1A: Paradox and Paradigm", Nature Reviews Molecular Cell Biology, vol. 3, pp. 441-452 (2002).

Frisch, "Antioncogenic effect of adenovirus E1A in human tumor cells", Proc. Natl. Acad. Sci. USA, vol. 88, pp. 9077-9081 (1991).

Graham et al, "Characteristics of a Human Cell Line Transformed by DNA from Human Adenovirus Type 5", J. Gen Virol., vol. 36, pp. 59-74 (1977).

Guo et al, "Protein Tolerance to Random Amino Acid Change", PNAS, vol. 101, No. 25, pp. 9205-9210 (2004).

Harada et al, "p53-Independent and -Dependent Requirements for E1B-55K in Adenovirus Type 5 Replication", Journal of Virology, vol. 73, No. 7, pp. 5333-5344 (1999).

Howe et al, "Retinoblastoma Growth Suppressor and a 300-kDa Protein Appear to Regulate Cellular DNA Synthesis", Proc. Natl. Acad. Sci. USA, vol. 87, No. 15, pp. 5883-5887 (1990).

Howe et al, "Evaluation of E1-Mutant Adenoviruses as Conditionally Replicating Agents for Cancer Therapy", Mol. Ther., vol. 2, No. 5, pp. 485-495 (2000).

Howe et al, "Matching Complementing Functions of Transformed Cells with Stable Expression of Selected Viral Genes for Production of E1-Deleted Adenovirus Vectors", Virology, vol. 345, No. 1, pp. 220-230 (2006).

Imler et al, "Novel Complementation Cell Lines Derived from Human Lung Carcinoma A549 Cells Support the Growth of E-1 Deleted Adenovirus Vectors", Gene Therapy, vol. 3, pp. 75-84 (1996).

Lesk et al, "Prediction of Protein Function from Protein Sequence and Structure", pp. 27-28, downloaded Sep. 16, 2007.

Lochmuller et al, "Emergence of Early Region 1-Containing Replication-Competent Adenovirus in Stocks of Replication-Defective Adenovirus Recombinants (ΔE1+ΔE3) During Multiple Passages in 293 Cells", Human Gene Therapy, vol. 5, pp. 1485-1491 (1994).

Louis et al, "Cloning and Sequencing of the Cellular—Viral Junctions from the Human Adenovirus Type 5 Transformed 293 Cell Line", Virology, vol. 233, pp. 423-429 (1997).

Murakami et al, "A Single Short Stretch of Homology Between Adenoviral Vector and Packaging Cell Line Can Give Rise to Cytopathic Effect-Inducing, Helper-Dependent E1-Positive Particles", Human Gene Therapy, vol. 13, pp. 909-920 (2002).

Mymryk et al, "Induction of Apoptosis by Adenovirus Type 5 E1A in Rat Cells Requires a Proliferation Block", Oncogene, vol. 9, pp. 1187-1193 (1994).

Querido et al, "Regulation of p53 Levels by the E1B 55-Kilodalton Protein and E4orf6 in Adenovirus-Infected Cells", Journal of Virology, vol. 71, No. 5, pp. 3788-3798 (1997).

Rao et al, "The Adenovirus E1A Proteins Induce Apoptosis, Which is Inhibited by the E1B 19-kDa and Bcl-2 Proteins", Proc. Natl. Acad. Sci. USA, vol. 89, pp. 7742-7746 (1992).

Shenk, "Adenoviridae: the Viruses and Their Replication", Fields Virology, Third Edition, Chapter 67, vol. 2, pp. 2111-2148 (1996).

White et al, "Adenovirus E1B 19-Kilodalton Protein Overcomes the Cytotoxicity of E1A Proteins", Journal of Virology, vol. 65, No. 6, pp. 2968-2978 (1991).

Zhu et al, "Characterization of Replication-Competent Adenovirus Isolates from Large-Scale Production of a Recombinant Adenoviral Vector", Human Gene Therapy, vol. 10, pp. 113-121 (1999).

PCT International Search Report for PCT Application No. PCT/US2005/045097 mailed Jul. 3, 2006.

ATCC search results pp. 1-2, SL0003, downloaded Aug. 11, 2009.
ATCC search results pp. 1-2, SL0006, downloaded Aug. 11, 2009.
ATCC search results pp. 1-2, PTA-6231, downloaded Aug. 11, 2009.
ATCC search results pp. 1-2, PTA-6663, downloaded Aug. 11, 2009.

Berkner, Kathleen L., et al., "Effect of the tripartite leader on synthesis of a non-viral protein in an adenovirus 5 recombinant", *Nucleic Acids Research* 13(3):841-857 (1985).

Sheay, W., et al.; "Downstream Insertion of the Adenovirus Tripartite Leader Sequence Enhances Expression in Universal Eukaryotic Vectors"; *Biotechniques*; 15(5):856-862 (1993).

* cited by examiner

Figure 1. Schematic diagram of the structure of T2VP
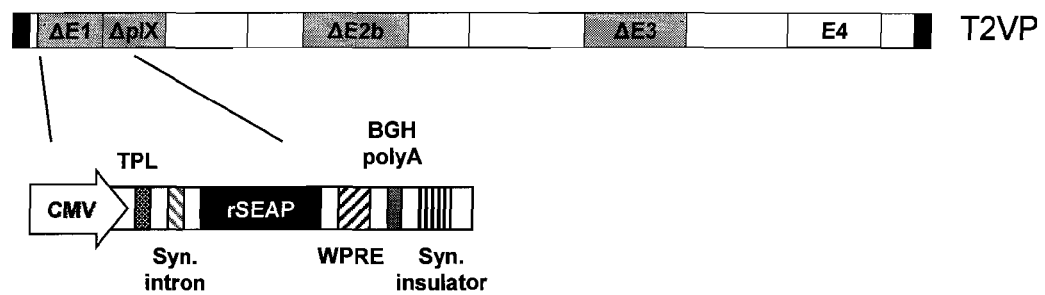

Figure 2. Comparison of SEAP expression in Ku-7 bladder cells infected with T2VP and other control viruses.
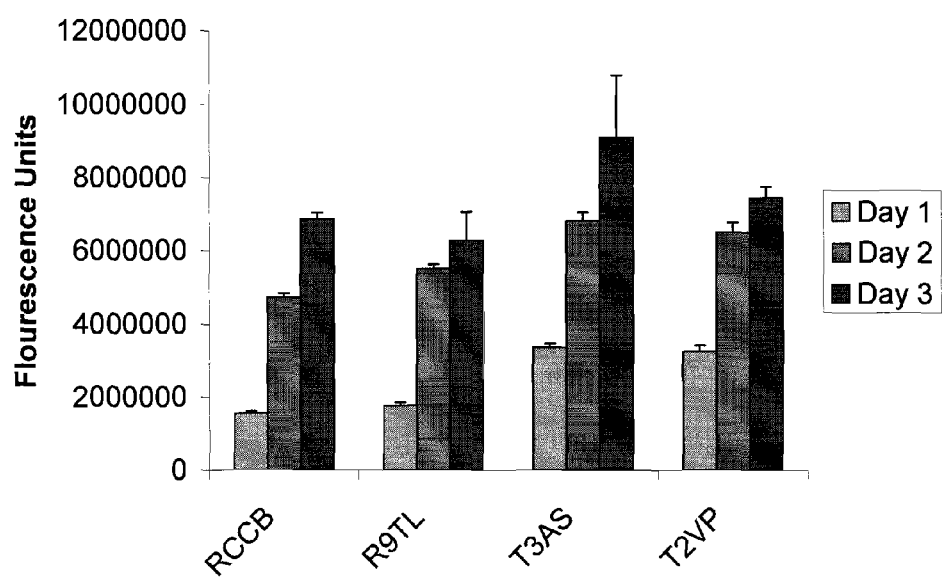

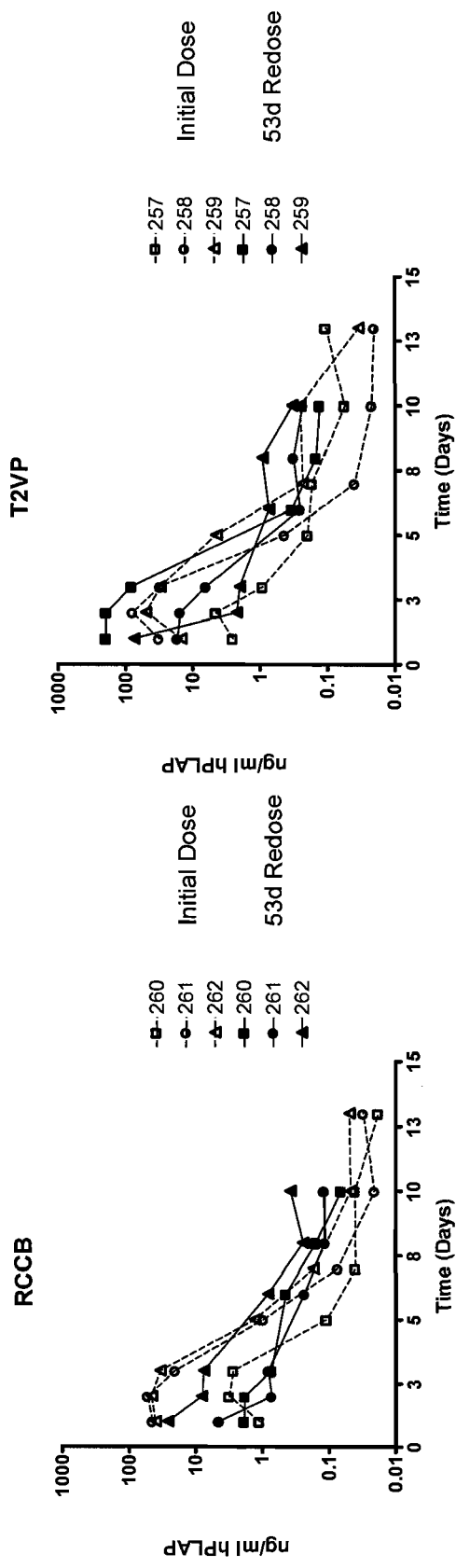
Figure 3. In vivo analysis of urine SEAP expression following intravesical delivery of T2VP and RCCB (control).

Figure 4. Schematic diagram of the structure of T8BF compared to IACB
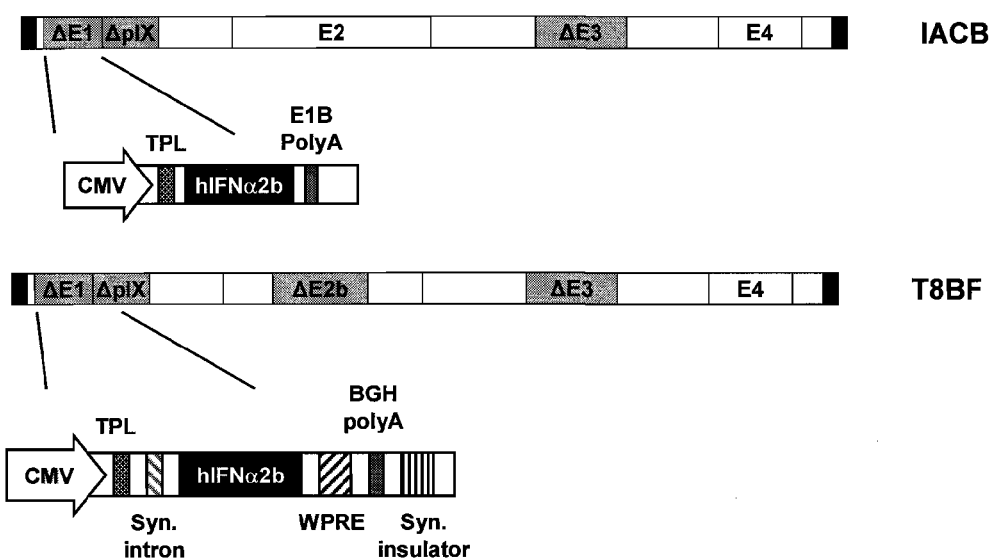

Figure 5A. Sequence and localition of features of the transgene cassette from T8BF.

```
     CMV IE Promoter   (Gen X03922)
365  ATGTACGGGC CAGATATACG CGTTGACATT GATTATTGAC TAGTTATTAA
     TACATGCCCG GTCTATATGC GCAACTGTAA CTAATAACTG ATCAATAATT
              CMV IE Promoter   (Gen X03922)
415  TAGTAATCAA TTACGGGGTC ATTAGTTCAT AGCCCATATA TGGAGTTCCG
     ATCATTAGTT AATGCCCCAG TAATCAAGTA TCGGGTATAT ACCTCAAGGC
              CMV IE Promoter   (Gen X03922)
465  CGTTACATAA CTTACGGTAA ATGGCCCGCC TGGCTGACCG CCCAACGACC
     GCAATGTATT GAATGCCATT TACCGGGCGG ACCGACTGGC GGGTTGCTGG
              CMV IE Promoter   (Gen X03922)
515  CCCGCCCATT GACGTCAATA ATGACGTATG TTCCCATAGT AACGCCAATA
     GGGCGGGTAA CTGCAGTTAT TACTGCATAC AAGGGTATCA TTGCGGTTAT
              CMV IE Promoter   (Gen X03922)
565  GGGACTTTCC ATTGACGTCA ATGGGTGGAG TATTTACGGT AAACTGCCCA
     CCCTGAAAGG TAACTGCAGT TACCCACCTC ATAAATGCCA TTTGACGGGT
              CMV IE Promoter   (Gen X03922)
615  CTTGGCAGTA CATCAAGTGT ATCATATGCC AAGTACGCCC CCTATTGACG
     GAACCGTCAT GTAGTTCACA TAGTATACGG TTCATGCGGG GGATAACTGC
              CMV IE Promoter   (Gen X03922)
665  TCAATGACGG TAAATGGCCC GCCTGGCATT ATGCCCAGTA CATGACCTTA
     AGTTACTGCC ATTTACCGGG CGGACCGTAA TACGGGTCAT GTACTGGAAT
              CMV IE Promoter   (Gen X03922)
715  TGGGACTTTC CTACTTGGCA GTACATCTAC GTATTAGTCA TCGCTATTAC
     ACCCTGAAAG GATGAACCGT CATGTAGATG CATAATCAGT AGCGATAATG
              CMV IE Promoter   (Gen X03922)
765  CATGATGATG CGGTTTTGGC AGTACATCAA TGGGCGTGGA TAGCGGTTTG
     GTACTACTAC GCCAAAACCG TCATGTAGTT ACCCGCACCT ATCGCCAAAC
              CMV IE Promoter   (Gen X03922)
815  ACTCACGGGG ATTTCCAAGT CTCCACCCCA TTGACGTCAA TGGGAGTTTG
     TGAGTGCCCC TAAAGGTTCA GAGGTGGGGT AACTGCAGTT ACCCTCAAAC
                           CMV Promoter
              CMV IE Promoter   (Gen X03922)
865  TTTTGACTAG TAAATCAACG GGACTTTCCA AAATGTCGTA ACAACTCCGC
     AAAACTGATC ATTTAGTTGC CCTGAAAGGT TTTACAGCAT TGTTGAGGCG
                           CMV Promoter
              CMV IE Promoter   (Gen X03922)
915  CCCATTGACG CAAATGGGCG GTAGGCGTGT ACGGTGGGAG GTCTATATAA
     GGGTAACTGC GTTTACCCGC CATCCGCACA TGCCACCCTC CAGATATATT
```

Figure 5B.

CMV Promoter

Transcription Start Site

CMV IE Promoter (Gen X03922)                              Tripartite Leader

965  GCAGAGCTCG TTTAGTGAAC CGTCAGATAA GCTTCGCGCG GGTACCACTC
     CGTCTCGAGC AAATCACTTG GCAGTCTATT CGAAGCGCGC CCATGGTGAG
              Ad2 seq (6048-6079)
                                                Ad2 seq (bp7101-7172)

Tripartite Leader

1015 TCTTCGCATC GCTGTCTGCG AGGGCCAGCT GTTGGGCTCG CGGTTGAGGA
     AGAAGCGTAG CGACAGACGC TCCCGGTCGA CAACCCGAGC GCCAACTCCT
                 Ad2 seq (bp7101-7172)

Tripartite Leader

1065 CAAACTCTTC GCGGTCTTTC CAGTACTCTT GGATCGGAAA CCCGTCGGCC
     GTTTGAGAAG CGCCAGAAAG GTCATGAGAA CCTAGCCTTT GGGCAGCCGG
     Ad2 seq (bp7101-7172)
                      Ad2 seq (bp9634-9694)

Tripartite Leader

1115 TCCGAACGGT ACTCCGCCAC CGAGGGACCT GAGCGAGTCC GCATCGACCG
     AGGCTTGCCA TGAGGCGGTG GCTCCCTGGA CTCGCTCAGG CGTAGCTGGC
     Ad2 seq (bp9634-9694)             Synthetic Intron Tripartite Leader              Splice Donor 1165 GATCGGAAAA CCTCTCGAGT CTAGAGGTAA GTGTCTTCCT CCTGTTTCCT
     CTAGCCTTTT GGAGAGCTCA GATCTCCATT CACAGAAGGA GGACAAAGGA
                       Synthetic Intron 1215 TCCCCTGCTA TTCTGCTCAA CCTTCCTATC AGAAACTGCA GTATCTGTAT
     AGGGGACGAT AAGACGAGTT GGAAGGATAG TCTTTGACGT CATAGACATA
              Synthetic Intron AttB1        AttB1

1265 TTTTGCTAGC ACAAGTTTGT ACAAAAAAGC AGGCTCTTTT TTTCTCTTCA
     AAAACGATCG TGTTCAAACA TGTTTTTTCG TCCGAGAAAA AAAGAGAAGT
                            Human interferon-alpha(2b) gene including signal Splice Acceptor                        G in GenBank S64991

1315 CAGGCTCCAG TCGACCACCA TGGCCTTGAC CTTTGCTTTA CTAGTGGCCC
     GTCCGAGGTC AGCTGGTGGT ACCGGAACTG GAAACGAAAT GATCACCGGG

Figure 5C.

```
                                    TCT in GenBank S64991
                                    ~~~~
                                            Genomic coding sequence for
            mature human
                                            ~~~~~~~~~~~~
            Human interferon-alpha(2b) gene including signal
            ████████████████████████████████████████████████
                        TCAAG in GenBank S64991
                        ~~~~~
      1365  TCCTGGTGCT CAGCTGCAAG AGCTCCTGCA GCGTGGGCTG TGATCTGCCT
            AGGACCACGA GTCGACGTTC TCGAGGACGT CGCACCCGAC ACTAGACGGA
            Human interferon-alpha(2b) gene including signal
            ████████████████████████████████████████████████
                 Genomic coding sequence for mature human
            ~~~~~~~~~~~~~~~~~~~~~~~~~~~~~~~~~~~~~~~~~~~~~~~~~~
      1415  CAAACCCACA GCCTGGGTAG CAGGAGGACC TTGATGCTCC TGGCACAGAT
            GTTTGGGTGT CGGACCCATC GTCCTCCTGG AACTACGAGG ACCGTGTCTA
            Human interferon-alpha(2b) gene including signal
            ████████████████████████████████████████████████
                 Genomic coding sequence for mature human
            ~~~~~~~~~~~~~~~~~~~~~~~~~~~~~~~~~~~~~~~~~~~~~~~~~~
      1465  GAGGAGAATC TCTCTTTTCT CCTGCTTGAA GGACAGACAT GACTTTGGAT
            CTCCTCTTAG AGAGAAAAGA GGACGAACTT CCTGTCTGTA CTGAAACCTA
            Human interferon-alpha(2b) gene including signal
            ████████████████████████████████████████████████
                 Genomic coding sequence for mature human
            ~~~~~~~~~~~~~~~~~~~~~~~~~~~~~~~~~~~~~~~~~~~~~~~~~~
      1515  TTCCCCAGGA GGAGTTTGGC AACCAGTTCC AAAAGGCTGA AACCATCCCT
            AAGGGGTCCT CCTCAAACCG TTGGTCAAGG TTTTCCGACT TTGGTAGGGA
            Human interferon-alpha(2b) gene including signal
            ████████████████████████████████████████████████
                 Genomic coding sequence for mature human
            ~~~~~~~~~~~~~~~~~~~~~~~~~~~~~~~~~~~~~~~~~~~~~~~~~~
      1565  GTCCTCCATG AGATGATCCA GCAGATCTTC AATCTCTTCA GCACAAAGGA
            CAGGAGGTAC TCTACTAGGT CGTCTAGAAG TTAGAGAAGT CGTGTTTCCT
            Human interferon-alpha(2b) gene including signal
            ████████████████████████████████████████████████
                 Genomic coding sequence for mature human
            ~~~~~~~~~~~~~~~~~~~~~~~~~~~~~~~~~~~~~~~~~~~~~~~~~~
      1615  CTCATCTGCT GCTTGGGATG AGACCCTCCT AGACAAATTC TACACTGAAC
            GAGTAGACGA CGAACCCTAC TCTGGGAGGA TCTGTTTAAG ATGTGACTTG
            Human interferon-alpha(2b) gene including signal
            ████████████████████████████████████████████████
                 Genomic coding sequence for mature human
            ~~~~~~~~~~~~~~~~~~~~~~~~~~~~~~~~~~~~~~~~~~~~~~~~~~
      1665  TCTACCAGCA GCTGAATGAC CTGGAAGCCT GTGTGATACA GGGGGTGGGG
            AGATGGTCGT CGACTTACTG GACCTTCGGA CACACTATGT CCCCCACCCC
            Human interferon-alpha(2b) gene including signal
            ████████████████████████████████████████████████
                 Genomic coding sequence for mature human
            ~~~~~~~~~~~~~~~~~~~~~~~~~~~~~~~~~~~~~~~~~~~~~~~~~~
      1715  GTGACAGAGA CTCCCCTGAT GAAGGAGGAC TCCATTCTGG CTGTGAGGAA
            CACTGTCTCT GAGGGGACTA CTTCCTCCTG AGGTAAGACC GACACTCCTT
```

Figure 5D.

Human interferon-alpha(2b) gene including signal

Genomic coding sequence for mature human

1765 ATACTTCCAA AGAATCACTC TCTATCTGAA AGAGAAGAAA TACAGCCCTT
     TATGAAGGTT TCTTAGTGAG AGATAGACTT TCTCTTCTTT ATGTCGGGAA

Human interferon-alpha(2b) gene including signal

Genomic coding sequence for mature human

1815 GTGCCTGGGA GGTTGTCAGA GCAGAAATCA TGAGATCTTT TTCTTTGTCA
     CACGGACCCT CCAACAGTCT CGTCTTTAGT ACTCTAGAAA AAGAAACAGT

Stop codon for the human IFN-alpha(2b) transgene

Human interferon-alpha(2b) gene including signal

Genomic coding sequence for mature human

1865 ACAAACTTGC AAGAAAGTTT AAGAAGTAAG GAATGAATTC CTGCAGCCCG
     TGTTTGAACG TTCTTTCAAA TTCTTCATTC CTTACTTAAG GACGTCGGGC

WPRE

1915 GGTCTAGAGG ATCCAGCGGC CGCTGTTAAT CAACCTCTGG ATTACAAAAT
     CCAGATCTCC TAGGTCGCCG GCGACAATTA GTTGGAGACC TAATGTTTTA

WPRE

1965 TTGTGAAAGA TTGACTGGTA TTCTTAACTA TGTTGCTCCT TTTACGCTAT
     AACACTTTCT AACTGACCAT AAGAATTGAT ACAACGAGGA AAATGCGATA

WPRE

2015 GTGGATACGC TGCTTTAATG CCTTTGTATC ATGCTATTGC TTCCCGTATG
     CACCTATGCG ACGAAATTAC GGAAACATAG TACGATAACG AAGGGCATAC

WPRE

2065 GCTTTCATTT TCTCCTCCTT GTATAAATCC TGGTTGCTGT CTCTTTATGA
     CGAAAGTAAA AGAGGAGGAA CATATTTAGG ACCAACGACA GAGAAATACT

WPRE

2115 GGAGTTGTGG CCCGTTGTCA GGCAACGTGG CGTGGTGTGC ACTGTGTTTG
     CCTCAACACC GGGCAACAGT CCGTTGCACC GCACCACACG TGACACAAAC

WPRE

2165 CTGACGCAAC CCCCACTGGT TGGGGCATTG CCACCACCTG TCAGCTCCTT
     GACTGCGTTG GGGGTGACCA ACCCCGTAAC GGTGGTGGAC AGTCGAGGAA

WPRE

2215 TCCGGGACTT TCGCTTTCCC CCTCCCTATT GCCACGGCGG AACTCATCGC
     AGGCCCTGAA AGCGAAAGGG GGAGGGATAA CGGTGCCGCC TTGAGTAGCG

WPRE

2265 CGCCTGCCTT GCCCGCTGCT GGACAGGGGC TCGGCTGTTG GGCACTGACA
     GCGGACGGAA CGGGCGACGA CCTGTCCCCG AGCCGACAAC CCGTGACTGT

WPRE

2315 ATTCCGTGGT GTTGTCGGGG AAGCTGACGT CCTTTCCATG GCTGCTCGCC
     TAAGGCACCA CAACAGCCCC TTCGACTGCA GGAAAGGTAC CGACGAGCGG

Figure 5E.

```
                              WPRE
2365  TGTGTTGCCA CCTGGATTCT GCGCGGGACG TCCTTCTGCT ACGTCCCTTC
      ACACAACGGT GGACCTAAGA CGCGCCCTGC AGGAAGACGA TGCAGGGAAG
                              WPRE
2415  GGCCCTCAAT CCAGCGGACC TTCCTTCCCG CGGCCTGCTG CCGGCTCTGC
      CCGGGAGTTA GGTCGCCTGG AAGGAAGGGC GCCGGACGAC GGCCGAGACG
                              WPRE
2465  GGCCTCTTCC GCGTCTTCGC CTTCGCCCTC AGACGAGTCG GATCTCCCTT
      CCGGAGAAGG CGCAGAAGCG GAAGCGGGAG TCTGCTCAGC CTAGAGGGAA
           WPRE
2515  TGGGCCGCCT CCCCGCCTGT TTCTAGTTGA TCCGAGCTCG GTACCAAGCT
      ACCCGGCGGA GGGGCGGACA AAGATCAACT AGGCTCGAGC CATGGTTCGA
                                       BGH reverse priming site
                                       ~~~~~~~~~~~~~~~~~~~~
                                       BGH polyA region
2565  TAAGTTTAAA CCGCTGATCA GCCTCGACTG TGCCTTCTAG TTGCCAGCCA
      ATTCAAATTT GGCGACTAGT CGGAGCTGAC ACGGAAGATC AACGGTCGGT
                       BGH polyA region
2615  TCTGTTGTTT GCCCCTCCCC CGTGCCTTCC TTGACCCTGG AAGGTGCCAC
      AGACAACAAA CGGGGAGGGG GCACGGAAGG AACTGGGACC TTCCACGGTG
                     BGH polyA
                     ~~~~~~~~
                     BGH polyA region
2665  TCCCACTGTC CTTTCCTAAT AAAATGAGGA AATTGCATCG CATTGTCTGA
      AGGGTGACAG GAAAGGATTA TTTTACTCCT TTAACGTAGC GTAACAGACT
                           BGH polyA region
2715  GTAGGTGTCA TTCTATTCTG GGGGGTGGGG TGGGGCAGGA CAGCAAGGGG
      CATCCACAGT AAGATAAGAC CCCCCACCCC ACCCCGTCCT GTCGTTCCCC
              BGH polyA region
2765  GAGGATTGGG AAGACAATAG CAGGCATGCT GGGGATGCGG TGGGCTCTAT
      CTCCTAACCC TTCTGTTATC GTCCGTACGA CCCCTACGCC ACCCGAGATA
                                                 CTCF binding site
2815  GGCTTCTGAG GCGGAAAGAA CCATCTAGTG GGCAGATCCC CCAGGGATGT
      CCGAAGACTC CGCCTTTCTT GGTAGATCAC CCGTCTAGGG GGTCCCTACA
               CTCF binding site              CTCF binding site
2865  AATTACGTCC CTCCCCCGCT AGGGGGCAGC AAGATCCCCC AGGGATGTAA
      TTAATGCAGG GAGGGGGCGA TCCCCCGTCG TTCTAGGGGG TCCCTACATT
             CTCF binding site              CTCF binding site
2915  TTACGTCCCT CCCCCGCTAG GGGGCAGCAA GATCCCCCAG GGATGTAATT
      AATGCAGGGA GGGGGCGATC CCCCGTCGTT CTAGGGGGTC CCTACATTAA
             CTCF binding site              CTCF binding site
2965  ACGTCCCTCC CCCGCTAGGG GGCAGCAAGA TCCCCCAGGG ATGTAATTAC
      TGCAGGGAGG GGGCGATCCC CCGTCGTTCT AGGGGGTCCC TACATTAATG
             CTCF binding site
3015  GTCCCTCCCC CGCTAGGGGG CAGCAGGATC CTCGAATGCA TCGCGCTCTA
      CAGGGAGGGG GCGATCCCCC GTCGTCCTAG GAGCTTACGT AGCGCGAGAT
```

Figure 6A. Full sequence of the T8BF virus.

```
   1 taacatcatc aataatatac cttattttgg attgaagcca atatgataat gagggggtgg
  61 agtttgtgac gtggcgcggg gcgtgggaac ggggcgggtg acgtagtagt gtggcggaag
 121 tgtgatgttg caagtgtggc ggaacacatg taagcgacgg atgtggcaaa agtgacgttt
 181 ttggtgtgcg ccggtgtaca caggaagtga caatttcgc gcggttttag gcggatgttg
 241 tagtaaattt gggcgtaacc gagtaagatt tggccatttt cgcgggaaaa ctgaataaga
 301 ggaagtgaaa tctgaataat tttgtgttac tcatagcgcg taatatttgt ctagggccgc
 361 ggcgatgtac gggccagata tacgcgttga cattgattat tgactagtta ttaatagtaa
 421 tcaattacgg ggtcattagt tcatagccca tatatggagt tccgcgttac ataacttacg
 481 gtaaatggcc cgcctggctg accgcccaac gaccccgcc cattgacgtc aataatgacg
 541 tatgttccca tagtaacgcc aatagggact ttccattgac gtcaatgggt ggagtattta
 601 cggtaaactg cccacttggc agtacatcaa gtgtatcata tgccaagtac gcccctatt
 661 gacgtcaatg acggtaaatg gcccgcctgg cattatgccc agtacatgac cttatgggac
 721 tttcctactt ggcagtacat ctacgtatta gtcatcgcta ttaccatgat gatgcggttt
 781 tggcagtaca tcaatgggcg tggatagcgg tttgactcac ggggatttcc aagtctccac
 841 cccattgacg tcaatgggag tttgttttga ctagtaaatc aacgggactt tccaaaatgt
 901 cgtaacaact ccgcccatt gacgcaaatg ggcggtaggc gtgtacggtg ggaggtctat
 961 ataagcagag ctcgtttagt gaaccgtcag ataagcttcg cgcgggtacc actctcttcg
1021 catcgctgtc tgcgagggcc agctgttggg ctcgcggttg aggacaaact cttcgcggtc
1081 tttccagtac tcttggatcg gaaacccgtc ggcctccgaa cggtactccg ccaccgaggg
1141 acctgagcga gtccgcatcg accggatcgg aaaacctctc gagtctagag gtaagtgtct
1201 tcctcctgtt tccttcccct gctattctgc tcaaccttcc tatcagaaac tgcagtatct
1261 gtattttgc tagcacaagt ttgtacaaaa aagcaggctc ttttttctc ttcacaggct
1321 ccagtcgacc accatggcct tgacctttgc tttactagtg gccctcctgg tgctcagctg
1381 caagagctcc tgcagcgtgg gctgtgatct gcctcaaacc cacagcctgg gtagcaggag
1441 gaccttgatg ctcctggcac agatgaggag aatctctctt ttctcctgct tgaaggacag
1501 acatgacttt ggatttcccc aggaggagtt tggcaaccag ttccaaaagg ctgaaaccat
1561 ccctgtcctc catgagatga tccagcagat cttcaatctc ttcagcacaa aggactcatc
1621 tgctgcttgg gatgagaccc tctagacaa attctacact gaactctacc agcagctgaa
1681 tgacctggaa gcctgtgtga tacagggggt ggggtgaca gagactcccc tgatgaagga
1741 ggactccatt ctggctgtga ggaaatactc ccaaagaatc actctctatc tgaaagagaa
1801 gaaatacagc ccttgtgcct gggaggttgt cagagcagaa atcatgagat ctttttcttt
1861 gtcaacaaac ttgcaagaaa gtttaagaag taaggaatga attcctgcag cccgggtcta
1921 gaggatccag cggccgctgt taatcaacct ctggattaca aatttgtga aagattgact
1981 ggtattctta actatgttgc tccttttacg ctatgtggat acgctgcttt aatgcctttg
2041 tatcatgcta ttgcttcccg tatggctttc attttctcct ccttgtataa atcctggttg
2101 ctgtctcttt atgaggagtt gtggcccgtt gtcaggcaac gtggcgtggt gtgcactgtg
2161 tttgctgacg caaccccac tggttgggc attgccacca cctgtcagct ccttccggg
2221 actttcgctt tcccctccc tattgccacg gcggaactca tcgccgcctg ccttgcccgc
2281 tgctggacag ggctcggct gttgggcact gacaattccg tggtgttgtc ggggaagctg
2341 acgtccttc catggctgct cgcctgtgtt gccacctgga ttctgcgcgg gacgtccttc
2401 tgctacgtcc cttcggccct caatccagcg gaccttcctt cccgcggcct gctgccggct
2461 ctgcggcctc ttccgcgtct tcgccttcgc cctcagacga gtcggatctc cctttgggcc
2521 gcctcccgc ctgtttctag ttgatccgag ctcggtacca agcttaagtt taaaccgctg
2581 atcagcctcg actgtgcctt ctagttgcca gccatctgtt gtttgcccct cccccgtgcc
2641 ttccttgacc ctggaaggtg ccactccac tgtcctttcc taataaaatg aggaaattgc
2701 atcgcattgt ctgagtaggt gtcattctat ctgggggt ggggtggggc aggacagcaa
2761 gggggaggat tgggaagaca atagcaggca tgctgggat gcggtgggct ctatggcttc
2821 tgaggcggaa agaaccatct agtgggcaga tcccccaggg atgtaattac gtccctcccc
2881 cgctaggggg cagcaagatc cccagggat gtaattacgt cctcccccgct agggggca
2941 gcaagatccc ccagggatgt aattacgtcc ctcccccgct agggggcagc aagatccccc
3001 agggatgtaa ttacgtccct ccccgctag ggggcagcag gatcctcgaa tgcatcgcgc
3061 tctagatacg taggatccat cgattaacta taacggtcct aaggtagcga tttaaatgat
3121 cccatggccc aaaacataaa taaaaaccag actctgtttg gattttgatc aagcaagtgt
```

Figure 6B.

```
3181 cttgctgtct ttatttaggg gttttgcgcg cgcggtaggc ccgggaccag cggtctcggt
3241 cgttgagggt cctgtgtatt ttttccagga cgtggtaaag gtgactctgg atgttcagat
3301 acatgggcat aagcccgtct ctggggtgga ggtagcacca ctgcagagct tcatgctgcg
3361 gggtggtgtt gtagatgatc cagtcgtagc aggagcgctg ggcgtggtgc ctaaaaatgt
3421 ctttcagtag caagctgatt gccaggggca ggcccttggt gtaagtgttt acaaagcggt
3481 taagctggga tgggtgcata cgtggggata tgagatgcat cttggactgt attttaggt
3541 tggctatgtt cccagccata tccctccggg gattcatgtt gtgcagaacc accagcacag
3601 tgtatccggt gcacttggga aatttgtcat gtagcttaga aggaaatgcg tggaagaact
3661 tggagacgcc cttgtgacct ccgagatttt ccatgcattc gtccataatg atggcaatgg
3721 gcccacgggc ggcggcctgg gcgaagatat ttctgggatc actaacgtca tagttgtgtt
3781 ccaggatgag atcgtcatag gccattttta caaagcgcgg gcggagggtg ccagactgcg
3841 gtataatggt tccatccggc ccaggggcgt agttaccctc acagatttgc atttcccacg
3901 ctttgagttc agatggggg atcatgtcta cctgcggggc gatgaagaaa accgtttccg
3961 gggtagggga gatcagctgg gaagaaagca ggttcctgag cagctgcgac ttaccgcagc
4021 cggtgggccc gtaaatcaca cctattaccg gctgcaactg gtagttaaga gagctgcagc
4081 tgccgtcatc cctgagcagg ggggccactt cgttaagcat gtccctgact tgcatgtttt
4141 ccctgaccaa atgcgccaga aggcgctcgc cgcccagcga tagcagttct tgcaaggaag
4201 caaagttttt caacggtttg aggccgtccg ccgtaggcat gcttttgagc gtttgaccaa
4261 gcagttccag gcggtcccac agctcggtca cgtgctctac ggcatctcga tccagcatat
4321 ctcctcgttt cgcgggttgg ggcggctttc gctgtacggc agtagtcggt gctcgtccag
4381 acgggccagg gtcatgtctt ccacggggcg cagggtcctc gtcagcgtag tctgggtcac
4441 ggtgaagggg tgcgctccgg gctgcgcgct ggccagggtg cgcttgaggc tggtcctgct
4501 ggtgctgaag cgctgccggt cttcgccctg cgcgtcggcc aggtagcatt tgaccatggt
4561 gtcatagtcc agccctccg cggcgtggcc cttggcgcgc agcttgccct tggaggaggc
4621 gccgcacgag gggcagtgca gactttaag ggcgtagagc ttgggcgcga gaaataccga
4681 ttccggggag taggcatccg cgccgcaggc cccgcagacg gtctcgcatt ccacgagcca
4741 ggtgagctct ggccgttcgg ggtcaaaaac caggtttccc ccatgctttt tgatgcgttt
4801 cttacctctg gtttccatga gccggtgtcc acgctcggtg acgaaaaggc tgtccgtgtc
4861 cccgtataca gacttgagag gcctgtcctc gagcggtgtt ccgcggtcct cctcgtatag
4921 aaactcggac cactctgaga cgaaggctcg cgtccaggcc agcacgaagg aggctaagtg
4981 ggaggggtag cggtcgttgt ccactagggg gtccactcgc tccagggtgt gaagacacat
5041 gtcgccctct tcggcatcaa ggaaggtgat tggtttatag gtgtaggcca cgtgaccggg
5101 tgttcctgaa gggggctat aaaagggggt ggggcgcgt tcgtcctcac tctcttccgc
5161 atcgctgtct gcgagggcca gctgttgggg tgagtactcc ctctcaaaag cgggcatgac
5221 ttctgcgcta agattgtcag tttccaaaaa cgaggaggat ttgatattca cctggcccgc
5281 ggtgatgcct ttgagggtgg ccgcgtccat ctggtcagaa aagacaatct ttttgttgtc
5341 aagcttggtg gcaaacgacc cgtagagggc gttggacagc aacttggcga tggagcgcag
5401 ggtttggttt ttgtcgcgat cggcgcgctc cttggccgcg atgtttagct gcacgtattc
5461 gcgcgcaacg caccgccatt cgggaaagac ggtggtgcgc tcgtcgggca ccaggtgcac
5521 gcgccaaccg cggttgtgca gggtgacaag gtcaacgctg gtggctacct ctccgcgtag
5581 gcgctcgttg gtccagcaga ggcggccgcc cttgcgcgag cagaatggcg gtaggggtc
5641 tagctgcgtc tcgtccgggg ggtctgcgtc cacggtaaag acccccgggca gcaggcgcgc
5701 gtcgaagtag tctatcttgc atccttgcaa gtctagcgcc tgctgccatg cgcgggcggc
5761 aagcgcgcgc tcgtatgcgt tgagtggggg acccccatggc atgggtggg tgagcgcgga
5821 ggcgtacatg ccgcaaatgt cgtaaacgta gaggggctct ctgagtattc caagatatgt
5881 agggtagcat cttccaccgc ggatgctggc gcgcacgtaa tcgtatagtt cgtgcgaggg
5941 agcgaggagg tcgggaccga ggttgctacg ggcgggctgc tctgctcgga agactatctg
6001 cctgaagatg gcatgtgagt tggatgatat ggttggacgc tggaagacgt tgaagctggc
6061 gtctgtgaga cctaccgcgt cacgcacgaa ggaggcgtag gagtcgcgca gcttgttgac
6121 cagctcggcg gtgacctgca cgtctagggc gcagtagtcc agggtttcct tgatgatgtc
6181 atacttatcc tgtccctttt ttttccacag ctcgcggttg aggacaaaact cttcgcggtc
6241 tttccagtac tcttggatcg gaaacccgtc ggcctccgaa cggtaagagc ctagcatgta
6301 gaactggttg acggcctggt aggcgcagca tcccttttct acgggtagcg cgtatgcctg
```

Figure 6C.

```
6361 cgcggccttc cggcatgacc agcatgaagg gcacgagctg cttcccaaag gcccccatcc
6421 aagtataggt ctctacatcg taggtgacaa agagacgctc ggtgcgagga tgcgagccga
6481 tcgggaagaa ctggatctcc cgccaccaat tggaggagtg gctattgatg tggtgaaagt
6541 agaagtccct gcgacgggcc gaacactcgt gctggctttt gtaaaaacgt gcgcagtact
6601 ggcagcggtg cacgggctgt acatcctgca cgaggttgac ctgacgaccg cgcacaagga
6661 agcagagtgg gaatttgagc ccctcgcctg gcgggttttgg ctggtggtct tctacttcgg
6721 ctgcttgtcc ttgaccgtct ggctgctcga ggggagttac ggtggatcgg accaccacgc
6781 cgcgcgagcc caaagtccag atgtccgcgc gcggcggtcg gagcttgatg acaacatcgc
6841 gcagatggga gctgtccatg gtctggagct cccgcggcgt caggtcaggc gggagctcct
6901 gcaggtttac ctcgcataga cgggtcaggg cgcgggctag atccaggtga tacctaattt
6961 ccaggggctg gttggtggcg gcgtcgatgg cttgcaagag gccgcatccc cgcggcgcga
7021 ctacggtacc gcgcggcggg cggtgggccg cgggggtgtc cttggatgat gcatctaaaa
7081 gcggtgacgc gggcgagccc ccggaggtag ggggggctcc ggacccgccg ggagagggg
7141 caggggcacg tcggcgccgc gcgcgggcag gagctggtgc tgcgcgcgta ggttgctggc
7201 gaacgcgacg acgcggcggt tgatctcctg aatctggcgc ctctgcgtga agacgacggg
7261 cccggtgagc ttgagcctga aagagagttc gacagaatca atttcggtgt cgttgacggc
7321 ggcctggcgc aaaatctcct gcacgtctcc tgagttgtct tgataggcga tctcggccat
7381 gaactgctcg atctcttcct cctggagatc tccgcgtccg gctcgctcca cggtggcggc
7441 gaggtcgttg gaaatgcggg ccatgagctg cgagaaggcg ttgaggcctc cctcgttcca
7501 gacgcggctg tagaccacgc ccccttcggc atcgcgggcg cgcatgacca cctcgcgag
7561 attgagctcc acgtgccggg cgaagacggc gtagtttcgc aggcgctgaa agagtagtt
7621 gagggtggtg gcggtgtgtt ctgccacgaa gaagtacata acccagcgtc gcaacgtgga
7681 ttcgttgata tcccccaagg cctcaaggcg ctccatggcc tcgtagaagt ccacggcgaa
7741 gttgaaaaac tgggagttgc gcgccgacac ggttaactcc tcctccagaa gacggatgag
7801 ctcggcgaca gtgtcgcgca cctcgcgctc aaaggctaca ggggcctctt cttcttcttc
7861 aatctcctct tccataaggg cctcccttc ttcttcttct ggcggcggtg ggggaggggg
7921 gacacggcgg cgacgacggc gcaccgggag gcggtcgaca aagcgctcga tcatctcccc
7981 gcggcgacgg cgcatggtct cggtgacggc gcggccgttc tcgcgggggc gcagttggaa
8041 gacgccgccc gtcatgtccc ggttatgggt tggcggggg ctgccatgcg gcagggatac
8101 ggcgctaacg atgcatctca acaattgttg tgtaggtact ccgccgccga gggacctgag
8161 cgagtccgca tcgaccggat cggaaaacct ctcgagaaag gcgtctaacc agtcacagtc
8221 gcaaggtagg ctgagcaccg tggcgggcgg cagcgggcgg cggtcgggt tgtttctggc
8281 ggaggtgctg ctgatgatgt aattaaagta ggcggtcttg agacggcgga tggtcgacag
8341 aagcaccatg tccttgggtc cggcctgctg aatgcgcagg cggtcggcca tgccccaggc
8401 ttcgttttga catcggcgca ggtctttgta gtagtcttgc atgagccttt ctaccggcac
8461 ttcttcttct ccttcctctt gtcctgcatc tcttgcatct atcgctgcgg cggcggcgga
8521 gtttggccgt aggtggcgcc ctcttcctcc catgcgtgtg accccgaagc ccctcatcgg
8581 ctgaagcagg gctaggtcgg cgacaacgcg ctcggctaat atggcctgct gcacctgcgt
8641 gagggtagac tggaagtcat ccatgtccac aaagcggtgg tatgcgcccg tgttgatggt
8701 gtaagtgcag ttggccataa cggaccagtt aacggtctgg tgacccggct gcgagagctc
8761 ggtgtacctg agacgcgagt aagccctcga gtcaaatacg tagtcgttgc aagtccgcac
8821 caggtactgg tatcccacca aaagtgcgg cggcggctgg cggtagaggg gccagcgtag
8881 ggtggccggg gctccgggg cgagatcttc aacataagg cgatgatatc cgtagatgta
8941 cctggacatc caggtgatgc cggcggcgt ggtggaggcg cgcggaaagt cgcggacgcg
9001 gttccagatg ttgcgcagcg gcaaaaagtg ctccatggtc gggacgctct ggccggtcag
9061 gcgcgcgcaa tcgttgacgc tctagaccgt gcaaaggag agcctgtaag cgggcactct
9121 tccgtggtct ggtggataaa ttcgcaaggg tatcatgcg gacgaccggg gttcgagccc
9181 cgtatccggc cgtccgccgt gatccatgcg gttaccgccc gcgtgtcgaa cccaggtgtg
9241 cgacgtcaga caacgggga gtgctccttt tggcttcctt ccaggcgcgg cggctgctgc
9301 gctagctttt ttggccactg gccgcgcgca gcgtaagcgg ttaggctgga aagcgaaagc
9361 attaagtggc tcgctccctg tagccggagg gttattttcc aagggttgag tcgcgggacc
9421 cccggttcga gtctcggacc ggccggactg cggcgaacgg gggtttgcct ccccgtcatg
9481 caagaccccg cttgcaaatt cctccggaaa cagggacgag cccctttttt gcttttccca
```

Figure 6D.

```
 9541 gatgcatccg gtgctgcggc agatgcgccc ccctcctcag cagcggcaag agcaagagca
 9601 gcggcagaca tgcagggcac cctccctcc tcctaccgcg tcaggagggg cgacatccgc
 9661 ggttgacgcg gcagcagatg gtgattacga accccgcgg cgccgggccc ggcactacct
 9721 ggacttggag gagggcgagg gcctggcgcg gctaggagcg ccctctcctg agcggtaccc
 9781 aagggtgcag ctgaagcgtg atacgcgtga ggcgtacgtg ccgcggcaga acctgtttcg
 9841 cgaccgcgag ggagaggagc ccgaggagat gcgggatcga aagttccacg cagggcgcga
 9901 gctgcggcat ggcctgaatc gcgagcggtt gctgcgcgag gaggactttg agcccgacgc
 9961 gcgaaccggg attagtcccg cgcgcgcaca cgtggcggcc gccgacctgg taaccgcata
10021 cgagcagacg gtgaaccagg agattaactt tcaaaaaagc tttaacaacc acgtgcgtac
10081 gcttgtggcg cgcgaggagg tggctatagg actgatgcat ctgtgggact ttgtaagcgc
10141 gctggagcaa acccaaata gcaagccgct catggcgcag ctgttcctta tagtgcagca
10201 cagcagggac aacgaggcat tcagggatgc gctgctaaac atagtagagc ccgagggccg
10261 ctggctgctc gatttgataa acatcctgca gagcatagtg gtgcaggagc gcagcttgag
10321 cctggctgac aaggtggccg ccatcaacta ttccatgctt agcctgggca agttttacgc
10381 ccgcaagata taccataccc cttacgttcc catagacaag gaggtaaaga tcgaggggtt
10441 ctacatgcgc atggcgctga aggtgcttac cttgagcgac gacctgggcg tttatcgcaa
10501 cgagcgcatc cacaaggccg tgagcgtgag ccggcggcgc gagctcagcg accgcgagct
10561 gatgcacagc ctgcaaaggg ccctggctgg cacgggcagc ggcgatagag aggccgagtc
10621 ctactttgac gcgggcgctg acctgcgctg gccccaagc cgacgcgccc tggaggcagc
10681 tggggccgga cctgggctgg cggtggcacc cgcgcgcgct ggcaacgtcg gcggcgtgga
10741 ggaatatgac gaggacgatg agtacgagcc agaggacggc gagtactaag cggtgatgtt
10801 tctgatcaga tgatgcaaga cgcaacggac ccggcggtgc gggcggcgct gcagagccag
10861 ccgtccggcc ttaactccac ggacgactgg cgccaggtca tggaccgcat catgtcgctg
10921 actgcgcgca atcctgacgc gttccggcag cagccgcagg ccaaccggct ctccgcaatt
10981 ctggaagcgg tggtcccggc gcgcgcaaac cccacgcacg agaaggtgct ggcgatcgta
11041 aacgcgctgg ccgaaaacag ggccatccgg cccgacgagg ccggcctggt ctacgacgcg
11101 ctgcttcagc gcgtggctcg ttacaacagc ggcaacgtgc agaccaacct ggaccggctg
11161 gtgggggatg tgcgcgaggc cgtggcgcag cgtgagcgcg cgcagcagca gggcaacctg
11221 ggctccatgg ttgcactaaa cgccttcctg agtacacagc ccgccaacgt gccgcgggga
11281 caggaggact acaccaactt tgtgagcgca ctgcggctaa tggtgactga gacaccgcaa
11341 agtgaggtgt accagtctgg gccagactat tttttccaga ccagtagaca aggcctgcag
11401 accgtaaacc tgagccaggc tttcaaaaac ttgcaggggc tgtgggggt gcgggctccc
11461 acaggcgacc gcgcgaccgt gtctagcttg ctgacgccca actcgcgcct gttgctgctg
11521 ctaatagcgc ccttcacgga cagtggcagc gtgtcccggg acacatacct aggtcacttg
11581 ctgacactgt accgcgaggc cataggtcag gcgcatgtgg acgagcatac tttccaggag
11641 attacaagtg tcagccgcgc gctggggcag gaggacacgg gcagcctgga ggcaaccta
11701 aactacctgc tgaccaaccg gcggcagaag atcccctcgt tgcacagttt aaacagcgag
11761 gaggagcgca ttttgcgcta cgtgcagcag agcgtgagcc ttaacctgat gcgcgacggg
11821 gtaacgccca gcgtggcgct ggacatgacc gcgcgcaaca tggaaccggg catgtatgcc
11881 tcaaaccggc cgtttatcaa ccgcctaatg gactacttgc atcgcgcggc cgccgtgaac
11941 cccgagtatt tcaccaatgc catcttgaac ccgcactggc taccgccccc tggtttctac
12001 accggggggat tcgaggtgcc cgagggtaac gatggattcc tctgggacga catagacgac
12061 agcgtgtttt ccccgcaacc gcagaccctg ctagagttgc aacagcgcga gcaggcagag
12121 gcggcgctgc gaaaggaaag cttccgcagg ccaagcagct tgtccgatct aggcgctgcg
12181 gccccgcggt cagatgctag tagcccattt ccaagcttga tagggtctct taccagcact
12241 cgcaccaccc gcccgcgcct gctgggcgag gaggagtacc taaacaactc gctgctgcag
12301 ccgcagcgcg aaaaaaacct gcctccggca tttcccaaca cgggataga gagcctagtg
12361 gacaagatga gtagatggaa gacgtacgcg caggagcaca gggacgtgcc aggcccgcgc
12421 ccgcccaccc gtcgtcaaag gcacgaccgt cagcggggtc tggtgtggga ggacgatgac
12481 tcggcagacg acagcagcgt cctggattg ggaggagtg gcaacccgtt tgcgcacctt
12541 cgccccaggc tggggagaat gttttaaaaa aaaaaagca tgatgcaaaa taaaaaactc
12601 accaaggcca tggcaccgag cgttggtttt cttgtattcc ccttagtatg cggcgcgcgg
12661 cgatgtatga ggaaggtcct cctccctcct acgagagtgt ggtgagcgcg cgccagtgg
```

Figure 6E.

```
12721 cggcggcgct gggttctccc ttcgatgctc ccctggaccc gccgtttgtg cctccgcggt
12781 acctgcggcc taccgggggg agaaacagca tccgttactc tgagttggca ccccctattcg
12841 acaccacccg tgtgtacctg gtggacaaca agtcaacgga tgtggcatcc ctgaactacc
12901 agaacgacca cagcaacttt ctgaccacgg tcattcaaaa caatgactac agcccgggg
12961 aggcaagcac acagaccatc aatcttgacg accggtcgca ctggggcggc gacctgaaaa
13021 ccatcctgca taccaacatg ccaaatgtga acgagttcat gtttaccaat aagtttaagg
13081 cgcgggtgat ggtgtcgcgc ttgcctacta aggacaatca ggtggagctg aaatacgagt
13141 gggtggagtt cacgctgccc gagggcaact actccgagac catgaccata gaccttatga
13201 acaacgcgat cgtggagcac tacttgaaag tgggcagaca gaacggggtt ctggaaagcg
13261 acatcggggt aaagtttgac acccgcaact tcagactggg gtttgacccc gtcactggtc
13321 ttgtcatgcc tggggtatat acaaacgaag ccttccatcc agacatcatt ttgctgccag
13381 gatgcgggt ggacttcacc cacagccgcc tgagcaactt gttgggcatc cgcaagcggc
13441 aaccccttcca ggagggcttt aggatcacct acgatgatct ggagggtggt aacattcccg
13501 cactgttgga tgtggacgcc taccaggcga gcttgaaaga tgacaccgaa cagggcgggg
13561 gtggcgcagg cggcagcaac agcagtggca gcggcgcgga agagaactcc aacgcggcag
13621 ccgcggcaat gcagccggtg gaggacatga acgatcatgc cattcgcggc gacacctttg
13681 ccacacgggc tgaggagaag cgcgctgagg ccgaagcagc ggccgaagct gccgcccccg
13741 ctgcgcaacc cgaggtcgag aagcctcaga agaaaccggt gatcaaaccc ctgacagagg
13801 acagcaagaa acgcagttac aacctaataa gcaatgacag caccttcacc cagtaccgca
13861 gctggtacct tgcatacaac tacggcgacc ctcagaccgg aatccgctca tggaccctgc
13921 tttgcactcc tgacgtaacc tgcggctcgg agcaggtcta ctggtcgttg ccagacatga
13981 tgcaagaccc cgtgaccttc cgctccacgc gccagatcag caactttccg gtggtgggcg
14041 ccgagctgtt gcccgtgcac tccaagagct tctacaacga ccaggccgtc tactcccaac
14101 tcatccgcca gtttacctct ctgacccacg tgttcaatcg ctttcccgag aaccagattt
14161 tggcgcgccc gccagccccc accatcacca ccgtcagtga aaacgttcct gctctcacag
14221 atcacgggac gctaccgctg cgcaacagca tcggaggagt ccagcgagtg accattactg
14281 acgccagacg ccgcacctgc ccctacgttt acaaggccct gggcatagtc tcgccgcgcg
14341 tcctatcgag ccgcactttt tgagcaagca tgtccatcct tatatcgccc agcaataaca
14401 caggctgggg cctgcgcttc ccaagcaaga tgtttggcgg ggccaagaag cgctccgacc
14461 aacacccagt gcgcgtgcgc gggcactacc gcgcgccctg gggcgcgcac aaacgcggcc
14521 gcactgggcg caccaccgtc gatgacgcca tcgacgcggt ggtggaggag gcgcgcaact
14581 acacgcccac gccgccacca gtgtccacag tggacgcggc cattcagacc gtggtgcgcg
14641 gagcccggcg ctatgctaaa atgaagagac ggcggaggcg cgtagcacgt cgccaccgcc
14701 gccgacccgg cactgccgcc caacgcgcgg cggcggccct gcttaaccgc gcacgtcgca
14761 ccggccgacg ggcggccatg cgggccgctc gaaggctggc cgcgggtatt gtcactgtgc
14821 cccccaggtc caggcgacga gcggccgccg cagcagccgc ggccattagt gctatgactc
14881 agggtcgcag gggcaacgtg tattgggtgc gcgactcggt tagcggcctg cgcgtgcccg
14941 tgcgcacccg cccccgcgc aactagattg caagaaaaaa ctacttagac tcgtactgtt
15001 gtatgtatcc agcggcggcg gcgcgcaacg aagctatgtc caagcgcaaa atcaaagaag
15061 agatgctcca ggtcatcgcg ccggagatct atggcccccc gaagaaggaa gagcaggatt
15121 acaagccccg aaagctaaag cgggtcaaaa agaaaaagaa agatgatgat gatgaacttg
15181 acgacgaggt ggaactgctg cacgctaccg cgcccaggcg acgggtacag tggaaaggtc
15241 gacgcgtaaa acgtgttttg cgacccggca ccaccgtagt ctttacgccc ggtgagcgct
15301 ccaccccgcac ctacaagcgc gtgtatgatg aggtgtacgg cgacgaggac ctgcttgagc
15361 aggccaacga gcgcctcggg gagtttgcct acggaaagcg gcataaggac atgctggcgt
15421 tgccgctgga cgagggcaac ccaacaccta gcctaaagcc cgtaacactg cagcaggtgc
15481 tgcccgcgct tgcaccgtcc gaagaaaagc gcggcctaaa gcgcgagtct ggtgacttgg
15541 cacccaccgt gcagctgatg gtacccaagc gccagcgact ggaagatgtc ttggaaaaaa
15601 tgaccgtgga acctgggctg gagcccgagg tccgcgtgcg gccaatcaag caggtggcgc
15661 cgggactggg cgtgcagacc gtggacgttc agatacccac taccagtagc accagtattg
15721 ccaccgccac agagggcatg gagacacaaa cgtccccggt tgcctcagcg gtggcggatg
15781 ccgcggtgca ggcggtcgct gcggccgcgt ccaagacctc tacgaggtg caaacggacc
15841 cgtggatgtt tcgcgtttca gccccccggc gccgcgcgg ttcgaggaag tacggcgccg
```

Figure 6F.

```
15901 ccagcgcgct actgcccgaa tatgccctac atccttccat tgcgcctacc cccggctatc
15961 gtggctacac ctaccgcccc agaagacgag caactacccg acgccgaacc accactggaa
16021 cccgccgccg ccgtcgccgt cgccagcccg tgctggcccc gatttccgtg cgcagggtgg
16081 ctcgcgaagg aggcaggacc ctggtgctgc caacagcgcg ctaccacccc agcatcgttt
16141 aaaagccggt ctttgtggtt cttgcagata tggccctcac ctgccgcctc cgtttcccgg
16201 tgccgggatt ccgaggaaga atgcaccgta ggaggggcat ggccggccac ggcctgacgg
16261 gcggcatgcg tcgtgcgcac caccggcggc ggcgcgcgtc gcaccgtcgc atgcgcggcg
16321 gtatcctgcc cctccttatt ccactgatcg ccgcggcgat tggcgccgtg cccggaattg
16381 catccgtggc cttgcaggcg cagagacact gattaaaaac aagttgcatg tggaaaaatc
16441 aaaataaaaa gtctggactc tcacgctcgc ttggtcctgt aactattttg tagaatggaa
16501 gacatcaact ttgcgtctct ggccccgcga cacggctcgc gcccgttcat gggaaactgg
16561 caagatatcg gcaccagcaa tatgagcggt ggcgccttca gctgggggctc gctgtggagc
16621 ggcattaaaa atttcggttc caccgttaag aactatggca gcaaggcctg aacagcagc
16681 acaggccaga tgctgaggga taagttgaaa gagcaaaatt ccaacaaaa ggtggtagat
16741 ggcctggcct ctggcattag cggggtggtg gacctggcca accaggcagt gcaaaataag
16801 attaacagta agcttgatcc ccgccctccc gtagaggagc ctccaccggc cgtggagaca
16861 gtgtctccag aggggcgtgg cgaaaagcgt ccgcgccccg acagggaaga aactctggtg
16921 acgcaaatag acgagcctcc ctcgtacgag gaggcactaa agcaaggcct gcccaccacc
16981 cgtcccatcg cgcccatggc taccggagtg ctgggccagc acacacccgt aacgctggac
17041 ctgcctcccc ccgccgacac ccagcagaaa cctgtgctgc caggcccgac cgccgttgtt
17101 gtaacccgtc ctagccgcgc gtccctgcgc cgcgccgcca gcggtccgcg atcgttgcgg
17161 cccgtagcca gtggcaactg gcaaagcaca ctgaacagca tcgtgggtct gggggtgcaa
17221 tccctgaagc gccgacgatg cttctgaata gctaacgtgt cgtatgtgtg tcatgtatgc
17281 gtccatgtcg ccgccagagg agctgctgag ccgccgcgcg cccgctttcc aagatggcta
17341 ccccttcgat gatgccgcag tggtcttaca tgcacatctc gggccaggac gcctcggagt
17401 acctgagccc cgggctggtg cagtttgccc gcgccaccga gacgtacttc agcctgaata
17461 acaagtttag aaaccccacg gtggcgccta cgcacgacgt gaccacagac cggtcccagc
17521 gtttgacgct gcggttcatc cctgtggacc gtgaggatac tgcgtactcg tacaaggcgc
17581 ggttcaccct agctgtgggt gataaccgtg tgctggacat ggcttccacg tactttgaca
17641 tccgcggcgt gctggacagg ggccctactt ttaagcccta ctctggcact gcctacaacg
17701 ccctggctcc caagggtgcc ccaaatcctt gcgaatggga tgaagctgct actgctcttg
17761 aaataaacct agaagaagag gacgatgaca acgaagacga agtagacgag caagctgagc
17821 agcaaaaaac tcacgtattt gggcaggcgc cttattctgg tataaatatt acaaaggagg
17881 gtattcaaat aggtgtcgaa ggtcaaacac ctaaatatgc cgataaaaca tttcaacctg
17941 aacctcaaat aggagaatct cagtggtacg aaactgaaat taatcatgca gctgggagag
18001 tccttaaaaa gactacccca atgaaaccat gttacggttc atatgcaaaa cccacaaatg
18061 aaaatggagg gcaaggcatt cttgtaaagc aacaaaatgg aaagctagaa agtcaagtgg
18121 aaatgcaatt tttctcaact actgaggcga ccgcaggcaa tggtgataac ttgactccta
18181 aagtggtatt gtacagtgaa gatgtagata tagaaacccc agacactcat atttcttaca
18241 tgcccactat taaggaaggt aactacgag aactaatggg ccaacaatct atgcccaaca
18301 ggcctaatta cattgctttt agggacaatt ttattggtct aatgtattac aacagcacgg
18361 gtaatatggg tgttctggcg ggccaagcat cgcagttgaa tgctgttgta gatttgcaag
18421 acagaaacac agagctttca taccagcttt tgcttgattc cattggtgat agaaccaggt
18481 acttttctat gtggaatcag gctgttgaca gctatgatcc agatgttaga attattgaaa
18541 atcatggaac tgaagatgaa cttccaaatt actgctttcc actgggaggt gtgattaata
18601 cagagactct taccaaggta aaacctaaaa caggtcagga aatggatgg gaaaaagatg
18661 ctacagaatt ttcagataaa aatgaaataa gagttggaaa taattttgcc atggaaatca
18721 atctaaatgc caacctgtgg agaaatttcc tgtactccaa catagcgctg tatttgcccg
18781 acaagctaaa gtacagtcct tccaacgtaa aaatttctga taacccaaac acctacgact
18841 acatgaacaa gcgagtggtg gctcccgggt tagtggactg ctacattaac cttggagcac
18901 gctggtccct tgactatatg gacaacgtca acccatttaa ccaccaccgc aatgctggcc
18961 tgcgctaccg ctcaatgttg ctgggcaatg tcgctatgt gccttccac atccaggtgc
19021 ctcagaagtt ctttgccatt aaaaacctcc ttctcctgcc gggctcatac acctacgagt
```

Figure 6G.

```
19081 ggaacttcag gaaggatgtt aacatggttc tgcagagctc cctaggaaat gacctaaggg
19141 ttgacggagc cagcattaag tttgatagca tttgccttta cgccaccttc ttccccatgg
19201 cccacaacac cgcctccacg cttgaggcca tgcttagaaa cgacaccaac gaccagtcct
19261 ttaacgacta tctctccgcc gccaacatgc tctaccctat acccgccaac gctaccaacg
19321 tgcccatatc catcccctcc cgcaactggg cggctttccg cggctgggcc ttcacgcgcc
19381 ttaagactaa ggaaacccca tcactgggct cgggctacga cccttattac acctactctg
19441 gctctatacc ctacctagat ggaacctttt acctcaacca cacctttaag aaggtggcca
19501 ttacctttga ctcttctgtc agctggcctg gcaatgaccg cctgcttacc cccaacgagt
19561 ttgaaattaa gcgctcagtt gacggggagg gttacaacgt tgcccagtgt aacatgacca
19621 aagactggtt cctggtacaa atgctagcta actacaacat tggctaccag ggcttctata
19681 tcccagagag ctacaaggac cgcatgtact ccttctttag aaacttccag cccatgagcc
19741 gtcaggtggt ggatgatact aaatacaagg actaccaaca ggtgggcatc ctacaccaac
19801 acaacaactc tggatttgtt ggctaccttg cccccaccat gcgcgaagga caggcctacc
19861 ctgctaactt cccctatccg cttataggca agaccgcagt tgacagcatt acccagaaaa
19921 agtttctttg cgatcgcacc ctttggcgca tcccattctc cagtaacttt atgtccatgg
19981 gcgcactcac agacctgggc caaaaccttc tctacgccaa ctccgcccac gcgctagaca
20041 tgactttgga ggtggatccc atggacgagc ccaccttct ttatgttttg tttgaagtct
20101 ttgacgtggt ccgtgtgcac cagccgcacc gcggcgtcat cgaaaccgtg tacctgcgca
20161 cgcccttctc ggccggcaac gccacaacat aaagaagcaa gcaacatcaa caacagctgc
20221 cgccatgggc tccagtgagc aggaactgaa agccattgtc aaagatcttg gttgtgggcc
20281 atatttttg ggcgcctatg acaagcgctt tccaggcttt gtttctccac acaagctcgc
20341 ctgcgccata gtcaatacgg ccggtcgcga gactgggggc gtacactgga tggcctttgc
20401 ctggaacccg cactcaaaaa catgctacct ctttgagccc tttggctttt ctgaccagcg
20461 actcaagcag gtttaccagt ttgagtacga gtcactcctg cgccgtagcg ccattgcttc
20521 ttcccccgac cgctgtataa cgctggaaaa gtccacccaa agcgtacagg gcccaactc
20581 ggccgcctgt ggactattct gctgcatgtt tctccacgcc tttgccaact ggccccaaac
20641 tcccatggat cacaacccca ccatgaacct tattaccggg gtacccaact ccatgctcaa
20701 cagtccccag gtacagccca ccctgcgtcg caaccaggaa cagctctaca gcttcctgga
20761 gcgccactcg ccctacttcc gcagccacag tgcgcagatt aggagcgcca cttcttttg
20821 tcacttgaaa aacatgtaaa aataatgtac tagagacact ttcaataaag gcaaatgctt
20881 ttatttgtac actctcgggt gattatttac ccccaccctt gccgtctgcg ccgtttaaaa
20941 atcaaagggg ttctgccgcg catcgctatg cgccactggc agggacacgt tgcgatactg
21001 gtgtttagtg ctccacttaa actcaggcac aaccatccgc ggcagctcgg tgaagttttc
21061 actccacagg ctgcgcacca tcaccaacgc gtttagcagg tcgggcgccg atatcttgaa
21121 gtcgcagttg gggcctccgc cctgcgcgcg cgagttgcga tacacagggt tgcagcactg
21181 gaacactatc agcgccgggt ggtgcacgct ggccagcacg ctcttgtcgg agatcagatc
21241 cgcgtccagg tcctccgcgt tgctcagggc gaacggagtc aactttggta gctgccttcc
21301 caaaaagggc gcgtgcccag gctttgagtt gcactcgcac cgtagtggca tcaaaggtg
21361 accgtgcccg gtctgggcgt taggatacag cgcctgcata aaagccttga tctgcttaaa
21421 agccacctga gcctttgcgc cttcagagaa gaacatgccg caagacttgc cggaaaactg
21481 attggccgga caggccgcgt cgtgcacgca gcaccttgcg tcggtgttgg agatctgcac
21541 cacatttcgg ccccaccggt tcttcacgat cttggccttg ctagactgct ccttcagcgc
21601 gcgctgcccg ttttcgctcg tcacatccat ttcaatcacg tgctccttat ttatcataat
21661 gcttccgtgt agacacttaa gctcgccttc gatctcagcg cagcggtgca gccacaacgc
21721 gcagcccgtg ggctcgtgat gcttgtaggt cacctctgca aacgactgca ggtacgcctg
21781 caggaatcgc cccatcatcg tcacaaaggt cttgttgctg gtgaaggtca gctgcaaccc
21841 gcggtgctcc tcgttcagcc aggtcttgca tacggccgcc agagcttcca cttggtcagg
21901 cagtagtttg aagttcgcct ttagatcgtt atccacgtgg tacttgtcca tcagcgcgcg
21961 cgcagcctcc atgcccttct cccacgcaga cacgatcggc acactcagcg ggttcatcac
22021 cgtaatttca ctttccgctt cgctgggctc ttcctcttcc tcttgcgtcc gcataccacg
22081 cgccactggg tcgtcttcat tcagccgccg cactgtgcgc ttacctcctt tgccatgctt
22141 gattagcacc ggtgggttgc tgaaacccac catttgtagc gccacatctt ctctttcttc
22201 ctcgctgtcc acgattacct ctggtgatgg cgggcgctcg ggcttgggag aagggcgctt
```

Figure 6H.

```
22261 cttttcttc ttgggcgcaa tggccaaatc cgccgccgag gtcgatggcc gcgggctggg
22321 tgtgcgcggc accagcgcgt cttgtgatga gtcttcctcg tcctcggact cgatacgccg
22381 cctcatccgc ttttttgggg gcgcccgggg aggcggcggc gacggggacg gggacgacac
22441 gtcctccatg gttgggggac gtcgcgccgc accgcgtccg cgctcggggg tggtttcgcg
22501 ctgctcctct tcccgactgg ccatttcctt ctcctatagg cagaaaaaga tcatggagtc
22561 agtcgagaag aaggacagcc taaccgcccc ctctgagttc gccaccaccg cctccaccga
22621 tgccgccaac gcgcctacca ccttccccgt cgaggcaccc ccgcttgagg aggaggaagt
22681 gattatcgag caggacccag gttttgtaag cgaagacgac gaggaccgct cagtaccaac
22741 agaggataaa aagcaagacc aggacaacgc agaggcaaac gaggaacaag tcgggcgggg
22801 ggacgaaagg catggcgact acctagatgt gggagacgac gtgctgttga agcatctgca
22861 gcgccagtgc gccattatct gcgacgcgtt gcaagagcgc agcgatgtgc ccctcgccat
22921 agcggatgtc agccttgcct acgaacgcca cctattctca ccgcgcgtac cccccaaacg
22981 ccaagaaaac ggcacatgcg agcccaaccc gcgcctcaac ttctacccccg tatttgccgt
23041 gccagaggtg cttgccacct atcacatctt tttccaaaac tgcaagatac ccctatcctg
23101 ccgtgccaac cgcagccgag cggacaagca gctggccttg cggcagggcg ctgtcatacc
23161 tgatatcgcc tcgctcaacg aagtgccaaa aatctttgag ggtcttggac gcgacgagaa
23221 gcgcgcggca aacgctctgc aacaggaaaa cagcgaaaat gaaagtcact ctggagtgtt
23281 ggtggaactc gagggtgaca acgcgcgcct agccgtacta aaacgcagca tcgaggtcac
23341 ccactttgcc tacccggcac ttaacctacc ccccaaggtc atgagcacag tcatgagtga
23401 gctgatcgtg cgccgtgcgc agcccctgga gagggatgca aatttgcaag aacaaacaga
23461 ggagggccta cccgcagttg gcgacgagca gctagcgcgc tggcttcaaa cgcgcgagcc
23521 tgccgacttg gaggagcgac gcaaactaat gatggccgca gtgctcgtta ccgtggagct
23581 tgagtgcatg cagcggttct ttgctgaccc ggagatgcag cgcaagctag aggaaacatt
23641 gcactacacc tttcgacagg gctacgtacg ccaggcctgc aagatctcca acgtggagct
23701 ctgcaacctg gtctcctacc ttggaatttt gcacgaaaac cgccttgggc aaaacgtgct
23761 tcattccacg ctcaagggcg aggcgcgccc cgactacgtc cgcgactgcg tttacttatt
23821 tctatgctac acctggcaga cggccatggg cgtttggcag cagtgcttgg aggagtgcaa
23881 cctcaaggag ctgcagaaac tgctaaagca aaacttgaag gacctatgga cggccttcaa
23941 cgagcgctcc gtggccgcgc acctggcgga catcattttc cccgaacgcc tgcttaaaac
24001 cctgcaacag ggtctgccag acttcaccag tcaaagcatg ttgcagaact ttaggaactt
24061 tatcctagag cgctcaggaa tcttgcccgc cacctgctgt gcacttccta gcgactttgt
24121 gccattaag taccgcgaat gccctccgcc gctttgggggc cactgctacc ttctgcagct
24181 agccaactac cttgcctacc actctgacat aatggaagac gtgagcggtg acggtctact
24241 ggagtgtcac tgtcgctgca acctatgcac cccgcaccgc tccctggttt gcaattcgca
24301 gctgcttaac gaaagtcaaa ttatcggtac ctttgagctg cagggtccct cgcctgacga
24361 aaagtccgcg gctccggggt tgaaactcac tccggggctg tggacgtcgg cttaccttcg
24421 caaatttgta cctgaggact accacgccca cgagattagg ttctacgaag accaatcccg
24481 cccgcctaat gcggagctta ccgcctgcgt cattacccag ggccacattc ttggccaatt
24541 gcaagccatc aacaaagccc gccaagagtt tctgctacga aagggacggg gggtttactt
24601 ggaccccccag tccggcgagg agctcaaccc aatccccccg ccgccgcagc cctatcagca
24661 gcagccgcgg gcccttgctt cccaggatgg cacccaaaaa gaagctgcag ctgccgccgc
24721 cacccacgga cgaggaggaa tactgggaca gtcaggcaga ggaggttttg gacgaggagg
24781 aggaggacat gatggaagac tgggagagcc tagacgagga agcttccgag gtcgaagagg
24841 tgtcagacga aacaccgtca ccctcggtcg cattcccctc gccggcgccc cagaaatcgg
24901 caaccggttc cagcatggct acaacctccg ctcctcaggc gccgccggca ctgcccgttc
24961 gccgacccaa ccgtagatgg acaccactg gaaccagggc cggtaagtcc aagcagccgc
25021 cgccgttagc ccaagagcaa caacagcgcc aaggctaccg ctcatgcgc gggcacaaga
25081 acgccatagt tgcttgcttg caagactgtg ggggcaacat ctccttcgcc cgccgctttc
25141 ttctctacca tcacggcgtg gccttccccc gtaacatcct gcattactac cgtcatctct
25201 acagcccata ctgcaccggc ggcagcggca gcaacagcag cggccacaca gaagcaaagg
25261 cgaccggata gcaagactct gacaaagccc aagaaatcca cagcggcggc agcagcagga
25321 ggaggagcgc tgcgtctggc gcccaacgaa cccgtatcga cccgcgagct tagaaacagg
25381 attttccca ctctgtatgc tatatttcaa cagagcaggg gccaagaaca agagctgaaa
```

Figure 6I.

```
25441 ataaaaaaca ggtctctgcg atccctcacc cgcagctgcc tgtatcacaa aagcgaagat
25501 cagcttcggc gcacgctgga agacgcggag gctctcttca gtaaatactg cgcgctgact
25561 cttaaggact agtttcgcgc cctttctcaa atttaagcgc gaaaactacg tcatctccag
25621 cggccacacc cggcgccagc acctgttgtc agcgccatta tgagcaagga aattcccacg
25681 ccctacatgt ggagttacca gccacaaatg ggacttgcgg ctggagctgc ccaagactac
25741 tcaacccgaa taaactacat gagcgcggga ccccacatga tatcccgggt caacggaata
25801 cgcgccacc gaaaccgaat tcctctggaa caggcggcta ttaccaccac acctcgtaat
25861 aaccttaatc cccgtagttg gcccgctgcc ctggtgtacc aggaaagtcc cgctcccacc
25921 actgtggtac ttcccagaga cgcccaggcc gaagttcaga tgactaactc aggggcgcag
25981 cttgcgggcg gctttcgtca cagggtgcgg tcgcccgggc agggtataac tcacctgaca
26041 atcagagggc gaggtattca gctcaacgac gagtcggtga gctcctcgct tggtctccgt
26101 ccggacggga catttcagat cggcggcgcc ggccgctctt cattcacgcc tcgtcaggca
26161 atcctaactc tgcagacctc gtcctctgag ccgcgctctg gaggcattgg aactctgcaa
26221 tttattgagg agtttgtgcc atcggtctac tttaacccct tctcgggacc tcccggccac
26281 tatccggatc aatttattcc taactttgac gcggtaaagg actcggcgga cggctacgac
26341 tgaatgttaa gtggagaggc agagcaactg cgcctgaaac acctggtcca ctgtcgccgc
26401 cacaagtgct tgcccgcga ctccggtgag ttttgctact ttgaattgcc cgaggatcat
26461 atcgagggcc cggcgcacgg cgtccggctt accgcccagg gagagcttgc ccgtagcctg
26521 attcgggagt ttacccagcg ccccctgcta gttgagcggg acaggggacc ctgtgttctc
26581 actgtgattt gcaactgtcc taaccctgga ttacatcaag atctttgttg ccatctctgt
26641 gctgagtata ataaatacag aaattaaaat atactggggc tcctatcgcc atcctgtaaa
26701 cgccaccgtc ttcacccgcc caagcaaacc aaggcgaacc ttacctggta ctttttaacat
26761 ctctccctct gtgatttaca acagtttcaa cccagacgga gtgagtctac gagagaacct
26821 ctccgagctc agctactcca tcagaaaaaa caccacccctc cttacctgcc gggaacgtac
26881 gagtgcgtca ccggccgctg caccacacct accgcctgac cgtaaaccag acttttccg
26941 gacagacctc aataactctg tttaccagaa caggaggtga gcttagaaaa cccttagggt
27001 attaggccaa aggcgcagct actgtggggt ttatgaacaa ttcaagcaac tctacgggct
27061 attctaattc aggtttctct agtagaaatg gacggaatta ttacagagca gcgcctgcta
27121 gaaagacgca gggcagcggc cgagcaacag cgcatgaatc aagagctcca agacatggtt
27181 aacttgcacc agtgcaaaag gggtatcttt tgtctggtaa agcaggccaa agtcacctac
27241 gacagtaata ccaccggaca ccgccttagc tacaagttgc caaccaagcg tcagaaattg
27301 gtggtcatgg tgggagaaaa gcccattacc ataactcagc actcggtaga aaccgaaggc
27361 tgcattcact caccttgtca aggacctgag gatctctgca cccttattaa gaccctgtgc
27421 ggtctcaaag atcttattcc ctttaactaa taaaaaaaaa taataaagca tcacttactt
27481 aaaatcagtt agcaaatttc tgtccagttt attcagcagc acctccttgc cctcctccca
27541 gctctggtat tgcagcttcc tcctggctgc aaactttctc cacaatctaa atggaatgtc
27601 agtttcctcc tgttcctgtc catccgcacc cactatcttc atgttgttgc agatgaagcg
27661 cgcaagaccg tctgaagata ccttcaaccc cgtgtatcca tatgacacgg aaaccggtcc
27721 tccaactgtg ccttttctta ctcctccctt tgtatccccc aatgggtttc aagagagtcc
27781 ccctggggta ctctctttgc gcctatccga acctctagtt acctccaatg gcatgcttgc
27841 gctcaaaatg ggcaacggcc tctctctgga cgaggccggc aaccttacct cccaaaatgt
27901 aaccactgtg agcccacctc tcaaaaaaac caagtcaaac ataaacctgg aaatatctgc
27961 acccctcaca gttacctcag aagccctaac tgtggctgcc gccgcacctc taatggtcgc
28021 gggcaacaca ctcaccatgc aatcacaggc cccgctaacc gtgcacgact ccaaacttag
28081 cattgccacc caaggaccc tcacagtgtc agaaggaaag ctagccctgc aaacatcagg
28141 ccccctcacc accaccgata gcagtaccct tactatcact gcctcacccc tctaactac
28201 tgccactggt agcttgggca ttgacttgaa agagcccatt tatacacaaa atggaaaact
28261 aggactaaag tacggggctc ctttgcatgt aacagacgac ctaaacactt tgaccgtagc
28321 aactggtcca ggtgtgacta ttaataatac ttccttgcaa actaaagtta ctggagcctt
28381 gggttttgat tcacaaggca atatgcaact taatgtagca ggaggactaa ggattgattc
28441 tcaaaacaga cgccttatac ttgatgttag ttatccgttt gatgctcaaa accaactaaa
28501 tctaagacta ggacagggcc tcttttttat aaactcagcc cacaacttgg atattaacta
28561 caacaaaggc ctttacttgt ttacagcttc aaacaattcc aaaaagcttg aggttaacct
```

Figure 6J.

```
28621 aagcactgcc aaggggttga tgtttgacgc tacagccata gccattaatg caggagatgg
28681 gcttgaattt ggttcaccta atgcaccaaa cacaaatccc ctcaaaacaa aaattggcca
28741 tggcctagaa tttgattcaa acaaggctat ggttcctaaa ctaggaactg gccttagttt
28801 tgacagcaca ggtgccatta cagtaggaaa caaaaataat gataagctaa ctttgtggac
28861 cacaccagct ccatctccta actgtagact aaatgcagag aaagatgcta aactcacttt
28921 ggtcttaaca aaatgtggca gtcaaatact tgctacagtt tcagttttgg ctgttaaagg
28981 cagtttggct ccaatatctg aacagttca aagtgctcat cttattataa gatttgacga
29041 aaatggagtg ctactaaaca attccttcct ggacccagaa tattggaact ttagaaatgg
29101 agatcttact gaaggcacag cctatacaaa cgctgttgga tttatgccta acctatcagc
29161 ttatccaaaa tctcacggta aaactgccaa aagtaacatt gtcagtcaag tttacttaaa
29221 cggagacaaa actaaacctg taacactaac cattacacta aacggtacac aggaaacagg
29281 agacacaact ccaagtgcat actctatgtc attttcatgg gactggtctg ccacaacta
29341 cattaatgaa atatttgcca catcctctta cacttttca tacattgccc aagaataaag
29401 aatcgtttgt gttatgtttc aacgtgttta tttttcaatt gcagaaaatt tcaagtcatt
29461 tttcattcag tagtatagcc ccaccaccac atagcttata cagatcaccg tacttaatc
29521 aaactcacag aaccctagta ttcaacctgc cacctccctc ccaacacaca gagtacacag
29581 tcctttctcc ccggctggcc ttaaaaagca tcatatcatg ggtaacagac atattcttag
29641 gtgttatatt ccacacggtt tcctgtcgag ccaaacgctc atcagtgata ttaataaact
29701 ccccgggcag ctcacttaag ttcatgtcgc tgtccagctg ctgagccaca ggctgctgtc
29761 caacttgcgg ttgcttaacg ggcggcgaag gagaagtcca cgcctacatg ggggtagagt
29821 cataatcgtg catcaggata gggcggtggt gctgcagcag cgcgcgaata aactgctgcc
29881 gccgccgctc cgtcctgcag gaatacaaca tggcagtggt ctcctcagcg atgattcgca
29941 ccgccgcag cataaggcgc cttgtcctcc gggcacagca gcgcaccctg atctcactta
30001 aatcagcaca gtaactgcag cacagccacca caatattgtt caaaatccca cagtgcaagg
30061 cgctgtatcc aaagctcatg gcggggacca cagaacccac gtggccatca taccacaagc
30121 gcaggtagat taagtggcga ccctcatca acacgtggga cataaacatt acctcttttg
30181 gcatgttgta attcaccacc tcccggtacc atataaacct ctgattaaac atggcgccat
30241 ccaccaccat cctaaaccag ctggccaaaa cctgcccgcc ggctatacac tgcagggaac
30301 cgggactgga acaatgacag tggagagccc aggactcgta accatggatc atcatgctcg
30361 tcatgatatc aatgttggca caacacaggc acacgtgcat acacttcctc aggattacaa
30421 gctcctcccg cgttagaacc atatcccagg gaacaaccca ttcctgaatc agcgtaaatc
30481 ccacactgca gggaagacct cgcacgtaac tcacgttgtg cattgtcaaa gtgttacatt
30541 cgggcagcag cggatgatcc tccagtatgg tagcgcgggt ttctgtctca aaaggaggta
30601 gacgatccct actgtacgga gtgcgccgag acaaccgaga tcgtgttggt cgtagtgtca
30661 tgccaaatgg aacgccggac gtagtcatat ttcctgaagc aaaaccaggt gcgggcgtga
30721 caaacagatc tgcgtctccg gtctcgccgc ttagatcgct ctgtgtagta gttgtagtat
30781 atccactctc tcaaagcatc caggcgcccc ctggcttcgg gttctatgta aactccttca
30841 tgcgccgctg ccctgataac atccaccacc gcagaataag ccacacccag ccaacctaca
30901 cattcgttct gcgagtcaca cacgggagga gcgggaagag ctggaagaac catgtttttt
30961 tttttattcc aaaagattat ccaaaacctc aaaatgaaga tctattaagt gaacgcgctc
31021 ccctccggtg gcgtggtcaa actctacagc caaagaacag ataatggcat ttgtaagatg
31081 ttgcacaatg gcttccaaaa ggcaaacggc cctcacgtcc aagtggacgt aaaggctaaa
31141 cccttcaggg tgaatctcct ctataaacat tccagcacct tcaaccatgc ccaaataatt
31201 ctcatctcgc caccttctca atatatctct aagcaaatcc gaatattaa gtccggccat
31261 tgtaaaaatc tgctccagag cgccctccac cttcagcctc aagcagcgaa tcatgattgc
31321 aaaaattcag gttcctcaca gacctgtata agattcaaaa gcggaacatt aacaaaata
31381 ccgcgatccc gtaggtccct tcgcagggcc agctgaacat aatcgtgcag gtctgcacgg
31441 accagcgcgg ccacttcccc gccaggaacc atgacaaaag aacccacact gattatgaca
31501 cgcatactcg gagctatgct aaccagcgta gccccgatgt aagcttgttg catggcggc
31561 gatataaaat gcaaggtgct gctcaaaaaa tcaggcaaag cctcgcgcaa aaagaaagc
31621 acatcgtagt catgctcatg cagataaagg caggtaagct ccggaaccac cacagaaaaa
31681 gacaccattt ttctctcaaa catgtctgcg ggtttctgca taaacacaaa ataaaataac
31741 aaaaaaacat ttaaacatta gaagcctgtc ttacaacagg aaaaacaacc cttataagca
```

Figure 6K.

```
31801 taagacggac tacggccatg ccggcgtgac cgtaaaaaaa ctggtcaccg tgattaaaaa
31861 gcaccaccga cagctcctcg gtcatgtccg gagtcataat gtaagactcg gtaaacacat
31921 caggttgatt cacatcggtc agtgctaaaa agcgaccgaa atagcccggg ggaatacata
31981 cccgcaggcg tagagacaac attacagccc ccataggagg tataacaaaa ttaataggag
32041 agaaaaacac ataaacacct gaaaaaccct cctgcctagg caaaatagca ccctcccgct
32101 ccagaacaac atacagcgct tccacagcgg cagccataac agtcagcctt accagtaaaa
32161 aagaaaacct attaaaaaaa caccactcga cacggcacca gctcaatcag tcacagtgta
32221 aaaagggcc aagtgcagag cgagtatata taggactaaa aaatgacgta acggttaaag
32281 tccacaaaaa acacccagaa aaccgcacgc gaacctacgc ccagaaacga aagccaaaaa
32341 acccacaact tcctcaaatc gtcacttccg ttttcccacg ttacgtcact tcccattta
32401 agaaaactac aattcccaac acatacaagt tactccgccc taaaacctac gtcacccgcc
32461 ccgttcccac gccccgcgcc acgtcacaaa ctccaccccc tcattatcat attggcttca
32521 atccaaaata aggtatatta ttgatgatgt taat
```

Figure 7. Comparison in vitro of interferon alpha 2b expression from IACB and T8BF. A549 cells 72 post infection.
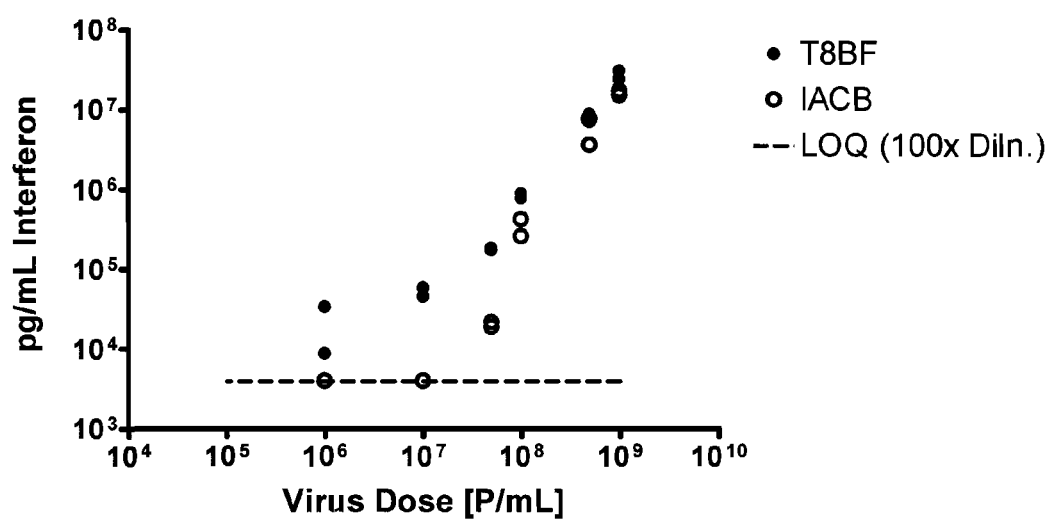

Figure 8. Comparison in vivo of interferon alpha 2b expression from IACB and T8BF in rat urine at both initial dose and 62 day redose. In this example, T8BF (circles) and IACB (squares) data is shown as mean ± SE for two experiments where n=5 (filled) and n=6 (open).
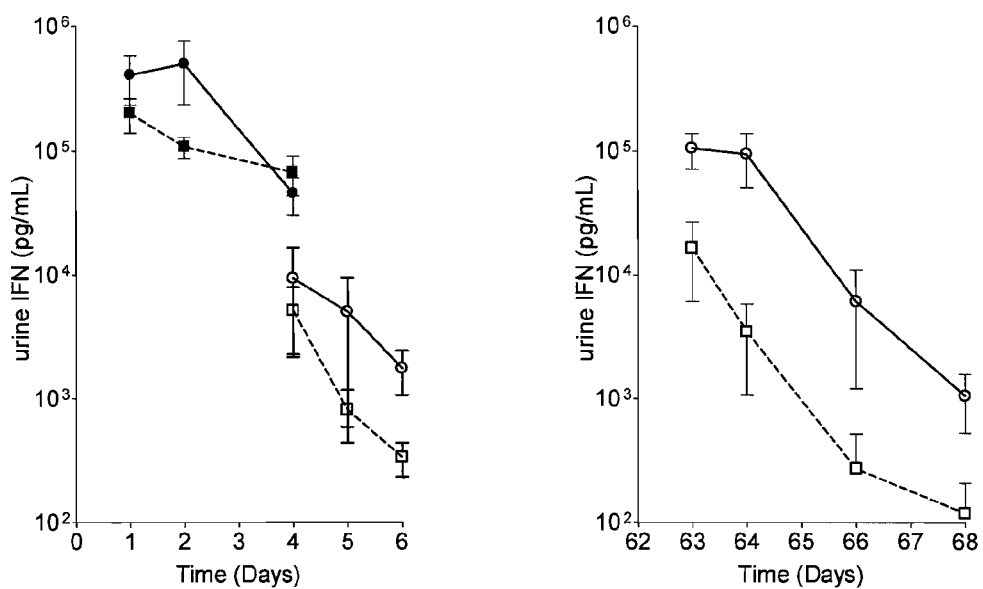

ADENOVIRAL EXPRESSION VECTORS

REFERENCE TO CROSS RELATED APPLICATIONS

This application is a continuation of U.S. Ser. No. 11/636,902 filed Dec. 11, 2006 which claims the benefit of priority under 35 USC 119(e) of provisional patent application U.S. Ser. No. 60/750,012 filed Dec. 12, 2005, the disclosures of which are hereby incorporated by reference in their entirety.

1. FIELD OF THE INVENTION

The present invention provides a recombinant adenovirus vector characterized by the partial or total deletion of adenoviral E2B function and having an expression cassette containing a heterologous sequence encoding a protein of interest inserted into the E1 region. Such vectors are designed to reduce or eliminate the occurrence of replication competent adenovirus contamination. Additionally, the expression cassette of the vector may contain one or more regulatory elements capable of increasing the expression of the heterologous sequence and/or reducing the expression of viral proteins. Such a reduction in expression of viral proteins reduces the cytotoxicty and immunogenicity of the adenovirus vectors when administered in vivo. Transformed production host cells and a method of producing recombinant proteins and gene therapy also are included within the scope of this invention.

2. BACKGROUND OF THE INVENTION

Recombinant adenovirus (rAd) vectors have desirable features for gene delivery, including wide tissue and cell tropism, the capacity to accommodate large expression cassettes and high transduction efficiency, and the capability to infect resting cells. The extremely row integrational tendency of adenoviruses is favourable as an additional safety aspect, since it minimizes the risk of insertion mutagenesis and oncogenic activation. A large number of different serotypes of human adenoviruses also provide choice of various viral sheaths with very different tropism. For example, group C viruses are extremely infectious for the liver or muscles, group D for cells of the central nervous system or group B for cells of the hemopoetic system. In addition, adenovirus is well suited for pharmaceutical development as the virus grows to high specific titers and scalable manufacturing processes have been established (Huyghe et al., 1995a; Shabram et al., 1997a).

Despite these decisive advantages the application possibilities for adenovirus vectors still remain limited. This is due to the fact that the adenoviruses vectors contain viral genes that are expressed in the target tissue. Direct toxicity, cut-off expression, inflammation of the tissue (Simon et al., 1993) and attack of cytotoxic T-lyphocytes are results which finally lead to destruction of infected cells. Numerous groups have tried to reduce the immunogenity of adenoviral vectors. E2 and E4 regions, which also have a transactivating function, where eliminated from the virus genome and were transferred into the helper cell line. However, it remains uncertain, whether these changes, which additionally cause reduction of the virus titres, are able to augment the duration of expression in vivo. As consequential continuation of this concept adenovirus vectors were developed in recent years, which are free from viral genes (Hardy et al., 1997; Kochanek et al., 1996; Kumar-Singh and Chamberlain, 1996; Mitani et al., 1995; Parks et al., 1996). However, such vectors are of little use for large scale pharmaceutical production.

3. SUMMARY OF THE INVENTION

The present invention provides a recombinant adenovirus vector characterized by the partial or total deletion of adenoviral E2B function and having an expression cassette containing a heterologous sequence encoding a protein of interest inserted into the E1 region. Such vectors are designed to have a reduction in the occurrence of replication competent adenovirus contamination. Additionally, the expression cassette of the vector may contain one or more elements capable of increasing the expression of the heterologous sequence and/or reducing the expression of viral proteins. Such a reduction in expression of viral proteins is intended to reduce the cytotoxicity and immunogenicity of the adenovirus vectors when administered in vivo.

The expression cassette of the vector is engineered to contain a heterologous sequence, i.e., a transgene, that encodes a protein of interest, or a functional fragment or mutant thereof. Such transgenes include, but are not limited to, those genes encoding any protein having therapeutic utility, genes that replace defective genes in the target host cell, such as those responsible for genetic defect based diseased conditions; and/or genes which have therapeutic utility in the treatment of cancer, autoimmune and/or infectious diseases. Transformed host cells and a method of producing recombinant proteins and gene therapy also are included within the scope of this invention.

The expression cassette may additionally comprise one or more additional nucleic acid sequences that are designed to increase transgene expression, while reducing the expression of viral proteins. For example, the expression cassette may be engineered to contain an "insulator sequence" that functions to prevent the expression of genes found adjacent to the cassette from being activated. Thus, by insertion of an insulator sequence at the 3' end of the expression cassette, expression of viral genes found adjacent to the expression cassette should remain low.

In yet another embodiment of the invention, the expression cassette may have the E1B polyA sequences substituted with heterologous polyA sequences that are know to enhance RNA polyadenylation and stability. Such substitutions may result in increased levels of transgene expression. PolyA sequences that may be utilized are well known to those of skill in the art and, include but are not limited to, bovine growth hormone polyA sequences.

In yet another embodiment of the invention, the expression cassette may additionally comprise a posttranscriptional regulatory element (PRE), such as those derived from mammalian hepadnaviruses. Such PRE sequences include, for example, those derived from hepatitis B virus (HBV) and woodchuck hepatitis virus (WHV).

In yet another embodiment of the invention, the expression cassette may additionally comprise an intron sequence inserted into the 5' LTR of the expression cassette to increase transgene expression. Intron sequences, that may be used in the practice of the invention, are well known to those of skill in the art. Such sequences may be generated from known consensus splicing sequences.

The present invention also provides recombinant adenoviral vectors and therapeutic methods, for example, relating to gene therapy, vaccination, and the like, involving the use of such recombinants.

4. BRIEF DESCRIPTION OF THE FIGURES

FIG. 1 is a schematic diagram of the structure of the T2VP vector. As depicted, the vector contains deletions in the E1, E2B and E3 regions, and insertion of a transgene cassette into the E1 region of the virus. The transgene cassette includes the CMV promoter, the adenovirus 5 tripartite leader, a synthetic intron sequence 5' to the transgene, i.e, rSEAP, a WPRE sequence, the BGH poly A sequence and a synthetic insulator sequence.

FIG. 2 depicts a comparison of SEAP expression in Ku-7 bladder cells infected with T2VP and other control viruses. In vitro testing demonstrates equivalent or increased expression of SEAP compared to control vectors.

FIG. 3 is an in vivo analysis of urine SEAP expression following intravesical delivery of T2VP and RCCB (control). As an example this experiment demonstrated that intravesical administration of T2VP to rat bladders improved duration of expression at a shortened redose time compared to RCCB a standard E1-deleted adenovirus. There was an approximate ten fold decrease in SEAP expression between the initial and redose for the control RCCB vector, while the levels remained the same between the initial and redose of the T2VP vector. Anesthetized female Sprague-Dawley rats received an intravesical administration of recombinant adenovirus (~5×10$^{10}$ particles in 500 μL). Test articles were retained in the bladder for ~1 hour and animals were permitted to void and recover. Timed urine samples beginning 24 hours after dosing were collected and analyzed for SEAP by ELISA. SEAP concentrations after the first intravesical administration are shown as solid symbols (Initial Dose). SEAP concentrations measured after a second intravesical dose (53 days later) are plotted as open symbols (53 Day Redose). Methods described in detail in Connor et al., 2005.

FIG. 4 is a schematic diagram of the structure of the T8BF vector compared to the IACB vector or rAdIFN vector (Benedict et al., 2004; Demers et al., 2002a; Demers et al., 2002b; Iqbal Ahmed et al., 2001; U.S. Pat. No. 6,210,939, the contents of which are herein incorporated by reference in their entirety). Showing differences in the E2b region and transgene cassette.

FIGS. 5A-E presents the sequence and localization of features of the transgene cassette from T8BF (SEQ ID NO: 1; SEQ ID NO: 2).

FIGS. 6A-K shows the full sequence of the T8BF adenovirus vector, including the transgene cassette (starting at nucleotide 365; see FIG. 5) comprising the sequence for interferon alpha 2b (SEQ ID NO: 3).

FIG. 7 is a comparison in vitro of interferon alpha 2b expression from IACB and T8BF. A549 cells were infected and analyzed 72 hours post infection As indicated an improvement in expression of interferon alpha 2b was observed when compared to the control virus IACB, which contains an E1 deletion.

FIG. 8 is an in vivo comparison of interferon alpha 2b expression from IACB and T8BF at both initial dose and 62 day redose. In this example, T8BF (circles) and IACB (squares) data is shown as mean±SE for two experiments where n=5 (filled) and n=6 (open). Normal rats were dosed as described in FIG. 3 legend and Connor et al., 2005 and human interferon alpha 2b measured by ELISA.

5. DETAILED DESCRIPTION OF THE INVENTION

The present invention provides, inter alia, recombinant adenoviruses characterized by the partial or total deletion of the adenoviral E2B gene and having an expression cassette capable of encoding a protein of interest inserted into the E1 region. The subject vectors will find use in therapeutic applications, in which the vectors are employed to express a therapeutic nucleic acid, e.g. gene, into the genome of a target cell, i.e. gene therapy applications. The subject vectors may be used to deliver a wide variety of therapeutic nucleic acids. Therapeutic nucleic acids of interest include genes that replace defective genes in the target host cell, such as those responsible for genetic defect based diseased conditions; genes which have therapeutic utility in the treatment of cancer, autoimmune and/or infectious diseases and the like.

In accordance with the present invention there may be employed conventional molecular biology, microbiology, and recombinant DNA techniques within the skill of the art. Such techniques are explained in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook, et al., 1989"); *DNA Cloning: A Practical Approach*, Volumes I and II (D. N. Glover ed. 1985); *Oligonucleotide Synthesis* (M. J. Gait ed 1984); *Nucleic Acid Hybridization* (B. D. Hames & S. J. Higgins eds. 1985)); *Transcription And Translation* (B. D. Hames & S. J. Higgins, eds. (1984)); *Animal Cell Culture* (R. I. Freshney, ed. (1986)); *Immobilized Cells And Enzymes* (IRL Press, (1986)); B. Perbal, *A Practical Guide To Molecular Cloning* (1984); F. M. Ausubel, et al. (eds.), *Current Protocols in Molecular Biology*, John Wiley & Sons, Inc. (1994).

5.1 Terminology

As used herein, the term "adenovirus" refers to viruses of the genus adenoviridiae. The term "recombinant adenovirus" refers to viruses of the genus adenoviridiae capable of infecting a cell whose viral genomes have been modified through conventional recombinant DNA techniques. The term recombinant adenovirus also includes chimeric (or even multimeric) vectors, i.e. vectors constructed using complementary coding sequences from more than one viral subtype.

As used herein, the term "recombinant adenovirus vector(s)" refers to a vector construct comprising adenoviral nucleotide sequences and optionally, one or more heterologous nucleotide sequences. In a preferred embodiment, the recombinant adenovirus vectors comprise adenoviral nucleotide sequences that have reduced homology to the helper adenovirus nucleic acid sequences. In another preferred embodiment, the recombinant adenovirus vector encodes a replication-defective adenovirus. In accordance with this embodiment, the recombinant adenovirus vector may be engineered to comprise a mutated adenovirus genome by, e.g., introducing one or more mutations in an adenovirus genome (e.g., introducing deletions in one or more coding regions for adenoviral proteins).

As used herein, the term "adenoviridae" refers collectively to animal adenoviruses of the genus mastadenovirus including but not limited to human, bovine, ovine, equine, canine, porcine, murine and simian adenovirus subgenera. In particular, human adenoviruses include the A-F subgenera as well as the individual serotypes thereof. A-F subgenera including but not limited to human adenovirus types 1, 2, 3, 4, 4a, 5, 6, 7, 7a, 7d, 8, 9, 10, 11 (Ad11A and Ad11P, 12, 13, 14, 15, 16, 17, 18, 19, 20, 21, 22, 23, 24, 25, 26, 27, 28, 29, 30, 31, 32, 33, 34, 34a, 35, 35p, 36, 37, 38, 39, 40, 41, 42, 43, 44, 45, 46, 47, 48, and 91.

As used herein, the term "E1A gene" and "E1B region" refers to the immediate early genes of the adenovirus genome first transcribed following infection. For example, the E1A coding region spans nucleotide 560-1542 and the E1B coding region spans 1714-2242. As used herein, the term "E2B gene" refers to the early gene of the adenovirus genome that encodes the 140 kD DNA polymerase. The E2 region also encodes the precursor to the terminal protein (80 kD) that is cleaved during viral assembly to 55 kD while covalently bound to DNA The E2B coding region spans nucleotide 8367-5197 of adenovirus type 5. GenBank® deposits of the complete human adenovirus type 5 genome are available, see for example, AY339865 and AC000008.

As used herein, the term "expression cassette" is used herein to define a nucleotide sequence capable of directing the transcription and translation of a heterologous coding sequence and the heterologous coding sequence to be expressed. An expression cassette comprises a regulatory element operably linked to a heterologous coding sequence so as to achieve expression of the protein product encoded by said heterologous coding sequence in the cell.

As used herein, the term "heterologous" in the context of nucleic acid sequences, amino acid sequences and antigens refers to nucleic acid sequences, amino acid sequences and antigens that are foreign and are not naturally found associated with a particular adenovirus.

As used herein, the term "operably linked" refers to a linkage of polynucleotide elements in a functional relationship. A nucleic acid sequence is "operably linked" when it is placed into a functional relationship with another nucleic acid sequence. For instance, a promoter or enhancer is operably linked to a coding sequence if it affects the transcription of the coding sequence. Operably linked means that the nucleotide sequences being linked are typically contiguous. However, as enhancers generally function when separated from the promoter by several kilobases and intronic sequences may be of variable lengths, some polynucleotide elements may be operably linked but not directly flanked and may even function in trans from a different allele or chromosome.

As used herein, the term "regulatory element" refers to promoters, enhancers, transcription terminators, insulator regions, silencing region, polyadenylation sites, intron sequences, post transcriptional regulatory elements and the like. The term "promoter" is used in its conventional sense to refer to a nucleotide sequence at which the initiation and rate of transcription of a coding sequence is controlled. The promoter contains the site at which RNA polymerase binds and also contains sites for the binding of regulatory factors (such as repressors or transcription factors). Promoters may be naturally occurring or synthetic. When the vector to be employed is a viral vector, the promoters may be endogenous to the virus or derived from other sources. The regulatory elements may be arranged so as to allow, enhance or facilitate expression of the transgene only in a particular cell type. For example, the expression cassette may be designed so that the transgene is under control of a promoter which is constitutively active, or temporally controlled (temporal promoters), activated in response to external stimuli (inducible), active in particular cell type or cell state (selective) constitutive promoters, temporal viral promoters or regulatable promoters.

As used herein, the term "infecting" means exposing the recombinant adenovirus to a complementing cell line under conditions so as to facilitate the infection of the producer cell with the recombinant adenovirus. In complementing cells which have been infected by multiple copies of a given virus, the activities necessary for viral replication and virion packaging are cooperative. Thus, it is preferred that conditions be adjusted such that there is a significant probability that the cells are multiply infected with the virus. An example of a condition which enhances the production of virus in the cell is an increased virus concentration in the infection phase. However, it is possible that the total number of viral infections per cell can be overdone, resulting in toxic effects to the cell. Consequently, one should strive to maintain the infections in the virus concentration in the range of $10^6$ to $10^{10}$, preferably about $10^9$, virions per ml. Chemical agents may also be employed to increase the infectivity of the cell line. For example, the present invention provides a method to increase the infectivity of cell lines for viral infectivity by the inclusion of a calpain inhibitor. Examples of calpain inhibitors useful in the practice of the present invention include, but are not limited to, calpain inhibitor 1 (also known as N-acetyl-leucyl-leucyl-norleucinal, commercially available from Boehringer Mannheim). Calpain inhibitor 1 has been observed to increase the infectivity of cell lines to recombinant adenovirus (see, e.g. U.S. Pat. No. 7,001,770 herein incorporated by reference in its entirety).

As used herein, the term "culturing under conditions to permit replication of the viral genome" means maintaining the conditions for complementation so as to permit the recombinant adenovirus to propagate in the cell. It is desirable to control conditions so as to maximize the number of viral particles produced by each cell. Consequently it will be necessary to monitor and control reaction conditions such as temperature, dissolved oxygen, pH, etc. Commercially available bioreactors such as the CelliGen Plus Bioreactor (commercially available from New Brunswick Scientific, Inc. 44 Talmadge Road, Edison, N.J.) have provisions for monitoring and maintaining such parameters. Optimization of infection, transfection and culture conditions will vary somewhat, however, conditions for the efficient replication and production of virus may be achieved by those of skill in the art taking into consideration, for example, the known properties of the producer cell line, properties of the virus and the type of bioreactor.

As used herein, the term "helper adenovirus nucleic acid sequence(s)" refers to a nucleic acid sequence(s) that: (i) provides viral functions for the replication of a recombinant adenovirus vector and/or its packaging into infectious virions; and (ii) is (are) not replicated or assembled into viral particles to a measurable degree.

As used herein, the terms, "recombinant adenovirus production cell line", "recombinant adenovirus complementation cells", and "recombinant adenovirus complementation cell lines" are synonyms and mean a cell able to propagate recombinant adenoviruses by providing viral functions for replication of a recombinant adenovirus and/or its packaging into infectious virions.

As used herein, the term "transfection" or "transformation" means the introduction of a nucleic acid into a cell. A host cell that receives the introduced DNA or RNA has been "transformed" and is a "transformant" or a "clone." Examples of transformation methods which are very well known in the art include liposome delivery, electroporation, $CaPO_4$ transformation, DEAE-Dextran transformation, microinjection and viral infection.

5.2 Recombinant Adenovirus Constructs

The recombinant adenovirus vectors of the invention comprise adenoviral nucleotide sequences and optionally, one or more heterologous nucleotide sequences. In a preferred embodiment, the recombinant adenovirus vectors comprise adenoviral nucleotide sequences having decreased homology to the adenovirus nucleic acid sequences of the complementing cell lines. The lack of homology between the adenoviral helper nucleic acid sequences and recombinant adenovirus vectors reduces the possibility of the viral genome recombining to produce replication competent adenovirus. In a preferred embodiment, the recombinant adenovirus vector encodes a replication-defective adenovirus. In accordance with this embodiment, the recombinant adenovirus vector may be engineered to comprise a mutated adenovirus genome by, e.g., introducing one or more mutations in an adenovirus genome (e.g., introducing deletions in one or more coding regions for adenoviral proteins). Preferably, the mutations in the adenovirus genome result in lower levels of expression of adenoviral proteins than wild-type adenovirus. The reduction in adenoviral protein expression reduces the immune response to the adenoviral proteins in a subject.

In a specific embodiment, the recombinant adenovirus vector encodes an E1 deleted replication-defective adenovirus and comprises a mutated genome with a partial or complete (preferably, a complete) deletion of the E2B polymerase function, and includes a heterologous nucleotide sequence. In a preferred embodiment, the recombinant adenovirus vector encodes a replication-defective adenovirus and comprises a mutated genome with a partial or complete (preferably, a complete) deletion of the E1A coding region, E1B coding region, E2B polymerase coding region and includes a heterologous nucleotide sequence in the deleted E1 coding region.

In an embodiment of the invention, deletions in the E2B region include those sufficient to lead to the production of a non-functional DNA polymerase. In a preferred embodiment of the invention the deletion in the E2B region retains sequences that encode viral proteins on the opposite strand. Mutations, that may be used in the practice of the invention include, but are not limited to, the E2b deletion of nucleotides 7274 to about 7881 (see Amalfitano et al., 1998, herein incorporated by reference in its entirety). In yet another embodiment of the invention point mutations may be genetically engineered into the E2B coding region which result in a decrease in functional adenovirus polymerase expression. In a specific embodiment of the invention, the start codon of the E2B gene may be mutated to prevent translation of the E2B mRNA, thereby eliminating the function of E2B polymerase activity.

The heterologous nucleotide sequences can be introduced into any region of the genome (e.g., the amino or carboxy-termini). In a specific embodiment, a heterologous nucleotide sequence is introduced into one of the deleted adenoviral coding regions, such as the E1, E2B or E3 coding region, of the mutated adenoviral genome. In a preferred embodiment of the invention, the heterologous nucleotide sequence is introduced into the deleted E1 coding region of the mutated adenoviral genome.

In accordance with the invention, the recombinant adenovirus vectors comprise an adenoviral genome or a portion thereof obtained and/or derived from any adenoviridae or a combination of adenoviridae. In a preferred embodiment, the recombinant adenovirus vectors comprise an adenoviral genome or portion thereof obtained and/or derived from a human adenoviridae. In another preferred embodiment, the recombinant adenovirus vectors comprise an adenoviral genome or portion thereof obtained and/or derived from the human adenovirus serotype 2 or 5.

In one embodiment the recombinant adenovirus vector is derived from a human adenovirus serotype 5 and comprises deletions of the E1a, E1b and protein IX functions and deletions in the E3 region (see e.g., U.S. Pat. Nos. 6,210,939 and 5,932,210, herein incorporated by reference in their entirety) and the E2b region. By way of example, and not limitation, the recombinant adenovirus vector derived from a human adenovirus serotype 5 can comprise a deletion of base pairs 357 to about base pairs 4050, such as, for example, base pairs 360 to between about base pairs 4030, a deletion of base pairs 28,597 to between about base pairs 30,471 and a deletion in the E2b region as described in Amalfitano, A. et al (1998), herein incorporated by reference in its entirety.

In another embodiment, the recombinant adenovirus vector is derived from a human adenovirus serotype 5 and comprises deletions of the same adenoviral sequences as shown in the adenoviral vector in FIG. 6.

The present invention relates to recombinant adenovirus expression vectors comprising an "expression cassette" which is inserted into the mutated adenoviral genome. As used herein, the term "expression cassette" is defined as a nucleotide sequence capable of directing the transcription and translation of a heterologous coding sequence and the heterologous coding sequence to be expressed. An expression cassette comprises a regulatory element operably linked to a heterologous coding sequence so as to achieve expression of the protein product encoded by said heterologous coding sequence in the cell.

In an embodiment of the invention, the heterologous nucleotide sequence is obtained and/or derived from a source other than the recombinant adenovirus vector. In accordance with the invention, the heterologous nucleotide sequence may encode a moiety, peptide, polypeptide or protein possessing a desired biological property or activity.

In certain embodiments, the heterologous nucleotide sequence encodes a biological response modifier such as a cytokine, cytokine receptor, hormone, growth factor or growth factor receptor. Non-limiting examples of such biological response modifiers include interferon (IFN)-alpha, IFN-beta, IFN gamma, interleukin (IL-1), IL-2, IL-3, IL-4, IL-5, IL-6, IL-7, IL-9, IL-10, IL-12, IL-15, IL-18, IL-23, erythropoietin (EPO), basic fibroblast growth factor (bFGF), acidic fibroblast growth factor (aFGF), vascular endothelial growth factor (VEGF), platelet derived growth factor (PDGF), epidermal growth factor (EGF), thymic stromal lymphopoietin (TSLP), GM-CSF, TNFR and TNFR ligand superfamily members including TNFRSF 18 and TNFSF18. In a preferred embodiment the nucleotide sequence encodes an interferon, such as Interferon alpha 2b. (see, e.g. U.S. Pat. No. 6,835,557, herein incorporated by reference in its entirety).

In other embodiments, the heterologous nucleotide sequence encodes an antibody. In yet other embodiments, the heterologous nucleotide sequence encodes a chimeric or fusion protein.

In certain embodiments, the heterologous nucleotide sequence encodes an antigenic protein, a polypeptide or peptide of a virus belonging to a different species, subgroup or variant of adenovirus other than the species, subgroup or variant from which the recombinant adenovirus vector is derived. In certain embodiments, the heterologous nucleotide sequence encodes an antigenic protein, polypeptide or peptide obtained and/or derived from a pathogenic microorganism.

In yet another embodiment of the invention, the heterologous nucleotide sequence is a cancer therapeutic gene. Such genes include those that enhance the antitumor activity of lymphocytes, genes whose expression product enhances the immunogenicity of tumor cells, tumor suppressor genes, toxin genes, suicide genes, multiple-drug resistance genes, antisense sequences, and the like. Thus, for example, the adenoviral vector of this invention can contain a foreign gene for the expression of a protein effective in regulating the cell cycle, such as p53, Rb, or mitosin, or in inducing cell death, such as the conditional suicide gene thymidine kinase.

According to the invention, if the heterologous nucleotide sequence of the recombinant adenovirus vector is to be expressed in host cells, a transcriptional control element, also called a promoter/enhancer sequence, should be provided. The promoter/enhancer sequence may be widely active or may, alternatively, be tissue specific. The promoter/enhancer sequence may be derived from a non-adenovirus source or may be an adenovirus promoter. In a preferred embodiment, the promoter/enhancer sequences used to regulate the expression of the heterologous nucleotide sequence are not shared with those promoter/enhancer sequences that regulate the expression of the helper adenovirus nucleic acid sequences. In accordance with this embodiment, a promoter can be any promoter known to the skilled artisan. For example, the promoter can be a constitutive promoter, a tissue-specific promoter or an inducible promoter. Examples of promoters that may be used in accordance with the invention include: the SV40 early promoter (Benoist and Chambon, 1981), the promoter contained in the 3' long terminal repeat of Rous sarcoma virus (Yamamoto et al., 1980), the herpes thymidine kinase promoter (Wagner et al., 1981), the regulatory sequences of the metallothionein gene (Brinster et al., 1982), the beta-actin promoter, the CMV promoter, the SR-alpha promoter, the hFer/SV40 promoter, the Elf-1 promoter, the Tet promoter, the Ecdysone promoter and a rapamycin promoter.

In a specific embodiment, a native promoter is utilized to regulate the expression of a nucleotide sequence encoding an adenoviral protein. In alternative embodiment, a promoter that is not native to the adenoviral gene encoding the protein being expressed (i.e., a heterologous promoter) is utilized to regulate the expression of the protein. In certain embodiments, the promoter is a constitutive promoter (e.g., a viral, cellular or hybrid constitutive promoter). In other embodiments, the promoter is an inducible promoter. In yet other embodiments, the promoter is a tissue-specific promoter.

In certain embodiments, it is desirable to use a constitutive promoter, such as a CMV promoter, β-actin promoter, SR-alpha promoter or hFer/SV40 promoter, to regulate the expression of the heterologous nucleotide sequence. In certain other embodiments, it is desirable to use a constitutive promoter, such as a RSV promoter, SV40 promoter or Elf-1 promoter, to regulate the expression of the heterologous nucleotide sequence. In yet other embodiments, it is desirable to use an inducible promoter, such as a Tet promoter or Ecdysone promoter, to regulate the expression of the heterologous nucleotide sequence of the adenovirus vector.

In yet another embodiment of the invention, an inducible promoter can be used in the adenoviral vector of the invention. These promoters will initiate transcription only in the presence of an additional molecule. Examples of inducible promoters include those obtainable from a β-interferon gene, a heat shock gene, a metallothionine gene or those obtainable from steroid hormone-responsive genes. Tissue specific expression has been well characterized in the field of gene expression and tissue specific and inducible promoters such as these are very well known in the art. These genes are used to regulate the expression of the foreign gene after it has been introduced into the target cell.

The desirable size of inserted non-adenovirus or heterologous nucleotide sequence is limited to that which permits packaging of the recombinant adenovirus vector into virions, and depends on the size of retained adenovirus sequences. The genome of a human adenovirus is approximately 36 kilobase pairs in length (measured to be 35938 nucleotides in length by (Davison et al., 2003). The total size of the recombinant adenovirus to be packaged into virions should be about 37735 nucleotides in length (about 105% of the normal genome length). Therefore, it may be desirable to exclude additional portions of the adenovirus genome, such as the E3 region, in the recombinant adenovirus vector in order to maximize expression of the inserted heterologous nucleotide sequence.

Insertion of a foreign gene sequence into a recombinant adenovirus vector of the invention can be accomplished by either a complete replacement of a viral coding region with a heterologous nucleotide sequence or by a partial replacement or by adding the heterologous nucleotide sequence to the viral genome. Complete replacement would probably best be accomplished through the use of PCR-directed mutagenesis. Briefly, PCR-primer A would contain, from the 5' to 3' end: a unique restriction enzyme site, such as a class IIS restriction enzyme site (i.e., a "shifter" enzyme; that recognizes a specific sequence but cleaves the DNA either upstream or downstream of that sequence); a stretch of nucleotides complementary to a region of the gene that is to be replaced; and a stretch of nucleotides complementary to the carboxy-terminus coding portion of the heterologous nucleotide sequence. PCR-primer B would contain from the 5' to 3' end: a unique restriction enzyme site; a stretch of nucleotides complementary to the gene that is to be replaced; and a stretch of nucleotides corresponding to the 5' coding portion of the heterologous or non-native gene. After a PCR reaction using these primers with a cloned copy of the heterologous or non-native gene, the product may be excised and cloned using the unique restriction sites. Digestion with the class IIS enzyme and transcription with the purified phage polymerase would generate a RNA molecule containing the exact untranslated ends of the viral gene that carries now a heterologous or non-native gene insertion. In an alternate embodiment, PCR-primed reactions could be used to prepare double-stranded DNA containing the bacteriophage promoter sequence, and the hybrid gene sequence so that RNA templates can be transcribed directly without cloning.

When inserting a heterologous nucleotide sequence into the recombinant adenovirus vector of the invention, the intergenic region between the end of the coding sequence of the heterologous nucleotide sequence and the start of the coding sequence of the downstream gene can be altered to achieve a desired effect. As used herein, the term "intergenic region" refers to nucleotide sequence between the stop signal of one gene and the start codon (e.g., AUG) of the coding sequence of the next downstream open reading frame. An intergenic region may comprise a non-coding region of a gene, i.e., between the transcription start site and the start of the coding sequence (AUG) of the gene. This non-coding region occurs naturally in some viral genes.

In an embodiment of the invention, sequences referred to as "insulators" may be inserted into the expression cassette, in the intergenic region downstream of the heterologous nucleotide sequence (Di Simone et al., 2001; Martin-Duque et al., 2004a; Pluta et al., 2005; Puthenveetil et al., 2004; Qu et al., 2004; Rincon-Arano and Recillas-Targa, 2004; Takada et al., 2000) The insertion of such insulators can result in decreased expression of adenoviral proteins, as compared to wild type, which is useful in reducing the immunogenicity and toxicity of the adenovirus vectors. Insulator sequences that may be used in the practice of the invention are well known to those of skill in the art and include, for example, hypersensitive site 4 (HS4) of the β-globin gene locus. The HS4 locus has been used in retroviruses (Emery et al., 2002; Jakobsson et al., 2004; Pannell and Ellis, 2001; Yannaki et al., 2002; Yao et al., 2003) and also adenovirus vectors (Cheng et al., 2004; Martin-Duque et al., 2004b; Steinwaerder and Lieber, 2000; Ye et al., 2003). The region of the HS4 locus being responsible for the control of gene expression through chromatin rearrangement and blocking activities has been attributed to the transcriptional modulator CTCF (Bell et al., 1999; Dunn and Davie, 2003; Dunn et al., 2003; Emery et al., 2002; Farrell et al., 2002; Jakobsson et al., 2004; Kanduri et al., 2002; Lewis and Murrell, 2004; Lutz et al., 2000; Mukhopadhyay et al., 2004; Pannell and Ellis, 2001; Recillas-Targa et al., 2002; Saitoh et al., 2000; Szabo et al., 2002; Thorvaldsen et al., 2002; Valadez-Graham et al., 2004; Yannaki et al., 2002; Yao et al., 2003; Yusufzai and Felsenfeld, 2004; Yusufzai et al., 2004; Zhang et al., 2004; Zhao and Dean, 2004). In an embodiment of the invention, an insulator comprising four head to tail copies of the CTCF binding site from the hypersensitive site 4 of the β-globin gene locus may be use as an insulator. In another embodiment, other synthetic insulator sequences (Bell et al., 2001; Brasset and Vaury, 2005; Zhao and Dean, 2004) may also be used.

In yet another embodiment of the invention, the E1B poly A signal sequence may be replaced with a heterologous polyA sequence that increases the polyadenylation and RNA stabilization of the heterologous gene. Such an increase in polyadenylation and RNA stabilization may result in more efficient expression of the heterologous gene product. In a non-limiting embodiment of the invention, the poly A signal sequences comprises sequences containing the following consensus sequences AATAAA or AATTAA. In an embodiment of the invention, the polyA sequence may be derived from a virus, such as the SV40 virus. In a specific embodiment of the invention the the E1B polyA sequence may be substituted with the bovine growth hormone (BGH) polyadenylation signal sequence. (Xu et al., 2002; Youil et al., 2003) The BGH poly A sequence may be obtained by PCR from existing commercially available plasmids.

In yet another embodiment of the invention, the recombinant adenoviruses of the invention may include post-transcriptional regulatory element (PRE) that function to increase transgene expression. Such elements including, for example, the woodchuck hepatitis PRE (Donello et al., 1998), the hepatitis B virus PRE (Huang and Yen, 1994) or the herpes simplex PRE (Liu and Mertz, 1995) are inserted into the expression cassette at a location downstream of the heterologous gene (Appleby et al., 2003; Breckpot et al., 2003; Brun et al., 2003; Glover et al., 2002; Glover et al., 2003; Gropp et al., 2003; Mangeot et al., 2002; Robert et al., 2003; Schwenter et al., 2003; Werner et al., 2004; Xu et al., 2003; Yam et al., 2002; Zufferey et al., 1999).

The present invention also provides a recombinant adenovirus wherein the expression cassette is engineered to contain an intron sequence engineered into the 5' untranslated region of the heterologous gene (Choi et al., 1991; Hermening et al., 2004; Lee et al., 1997; Xu et al., 2002; Xu et al., 2003. The intron sequences to be used in the practice of the invention can be generated from know consensus splicing sequences using, for example, PCR with primers that incorporate the necessary consensus splicing signals. Intron sequences include a 5' splice donor site and a 3' splice region that includes a branch point sequence and a 3' splice acceptor AG site. The 3' splice region may further comprise a polypyrimidine tract. Consensus sequences for the 5' splice donor site and the 3' splice region used in RNA splicing are well known in the art (See, Moore, et al., 1993, The RNA World, Cold Spring Harbor Laboratory Press, pp. 303-358). In addition, modified consensus sequences that maintain the ability to function as 5' donor splice sites and 3' splice regions may be used in the practice of the invention. Briefly, the 5' splice site consensus sequence is AG/GURAGU (where A=adenosine, U=uracil, G=guanine, C=cytosine, R=purine and/=the splice site). The 3' splice site consists of three separate sequence elements: the branch point or branch site, a polypyrimidine tract and the 3' consensus sequence (YAG). The branch point consensus sequence in mammals is YNYURAC (Y=pyrimidine; N=any nucleotide). The underlined A is the site of branch formation. A polypyrimidine tract is located between the branch point and the splice site acceptor and is important for efficient branch point utilization and 3' splice site recognition. Other pre-messenger RNA introns beginning with the dinucleotide AU and ending with the dinucleotide AC have been identified and referred to as U12 introns. U12 intron sequences as well as any additional sequences that function as splice acceptor/donor sequences may also be used to generate the expression cassette of the invention.

In yet another embodiment of the invention the 5' untranslated region of the expression cassette comprises the adenovirus tripartite leader.

In one embodiment the expression vector comprises one or more heterologous nucleotide sequences, CMV promoters, a tripartite leader sequences, synthetic introns, WPRE sequences, polyA regions and CTCF binding sites. By way of example, and not limitation, the recombinant adenovirus vectors of the invention can comprise the expression cassette shown in FIG. 5.

The expression of the inserted heterologous nucleotide sequence can be determined by various indexes including, but not limited to, protein or mRNA expression levels, measured by following non-limiting examples of assays: immunostaining, immunoprecipitation and immunoblotting, enzyme-linked immunosorbent assay, nucleic acid detection (e.g., Southern blot analysis, Northern blot analysis, Western blot analysis), employment of a reporter gene (e.g., using a reporter gene, such as Green Fluorescence Protein (GFP) or enhanced Green Fluorescence Protein (eGFP), integrated to the viral genome the same fashion as the interested heterologous gene to observe the protein expression), or a combination thereof. Procedures of performing these assays are well known in the art (see, e.g. Flint et al., PRINCIPLES OF VIROLOGY, MOLECULAR BIOLOGY, PATHOGENESIS, AND CONTROL, 2000, ASM Press pp 25-56, the entire text is incorporated herein by reference).

For example, expression levels can be determined by infecting cells in culture with a recombinant adenovirus of the invention and subsequently measuring the level of protein expression by, e.g., Western blot analysis or ELISA using antibodies specific to the gene product of the heterologous nucleotide sequence, or measuring the level of RNA expression by, e.g., Northern blot analysis using probes specific to the heterologous sequence. Similarly, expression levels of the heterologous sequence can be determined by infecting an animal model and measuring the level of protein expressed from the heterologous nucleotide sequence of the recombinant virus of the invention in the animal model. The protein level can be measured by obtaining a tissue sample from the infected animal and then subjecting the tissue sample to Western blot analysis or ELISA, using antibodies specific to the gene product of the heterologous sequence. Further, if an animal model is used, the titer of antibodies produced by the animal against the gene product of the heterologous sequence can be determined by any technique known to the skilled artisan, including but not limited to, ELISA.

According to the invention, a recombinant adenovirus vector may be propagated in microorganisms, for example, as part of a bacterial plasmid or bacteriophage, in order to obtain large quantities of recombinant adenovirus vector.

5.4 Production of Recombinant Adenovirus

In accordance with the invention, recombinant adenovirus (preferably, recombinant replication-defective adenovirus) may be produced by co-transfecting an appropriate cell type with recombinant adenovirus vector and helper adenovirus nucleic acid sequences. Co-transfection may be performed by the DEAE dextran method (McCutchan and Pagano, 1968), the calcium phosphate procedure (Graham and van der Eb, 1973) or by any other method known in the art, including but not limited to microinjection, lipofection, and electroporation. Amounts of recombinant adenovirus vector and helper adenovirus nucleic acid sequences used in transfection are approximately 0.2 to 10 µg of DNA per $10^6$ cells, but may vary among different DNA constructs and cell types. Cells suitable for transfection include any cell line permissive for adenvirus infection, including, but not limited to HeLa cells, 293-D22 cells, A549 cells, HCT-15 cells, IGROV-1 cells, U87 cells and W162 cells.

Alternatively, a recombinant adenovirus complementing cell line may be transfected with recombinant adenovirus vector to produce of recombinant adenovirus (preferably, recombinant replication-defective adenovirus). In a specific embodiment, the present invention provides a method for producing recombinant adenovirus comprising culturing a recombinant adenovirus complementing cell line transfected with recombinant adenovirus vector under conditions so as to permit replication of the viral genome in the cell line, wherein the cell line comprises: (a) a first nucleic acid molecule comprising a nucleotide sequence encoding adenoviral E1A proteins; (b) a second nucleic acid molecule comprising a nucleotide sequence encoding an adenoviral E1B-55K protein (and preferably, does not comprise a nucleotide sequence encoding an adenoviral E1B-19K protein); and (c) a third nucleic acid molecule comprising a nucleotide sequence encoding an adenoviral E2B polymerase.

In a non-limiting embodiment of the invention, the SL0006 transformed cell line which has been engineered to express the E1A, E1B and E2B polymerase and which is described in U.S. patent application Ser. No. 60/674,488 and U.S. Publication No.; 2006/027004 (the disclosures of which are herein incorporated by reference), can be used to propagate the recombinant adenoviruses of the invention. The SL0006 cell line is deposited under the Budapest Treaty with the American Type Culture Collection (ATCC), 10801 University Blvd., Manassas, Va., 20110-2209, USA, under ATCC Accession Number: PTA-6663.

Recombinant adenovirus of the present invention may be produced by any suitable method, many of which are known in the art (see, e.g., (Berkner and Sharp, 1983; Berkner and Sharp, 1984; Brough et al., 1992). In the preferred practice of the invention, the recombinant adenoviruses are derived from the human adenoviridae. In a preferred embodiment of the invention, the recombinant adenovirus is derived from the human adenovirus serotype 2 or 5.

In a preferred practice of the invention, the produced recombinant adenovirus is a replication-defective adenovirus comprising a mutated genome with a partial or complete (preferably, complete) deletion of the E1A coding region, E1B coding region, and E2B polymerase coding region, and includes one or more heterologous nucleotide sequences in the E1 region.

In another embodiment of the invention, the recombinant adenovirus is a replication-defective adenovirus and comprises a mutated genome with a partial or complete (preferably, complete) deletion of the E1A coding region, E1B coding region, E2B polymerase coding region, and E3 coding region, and includes one or more heterologous nucleotide sequences in the deleted E1 coding region.

In another embodiment of the invention, the recombinant adenovirus is a replication-defective adenovirus and comprises a mutated genome with a partial or complete (preferably, complete) deletion of the E1A coding region, E1B coding region, E2B polymerase coding region, and E4 coding region, and includes one or more heterologous nucleotide sequences in the deleted E1 coding region.

In another embodiment of the invention, the recombinant adenovirus is a replication-defective adenovirus and comprises a mutated genome with a partial or complete (preferably, complete) deletion of the E1A coding region, E1B coding region, E2B polymerase coding region, E3 coding region, and E4 coding region and includes one or more heterologous nucleotide sequences in the deleted E1 coding region.

The preferred recombinant adenoviruses of the present invention comprise viral DNA sequences that have reduced homology with the adenoviral DNA sequences in the recombinant adenovirus production cell, which reduces the possibility of the viral genome recombining with the cellular DNA to produce RCAs.

In certain embodiments, the quantity of recombinant adenovirus is titrated. Titrating the quantity of the adenovirus in the culture may be performed by techniques known in the art. In a particular embodiment, the concentration of viral particles is determined by the Resource Q assay as described by (Shabram et al., 1997b). As used herein, the term "lysis" refers to the rupture of the virus-containing cells. Lysis may be achieved by a variety of means well known in the art. For example, mammalian cells may be lysed under low pressure (100-200 psi differential pressure) conditions, by homogenization, by microfluidization, or by conventional freeze-thaw methods. Exogenous free DNA/RNA may be removed by degrecombinant adenovirusation with DNAse/RNAse.

Virus-containing cells may be frozen. Virus may be harvested from the virus-containing cells and the medium. In one embodiment, the virus is harvested from both the virus-containing cells and the medium simultaneously. In a particular embodiment, the virus producing cells and medium are subjected to cross-flow microfiltration, for example, as described in U.S. Pat. No. 6,146,891, under conditions to both simultaneously lyse virus-containing cells and clarify the medium of cell debris which would otherwise interfere with virus purification.

As used herein, the term "harvesting" means the collection of the cells containing the recombinant adenovirus from the media and may include collection of the recombinant adenovirus from the media. This may be achieved by conventional methods such as differential centrifugation or chromatographic means. At this stage, the harvested cells may be stored or further processed by lysis and purification to isolate the recombinant virus. For storage, the harvested cells should be buffered at or about physiological pH and frozen at −70° C.

Virus may also be harvested from the virus-containing cells and medium separately. The virus-containing cells may be collected separately from the medium by conventional methods such as differential centrifugation. Harvested cells may be stored frozen or further processed by lysis to liberate the virus. Virus may be harvested from the medium by chromatographic means. Exogenase free DNA/RNA may be removed by degrecombinant adenovirusation with DNAse/RNAse, such as BENZONASE (American International Chemicals, Inc.).

The virus harvest may be further processed to concentrate the virus by methods such as ultrafiltration or tangential flow filtration, for example, as described in U.S. Pat. Nos. 6,146,891; 6,544,769 and 6,783,983.

As used herein, the term "recovering" means the isolation of a substantially pure population of recombinant virus particles from the lysed producer cells and optionally from the supernatant medium. Viral particles produced in the cell cultures of the present invention may be isolated and purified by any method which is commonly known in the art. Conventional purification techniques such as chromatographic or differential density grecombinant adenovirusient centrifugation methods may be employed. For example, the viral particles may be purified by cesium chloride grecombinant adenovirusient purification, column or batch chromatography, diethylaminoethyl (DEAE) chromatography (Haruna et al., 1961; Klemperer and Pereira, 1959; Philipson, 1960), hydroxyapatite chromatography (U.S. Patent Application Publication Number US2002/0064860) and chromatography using other resins such as homogeneous cross-linked polysaccharides, which include soft gels (e.g., agarose), macroporous polymers based on synthetic polymers, which include perfusion chromatography resins with large "throughpores", "tentacular" sorbents, which have tentacles that were designed for faster interactions with proteins (e.g., fractogel) and materials based on a soft gel in a rigid shell, which exploit the high capacity of soft gels and the rigidity of composite materials (e.g., Ceramic HyperD® F) (Broschetti, 1994; Rodrigues, 1997). In the preferred practice of the invention, the virus is purified by column chromatography in substantial accordance with the process of (Huyghe et al., 1995b) as described in Shabram, et al., U.S. Pat. No. 5,837,520 issued Nov. 17, 1998; see also U.S. Pat. No. 6,2661,823, the disclosures of which are herein incorporated by reference.

The recombinant adenovirus production cell lines producing virus may be cultured in any suitable vessel which is known in the art. For example, cells may be grown and the infected cells may be cultured in a biogenerator or a bioreactor. Generally, "biogenerator" or "bioreactor" means a culture tank, generally made of stainless steel or glass, with a volume of 0.5 liter or greater, comprising an agitation system, a device for injecting a stream of $CO_2$ gas and an oxygenation device. Typically, it is equipped with probes measuring the internal parameters of the biogenerator, such as the pH, the dissolved oxygen, the temperature, the tank pressure or certain physicochemical parameters of the culture (for instance the consumption of glucose or of glutamine or the production of lactate and ammonium ions). The pH, oxygen, and temperature probes are connected to a bioprocessor which permanently regulates these parameters. In other embodiments, the vessel is a spinner flask, a roller bottle, a shaker flask or in a flask with a stir bar providing mechanical agitation. In another embodiment, the vessel is a WAVE Bioreactor (WAVE Biotech, Bridgewater, N.J., U.S.A.).

Recombinant adenoviruses may be propagated in the recombinant adenovirus production cell lines of the invention. Virus may be produced by culturing the cells; optionally adding fresh growth medium to the cells; inoculating the cells with the virus; incubating the inoculated cells; optionally adding fresh growth medium to the inoculated cells; and optionally harvesting the virus from the cells and the medium. Typically, when the concentration of viral particles, as determined by conventional methods, such as high performance liquid chromatography using a Resource Q column, as described in (Shabram et al., 1997b), begins to plateau, the harvest is performed.

Proteins produced by recombinant adenoviruses grown in the recombinant adenovirus production cell lines of the invention (e.g., adenovirus comprising a deletion of the E1A and E1B coding regions and comprising a heterologous nucleotide sequence, or adenovirus comprising a deletion of E1A, E1B and E2B polymerase coding regions and comprising a heterologous nucleotide sequence, adenovirus comprising a deletion of the E1A, E1B, E2B and E3 coding regions and comprising a heterologous nucleotide sequence, or adenovirus comprising a deletion of E1A, E1B, E2B polymerase coding regions, E3 and E4 coding regions and comprising a heterologous nucleotide sequence) may also be isolated and purified. Proteins, polypeptides and peptides may be purified by standard methods, including, but not limited to, salt or alcohol precipitation, affinity, preparative disc-gel electrophoresis, isoelectric focusing, high pressure liquid chromatography (HPLC), reversed-phase HPLC, gel filtration, cation and anion exchange and partition chromatography, and countercurrent distribution. Such purification methods are well known in the art and are disclosed, e.g., in "Guide to Protein Purification", Methods in Enzymology, Vol. 182, M. Deutscher, Ed., 1990, Academic Press, New York, N.Y.

5.5 Utility of Recombinant Adenovirus

The recombinant adenoviruses of the invention can be used in vitro to express proteins, polypeptides and peptides of interest. The recombinant adenoviruses of the invention can also be used in gene therapy. The recombinant adenoviruses can be used for in vivo or ex vivo gene therapy. For in vivo gene therapy, recombinant adenovirus is directly administered to a subject. For ex vivo gene therapy, cells are infected with the recombinant adenovirus in vitro and then the infected cells are transplanted into the subject. In a specific embodiment, the recombinant adenovirus is directly administered in vivo, where a protein of interest is expressed.

In one embodiment, the present invention comprises a method for the treatment of cancer comprising administering a therapeutically effective amount of a recombinant adenovirus vector of the invention comprising one or more nucleotide sequences encoding a therapeutic protein to a subject. The recombinant adenovirus vectors of the invention comprising one or more nucleotide sequences encoding a therapeutic protein may be delivered to any cancerous tissue or organ using any delivery method known in the art, including, but not limited to intratumoral or intravesical administration. Examples of cancers that may be treated by the methods include, but are not limited to, carcinoma of the bladder and upper respiratory tract, vulva, cervix, vagina or bronchi; local metastatic tumors of the peritoneum; broncho-alveolar carcinoma; pleural metastatic carcinoma; carcinoma of the mouth and tonsils; carcinoma of the nasopharynx, nose, larynx, oesophagus, stomach, ovary, prostate colon and rectum, gallbladder, or skin; or melanoma or hematological cancers such as leukemia. By way of example, and not limitation, a recombinant adenovirus of the present invention comprising an expression cassette encoding interferon alpha 2b can be used in the treatment of bladder cancer. In one embodiment the recombinant adenovirus vector shown in FIG. 6 is used in the methods described herein to treat bladder cancer.

Non-limiting examples of therapeutically effective amounts of the recombinant adenovirus vectors of the invention comprising one or more nucleotide sequences encoding a therapeutic protein are in the range of between about $1 \times 10^8$ particles/ml to about $1 \times 10^{12}$ particles/ml or between about $1 \times 10^9$ particles/ml to about $1 \times 10^{11}$ particles/ml. In one embodiment, the recombinant adenovirus vector shown in FIG. 6 is administered to a subject with bladder cancer in the range of between about $1 \times 10^8$ particles/ml to about $1 \times 10^{12}$ particles/ml or between about $1 \times 10^9$ particles/ml to about $1 \times 10^{11}$ particles/ml.

In another embodiment, a cell is infected with a recombinant adenovirus and the resulting recombinant cell is administered to a subject. The resulting recombinant cells can be delivered to a subject by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art. In accordance with the invention, any cells which can be infected with a recombinant adenovirus can be for purposes of gene therapy. Non-limiting examples include epithelial cells (e.g., respiratory epithelial cells), endothelial cells, keratinocytes, fibroblasts, muscle cells, hepatocytes, blood cells (such as T lymphocytes, B lymphocytes, monocytes, macrophages, neutrophils, eosinophils, megakaryocytes, granulocytes), and various stem or progenitor cells (in particular, hematopoietic stem or progenitor cells, e.g., as obtained from bone marrow, umbilical cord blood, peripheral blood, fetal liver, etc.). In a preferred embodiment, the cell used for gene therapy is autologous to the subject. In an embodiment in which recombinant cells are used in gene therapy, the proteins encoded by the genome of the recombinant adenovirus are expressible by the cells or their progeny, and the recombinant cells are then administered in vivo for therapeutic effect.

The recombinant adenovirus of the present invention may be used to immunize a subject. For example, the recombinant adenovirus may be used to generate antibodies against a heterologous antigen encoded by the recombinant adenovirus. The amount of recombinant adenovirus to be used to immunize a subject and the immunization schedule will be determined by a physician skilled in the art and will be administered by reference to the immune response and antibody titers of the subject.

The antibodies generated against an antigen by immunization with a recombinant adenovirus may used in diagnostic immunoassays, passive immunotherapy, and generation of anti-idiotypic antibodies. The generated antibodies may be isolated by standard techniques known in the art (e.g., immunoaffinity chromatography, centrifugation, precipitation, etc.) and used in diagnostic immunoassays. The antibodies may also be used to monitor treatment and/or disease progression. Any immunoassay system known in the art may be used for this purpose including, but not limited to, competitive and noncompetitive assay systems using techniques such as recombinant adenovirusioimmunoassays, ELISA (enzyme-linked immunosorbent assays), "sandwich" immunoassays, precipitin reactions, gel diffusion precipitin reactions, immunodiffusion assays, agglutination assays, complement-fixation assays, immunorecombinant adenovirusiometric assays, fluorescent immunoassays, protein A immunoassays and immunoelectrophoresis assays, to name but a few.

The recombinant adenoviruses of the present invention can be used to produce antibodies for use in passive immunotherapy, in which short-term protection of a subject is achieved by the administration of pre-formed antibody directed against a heterologous antigen. The antibodies generated by the recombinant adenovirus of the present invention can also be used in the production of anti-idiotypic antibody. The anti-idiotypic antibody can then in turn be used for immunization, in order to produce a subpopulation of antibodies that bind the initial antigen (Jerne, 1974; Jerne et al., 1982).

In certain embodiments, the antibody produced by immunization with a recombinant adenovirus is modified prior to administration to a subject. For example, the antibody may be humanized and/or affinity matured.

5.6 Compositions and Methods of Administering Recombinant Adenovirus

The invention encompasses compositions comprising a recombinant adenovirus (preferably, replication-defective recombinant adenovirus) generated by the methods of the invention. In a preferred embodiment, the compositions are pharmaceutical compositions suitable for administration to a subject.

The pharmaceutical compositions of the present invention comprise an effective amount of recombinant adenovirus, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeiae for use in animals, and more particularly in humans. The term "carrier" refers to a diluent, adjuvant, excipient, or vehicle with which the pharmaceutical composition is administered. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. These compositions can take the form of solutions, suspensions, emulsion, tablets, pills, capsules, powders, sustained-release formulations and the like. These compositions can be formulated as a suppository. Oral formulation can include standard carriers such as pharmaceutical grecombinant adenoviruses of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain an effective amount of recombinant adenovirus, preferably in purified form, together with a suitable amount of carrier so as to provide the form for proper administration to the patient. The formulation should suit the mode of administration.

The amount of the pharmaceutical composition of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

Non-limiting examples of therapeutically effective amounts of the recombinant adenovirus vectors of the invention comprising one or more nucleotide sequences encoding a therapeutic protein are in the range of between about $1\times10^8$ particles/ml to about $1\times10^{12}$ particles/ml or between about $1\times10^9$ particles/ml to about $1\times10^{11}$ particles/ml.

By way of example, and not limitation for the treatment of superficial bladder cancer in a subject, course of treatment comprising a dose of from $1\times\times10^{10}$.particles/ml to about $1\times10^{12}$.particles/ml, most preferably approximately $1\times10^{11}$ particles/ml encoding interferon alpha.2b in a volume of approximately 100 ml is instilled intravesically for a period of approximately one hour. By way of example, and not limitation, an alternate course of treatment may comprise a dose of from $1\times\times10^{10}$.particles/ml to about $1\times10^{12}$.particles/ml most preferably approximately $1\times10^{11}$ particles/ml encoding interferon alpha2b in a volume of approximately 100 ml is instilled intravesically for a period of approximately one hour followed by a second substantially equivalent dose within 7 days, 5 days, 4 days, 3 days, 2 days or on consecutive days following the first dose. Each course of treatment is repeatable, depending on the course of disease progression. In the case of intravesically administered recombinant vectors for the treatment of bladder cancer, optimal interferon gene expression is generally observed when the courses of treatment are distanced by at least 14 days, more preferably about 30 days, and most preferably about 90 days.

Methods of administration of the compositions include, but are not limited to, intradermal, intramuscular, intraperitoneal, intravenous, subcutaneous, intranasal, epidural, and oral routes. The pharmaceutical compositions of the present invention may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the lungs by any suitable route. Pulmonary administration can be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of a malignant tumor or neoplastic or pre-neoplastic tissue. In another embodiment the administration can be intravesicular administration.

In another embodiment, the pharmaceutical composition can be delivered in a controlled release system. In one embodiment, a pump may be used (Buchwald et al., 1980; Langer, 1983; Saudek et al., 1989; Sefton, 1987). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); (Langer and Peppas, 1983); (During et al., 1989; Howard et al., 1989; Levy et al., 1985) In yet another embodiment, a controlled release system can be placed in proximity of the composition's target, i.e., the lung, thus requiring only a fraction of the systemic dose (see, e.g., Goodson, 1984, in Medical Applications of Controlled Release, supra, vol. 2, pp. 115-138). Other controlled release systems are discussed in the review by (Langer, 1990).

In a specific embodiment, a composition of the invention is a vaccine or immunizing composition comprising a recombinant adenovirus (preferably, replication-defective recombinant adenovirus) generated by the methods of the invention, and a suitable excipient. Many methods may be used to introduce the vaccine compositions, these include but are not limited to intranasal, intratracheal, oral, intradermal, intramuscular, intraperitoneal, intravenous, and subcutaneous routes. It may be preferable to introduce the recombinant adenovirus vaccine composition via the natural route of infection of adenovirus.

Non-limiting examples of therapeutically effective amounts of the recombinant adenovirus vectors of the invention comprising one or more nucleotide sequences encoding a therapeutic protein are in the range of between about $1 \times 10^8$ particles/ml to about $1 \times 10^{12}$ particles/ml or between about $1 \times 10^9$ particles/ml to about $1 \times 10^{11}$ particles/ml.

In some embodiments it may be desirable to administer the recombinant adenovirus vector in conjunction with enhancing agents that facilitate the transfer of the nucleic acid encoding a therapeutic protein, for example interferon, to a target cell, such as, for example, a cancer cell. Examples of such delivery enhancing agents include detergents, alcohols, glycols, surfactants, bile salts, heparin antagonists, cyclooxygenase inhibitors, hypertonic salt solutions, and acetates. Alcohols include for example the aliphatic alcohols such as ethanol, N-propanol, isopropanol, butyl alcohol, acetyl alcohol. Glycols include glycerine, propyleneglycol, polyethyleneglycol and other low molecular weight glycols such as glycerol and thioglycerol. Acetates such as acetic acid, gluconic acid, and sodium acetate are further examples of delivery-enhancing agents. Hypertonic salt solutions like 1M NaCl are also examples of delivery-enhancing agents. Bile salts such as taurocholate, sodium tauro-deoxycholate, deoxycholate, chenodesoxycholate, glycocholic acid, glycochenodeoxycholic acid and other astringents such as silver nitrate may be used. Heparin-antagonists like quaternary amines such as protamine sulfate may also be used. Anionic, cationic, zwitterionic, and nonionic detergents may also be employed to enhance gene transfer. Exemplary detergents include but are not limited to taurocholate, deoxycholate, taurodeoxycholate, cetylpyridium, benalkonium chloride, Zwittergent 3-14 detergent, CHAPS (3-[(3-Cholamidopropyl)dimethylammoniol]-1-propanesulfon-ate hydrate), Big CHAP, Deoxy Big CHAP, Triton-X-100 detergent, C12E8, Octyl-B-D-Glucopyranoside, PLURONIC-F68 detergent, Tween 20 detergent, and TWEEN 80 detergent (CalBiochem Biochemicals). Particularly preferred enhancing agents and methods are described in Engler et al., U.S. Pat. No. 6,312,681, issued Nov. 6, 2001, Engler et al., U.S. Pat. No. 6,165,779, issued Dec. 26, 2000, and Engler et al., U.S. Pat. No. 6,392,069, issued May 21, 2002, the entire teachings of which are herein incorporated by reference. A particularly preferred enhancing agent useful in the practice of the present invention is a compound termed Syn3 of the Formula I in U.S. Pat. No. 6,392,069. Additional enhancing agents useful in the practice of the present invention include, but are not limited to, the compounds of the Formulas II, III, IV, and V and their pharmaceutically acceptable salts in WO2004/108088. By way of example, and not limitation, the enhancing agents may be administered concomitant with the vector or prior to the administration of the vector.

The compositions and methods of the present invention may be practiced alone or in combination with conventional chemotherapeutic agents or treatment regimens. Examples of such chemotherapeutic agents include inhibitors of purine synthesis (e.g., pentostatin, 6-mercaptopurine, 6-thioguanine, methotrexate) or pyrimidine synthesis (e.g., Pala, azarbine), the conversion of ribonucleotides to deoxyribonucleotides (e.g., hydroxyurea), inhibitors of dTMP synthesis (5-fluorouracil), DNA damaging agents (e.g., radiation, bleomycines, etoposide, teniposide, dactinomycine, daunorubicin, doxorubicin, mitoxantrone, alkylating agents, mitomycin, cisplatin, procarbazine) as well as inhibitors of microtubule function (e.g., vinca alkaloids and colchicine). Chemotherapeutic treatment regimens refers primarily to nonchemical procedures designed to ablate neoplastic cells such as radiation therapy. These chemotherapeutic agents may be administered separately or may be included with the formulations of the present invention for co-administration. The present invention may also be practiced in combination with conventional immunotherapeutic treatment regiments such as BCG in the case of superficial bladder cancer.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Patents, patent applications, publications, product descriptions, and protocols are cited throughout this application, the disclosures of which are incorporated herein by reference in their entireties.

PUBLICATIONS

Amalfitano, A., Hauser, M. A., Hu, H., Serra, D., Begy, C. R., and Chamberlain, J. S. (1998). Production and characterization of improved adenovirus vectors with the E1, E2b, and E3 genes deleted. J Virol 72, 926-933.

Appleby, C. E., Kingston, P. A., David, A., Gerdes, C. A., Umana, P., Castro, M. G., Lowenstein, P. R., and Heagerty, A. M. (2003). A novel combination of promoter and enhancers increases transgene expression in vascular smooth muscle cells in vitro and coronary arteries in vivo after adenovirus-mediated gene transfer. Gene Ther 10, 1616-1622.

Bell, A. C., West, A. G., and Felsenfeld, G. (1999). The protein CTCF is required for the enhancer blocking activity of vertebrate insulators. Cell 98, 387-396.

Bell, A. C., West, A. G., and Felsenfeld, (G. (2001). Insulators and boundaries: versatile regulatory elements in the eukaryotic. Science 291, 447-450.

Benedict, W. F., Tao, Z., Kin C. S. Zhang, X., Zhou, J. H., Adam, L., McConkey, D. J., Papageorgiou, A., Munsell, M., Philopena, J., et al. (2004). Intravesical Ad-IFNalpha causes marked regression of human bladder cancer growing orthotopically in nude mice and overcomes resistance to IFN-alpha protein. Mol Ther 10, 525-532.

Benoist, C., and Chambon, P. (1981). In vivo sequence requirements of the SV40 early promotor region. Nature 290, 304-310.

Berkner, K. L., and Sharp, P. A. (1983). Generation of adenovirus by transfection of plasmids. Nucleic Acids Res 11, 6003-6020.

Berkner, K. L., and Sharp, P. A. (1984). Expression of dihydrofolate reductase, and of the adjacent EIb region, in an Ad5-dihydrofolate reductase recombinant virus. Nucleic Acids Res 12, 1925-1941.

Brasset, E., and Vaury, C. (2005). Insulators are fundamental components of the eukaryotic genomes. Heredity 94, 571-576.

Breckpot, K., Dullaers, M., Bonehill, A., van Meirvenne, S., Heirman, C., de Greef, C., van der Bruggen, P., and Thielemans, K. (2003). Lentivirally transduced dendritic cells as a tool for cancer immunotherapy. J Gene Med 5, 654-667.

Brinster, R. L., Chen. H. Y., Warren, R. Sarthy, A., and Palmiter, R. D. (1982). Regulation of metallothionein-thymidine kinase fusion plasmids injected into mouse eggs. Nature 296, 39-42.

Broschetti, E. (1994). Advanced sorbents for preparative protein separation purposes. j chromatogr 658, 207-236.

Brough, D. E., Cleghon, V., and Klessig, D. F. (1992). Construction, characterization, and utilization of cell lines which inducibly express the adenovirus DNA-binding protein. Virology 190, 624-634.

Brun, S., Faucon-Biguet, N., and Mallet, J. (2003). Optimization of transgene expression at the posttranscriptional level in neural cells: implications for gene therapy. Mol Ther 7, 782-789.

Buchwald, H., Rohde, T. D., Schneider, P. D., Varco, R. L., and Blackshear. P. J. (1980). Long-term, continuous intravenous heparin administration by an implantable infusion pump in ambulatory patients with recurrent venous thrombosis. Surgery 88, 507-516.

Cheng, W. S., Kraaij, R., Nilsson, B., van der Weel, L., de Ridder, C. M., Totterman, T. H., and Essand, M. (2004). A novel TARP-promoter-based adenovirus against hormone-dependent and hormone-refractory prostate cancer. Mol Ther 10, 355-364.

Choi, T., Huang, M., Gorman, C., and Jaenisch, R. (1991). A generic intron increases gene expression in transgenic mice. Mol Cell Biol 11, 3070-3074.

Connor, R. J., Anderson, J. M., Machemer, T., Maneval, D. C., and Engler, H. (2005). Sustained intravesical interferon protein exposure is achieved using an adenoviral-mediated gene delivery system: a study in rats evaluating dosing regimens. Urology 66, 224-229.

Davison, A. J., Benko, M., and Harrach, B. (2003). Genetic content and evolution of adenoviruses. J Gen Virol 84, 2895-2908.

Demers, G. W., Johnson, D. E., Machemer, T., Looper, L. D., Batinica, A., Beltran, J. C., Sugarman, B. J., and Howe, J. A. (2002a). Tumor growth inhibition by interferon-alpha using PEGylated protein or adenovirus gene transfer with constitutive or regulated expression. Mol Ther 6, 50-56.

Demers, G. W., Sugarman, B. J., Beltran, J. C., Westreich, L. N., Ahmed, C. M., Lau, J. Y., Hong, Z., Lanford, R. E., and Maneval, D. C. (2002b). Interferon-alpha2b secretion by adenovirus-mediated gene delivery in rat, rabbit, and chimpanzee results in similar pharmacokinetic profiles. Toxicol Appl Pharmacol 180, 36-42.

Di Simone, P., Di Leonardo, A., Costanzo, G., Melfi, R., and Spinelli, G. (2001). The sea urchin sns insulator blocks CMV enhancer following integration in human cells. Biochem Biophys Res Commun 284, 987-992.

Donello, J. E., Loeb, J. E., and Hope, T. J. (1998). Woodchuck hepatitis virus contains a tripartite posttranscriptional regulatory element. J Virol 72, 5085-5092.

Dunn, K. L., and Davie, J. R. (2003). The many roles of the transcriptional regulator CTCF, Biochem Cell Biol 81, 161-167.

Dunn, K L., Zhao, H., and Davie, J. R. (2003). The insulator binding protein CTCF associates with the nuclear matrix. Exp Cell Res 288, 218-223.

During, M. J., Freese, A., Sabel, B. A., Saltzman, W. M., Deutch, A., Roth, R. H., and Langer, R. (1989). Controlled release of dopamine from a polymeric brain implant: in vivo characterization. Annals of neurology 25, 351-356.

Emery, D. W., Yannaki, E., Tubb, J., Nishino, T., Li, Q., and Stamatoyannopoulos, G. (2002). Development of virus vectors for gene therapy of beta chain hemoglobinopathies: flanking with a chromatin insulator reduces gamma-globin gene silencing in vivo. Blood 100, 2012-2019.

Farrell, C. M., West, A. G., and Felsenfeld, G. (2002). Conserved CTCF insulator elements flank the mouse and human beta-globin loci. Mol Cell Biol 22, 3820-3831.

Glover, C. P., Bienemann, A. S., Heywood, D. J., Cosgrave, A. S., and Uney, J. B. (2002). Adenoviral-mediated, high-level, cell-specific transgene expression: a SYNI-WPRE cassette mediates increased transgene expression with no loss of neuron specificity. Mol Ther 5, 509-516.

Glover, C. P., Bienemann, A. S., Hopton, M., Harding, T. C., Kew, J. N., and Uney, J. B. (2003). Long-term transgene expression can be mediated in the brain by adenoviral vectors when powerful neuron-specific promoters are used. J Gene Med 5, 554-559.

Graham, F. L., and van der Eb, A. J. (1973). Transformation of rat cells by DNA of human adenovirus 5. Virology 54, 536-539.

Gropp, M., Itsykson, P., Singer, O., Ben-Hur, T., Reinhartz, F., Galun, E., and Reubinoff, B. E. (2003). Stable genetic modification of human embryonic stem cells by lentiviral vectors. Mol Ther 7, 281-287.

Hardy, S., Kitamura, M., Harris-Stansil, T., Dai, Y., and Phipps, M. L. (1997). Construction of adenovirus vectors through Cre-lox recombination. J Virol 71, 1842-1849.

Haruna, I., Yaoi, H., Kono, R., and Watanabe, I. (1961). Separation of adenovirus by chromatography on DEAE-Cellulose. Virology 13, 264-267.

Hermening, S., Kugler, S., Bahr, M., and Isenmann, S. (2004). Increased protein expression from adenoviral shuttle plasmids and vectors by insertion of a small chimeric intron sequence. J Virol Methods 122, 73-77.

Howard, M. A., 3rd. Gross, A., Grady, M. S., Langer, R. S., Mathiowitz, E., Winn, H. R., and Mayberg, M. R. (1989). Intracerebral drug delivery in rats with lesion-induced memory deficits. Journal of neurosurgery 71, 105-112.

Huang, Z. M., and Yen, T. S. (1994). Hepatitis B virus RNA element that facilitates accumulation of surface gene transcripts in the cytoplasm. J Virol 68, 3193-3199.

Huyghe, B. G., Liu, X., Sutjipto, S., Sugarman, B. J., Horn, M. T., Shepard, H. M., Scandella, C. J., and Shabram, P. (1995a). Purification of a type 5 recombinant adenovirus encoding human p53 by column chromatography. In Hum Gene Ther, pp. 1403-1416.

Huyghe, B. G., Liu, X, Sutjipto, S., Sugarman, B. J., Horn, M. T., Shepard, H. M., Scandella, C. J., and Shabram, P. (1995b). Purification of a type 5 recombinant adenovirus encoding human p53 by column chromatography. Hum Gene Ther 6, 1403-1416.

Iqbal Ahmed, C. M., Johnson, D. E., Demers, G. W., Engler, H., Howe, J. A., Wills, K. N., Wen, S. F., Shinoda, J., Beltran, J., Nodelman, M., et al. (2001). Interferon alpha2b gene delivery using adenoviral vector causes inhibition of tumor growth in xenograft models from a variety of cancers. Cancer Gene Ther 8, 788-795.

Jakobsson, J., Rosenqvist, N., Thompson, L., Barraud, P., and Lundberg, C. (2004). Dynamics of transgene expression in a neural stem cell line transduced with lentiviral vectors incorporating the cHS4 insulator. Exp Cell Res 298, 611-623.

Jerne, N. K. (1974). Towards a network theory of the immune system. Ann Immunol (Paris) 125C, 373-389.

Jerne, N. K., Roland, J., and Cazenave, P. A. (1982). Recurrent idiotopes and internal images. Embo J 1, 243-247.

Kanduri, M., Kanduri, C., Mariano, P., Vostrov, A. A., Quitschke, W., Lobanenkov, V., and Ohlsson, R. (2002). Multiple nucleosome positioning sites regulate the CTCF-mediated insulator function of the H19 imprinting control region. Mol Cell Biol 22, 3339-33.

Klemperer, H. G., and Pereira. H. G. (1959). Study of adenovirus antigens fractionated by chromatography on DEAE-cellulose. Virology 9, 536-545.

Kochanek, S., Clemens, P. R., Mitani, K., Chen, H. H., Chan, S., and Caskey, C. T. (1996). A new adenoviral vector: Replacement of all viral coding sequences with 28 kb of DNA independently expressing both full-length dystrophin and beta-galactosidase. Proc Natl Acad Sci USA 93, 5731-5736.

Kumar-Singh, R., and Chamberlain, J. S. (1996). Encapsidated adenovirus minichromosomes allow delivery and expression of a 14 kb dystrophin cDNA to muscle cells. Hum Mol Genet 5, 913-921.

Langer, R. (1983). Implantable controlled release systems. Pharmacol Ther 21, 35-51.

Langer, R. (1990). New methods of drug delivery. Science 249, 1527-1533.

Langer, R., and Peppas, N. J. (1983). Chemical and physical structure of polymers as carriers for controlled release of bioactive agents: a review. J Macromol Sci Rev Macromol Chem Phys 23, 61-126.

Lee, A. H., Suh, Y. S., Sung, J. H., Yang, S. H., and Sung, Y. C. (1997). Comparison of various expression plasmids for the induction of immune response by DNA immunization. Mol Cells 7, 495-501.

Levy, R. J., Wolfrum, J., Schoen, F. J., Hawley, M. A., Lund, S. A., and Langer, R. (1985). Inhibition of calcification of bioprosthetic heart valves by local controlled-release diphosphonate. Science 228, 190-192.

Lewis, A., and Murrell, A. (2004). Genomic imprinting: CTCF protects the boundaries. Curr Biol 14, R284-286.

Liu, X., and Mertz, J. E. (1995). HnRNP L binds a cis-acting RNA sequence element that enables intron-dependent gene expression. Genes Dev 9, 1766-1780.

Lutz, M., Burke, L. J., Barreto, G., Goeman, F., Greb, H., Arnold, R., Schultheiss, H., Brehm, A., Kouzarides, T., Lobanenkov, V., and Renkawitz, R. (2000). Transcriptional repression by the insulator protein CTCF involves histone deacetylases. Nucleic Acids Res 28, 1707-1713.

Mangeot, P. E., Duperrier, K., Negre, D., Boson, B., Rigal, D., Cosset, F. L., and Darlix, J. L. (2002). High levels of transduction of human dendritic cells with optimized SIV vectors. Mol Ther 5, 283-290.

Martin-Duque, P., Jezzard, S., Kaftansis, L., and Vassaux, G. (2004). Direct comparison of the insulating properties of two genetic elements in an adenoviral vector containing two different expression cassettes. Hum Gene Ther 15, 995-1002.

McCutchan, J. H., and Pagano, J. S. (1968). Enchancement of the infectivity of simian virus 40 deoxyribonucleic acid with diethylaminoethyl-dextran. J Natl Cancer Inst 41, 351-357.

Mitani, K., Graham, F. L., Caskey, C. T., and Kohanek, S. (1995). Rescue, propagation, and partial purification of a helper virus-dependent adenovirus vector. Proc Natl Acad Sci USA 92, 3854-3858.

Mukhopadhyay, R., Yu, W., Whitehead, J., Xu, J., Lezcano, M., Pack, S., Kanduri, C., Kanduri, M., Ginjala, V., Vostrov, A., et al. (2004). The binding sites for the chromatin insulator protein CTCF map to DNA methylation-free domains genome-wide. Genome Res 14, 1594-1602.

Pannell, D., and Ellis, J. (2001). Silencing of gene expression: implications for design of retrovirus vectors. Rev Med Virol 11, 205-217.

Parks, R. J., Chen, L., Anton, M., Sankar, U., Rudnicki, M. A., and Graham, F. L. (1996). A helper-dependent adenovirus vector system: removal of helper virus by Cre-mediated excision of the viral packaging signal. Proc Natl Acad Sci USA 93, 13565-13570.

Philipson, L. (1960). Separation on DEAE cellulose of components associated with adenovirus reproduction. Virology 10, 459-465.

Pluta, K., Luce, M. J., Bao, L., Agha-Mohammadi, S., and Reiser, J. (2005). Tight control of transgene expression by lentivirus vectors containing second-generation tetracycline-responsive promoters. J Gene Med.

Puthenveetil, G., Scholes, J., Carbonell, D., Qureshi, N., Xia, P., Zeng, L., Li, S., Yu, Y., Hiti, A. L., Yee, J. K., and Malik, P. (2004). Successful correction of the human beta-thalassemia major phenotype using a lentiviral vector. Blood 104, 3445-3453.

Qu, Z., Thottassery, J. V., Van Ginkel, S., Manuvakhova, M., Westbrook, L., Roland-Lazenby, C., Hays, S., and Kern, F. G. (2004). Homogeneity and long-term stability of tetracycline-regulated gene expression with low basal activity by using the rtTA2S-M2 transactivator and insulator-flanked reporter vectors. Gene 327, 61-73.

Recillas-Targa, F., Pikaart, M. J., Burgess-Beusse, B., Bell, A. C., Litt, M. D., West, A. G., Gaszner, M., and Felsenfeld, G. (2002). Position-effect protection and enhancer blocking by the chicken beta-globin insulator are separable activities. Proc Natl Acad Sci USA 99, 6883-6888.

Rincon-Arano, H., and Recillas-Targa, F. (2004). Sustained heterologous transgene expression in mammalian and avian cell lines. Methods Mol Biol 267, 435-450.

Robert, D., Mahon, F. X., Richard, E., Etienne, G., de Verneuil, H., and Moreau-Gaudry, F. (2003). A SIN lentiviral vector containing PIGA cDNA allows long-term phenotypic correction of CD34+-derived cells from patients with paroxysmal nocturnal hemoglobinuria. Mol Ther 7, 304-316.

Rodrigues, A. E. (1997). Permeable packings and perfusion chromatography in protein separation. J Chromatogr B Biomed Sci Appl 699, 47-61.

Saitoh, N., Bell, A. C., Recillas-Targa, F., West, A. G., Simpson, M., Pikaart, M., and Felsenfeld, G. (2000). Structural and functional conservation at the boundaries of the chicken beta-globin domain. Embo J 19, 2315-2322.

Saudek, C. D., Selam, J. L., Pitt, H. A., Waxman, K., Rubio, M, Jeandidier, N., Turner, D., Fischell, R. E., and Charles, M. A. (1989). A preliminary trial of the programmable implantable medication system for insulin delivery. N Engl J Med 321, 574-579.

Schwenter, F., Deglon, N., and Aebischer, P. (2003). Optimization of human erythropoietin secretion from MLV-infected human primary fibroblasts used for encapsulated cell therapy. J Gene Med 5, 246-257.

Sefton, M. V. (1987). Implantable pumps. Crit Rev Biomed Eng 14, 201-240.

Shabram, P. W., Giroux, D. D., Goudreau, A. M., Gregory, R. J., Horn, M. T., Huyghe, B. G., Liu, X., Nunnally, M. H., Sugarman. B. J., and Sutjipto, S. (1997a). Analytical anion-exchange HPLC of recombinant type-5 adenoviral particles. In Hum Gene Ther, pp. 453-465.

Shabram, P. W., Giroux, D. D., Goudreau, A. M., Gregory, R. J., Horn M. T., Huyghe B. G., Liu, X., Nunnally, M. H., Sugarman, B. J., and Sutjipto, S. (1997b). Analytical anion-exchange HPLC of recombinant type-5 adenoviral particles. Hum Gene Ther 8, 453-465.

Simon, R. H., Engelhardt, J. F., Yang, Y., Zepeda, M., Weber-Pendleton, S., Grossman, M., and Wilson, J. M. (1993). Adenovirus-mediated transfer of the CFTR gene to lung of nonhuman primates: toxicity study. Hum Gene Ther 4, 771-780.

Steinwaerder, D. S., and Lieber, A. (2000). Insulation from viral transcriptional regulatory elements improves inducible transgene expression from adenovirus vectors in vitro and in vivo. Gene Ther 7, 556-567.

Szabo, P. E., Tang, S. H., Reed, M. R., Silva, F. J., Tsark, W. M., and Mann, J. R. (2002). The chicken beta-globin insulator element conveys chromatin boundary activity but not imprinting at the mouse Igf2/H19 domain. Development 129, 897-904.

Takada, T., Iida, K., Akasaka, K., Yasue, H., Torii, R., Tsujimoto, G., Taira, M., and Kimura, H. (2000). Evaluation of heterologous insulator function with regard to chromosomal position effect in the mouse blastocyst and fetus. Mol Reprod Dev 57, 232-237.

Thorvaldsen, J. L., Mann, M. R., Nwoko, O., Duran, K. L., and Bartolomei, M. S. (2002). Analysis of sequence upstream of the endogenous H19 gene reveals elements both essential and dispensable for imprinting. Mol Cell Biol 22, 2450-2462.

Valadez-Graham, V., Razin, S. V., and Recillas-Targa, F. (2004). CTCF-dependent enhancer blockers at the upstream region of the chicken alpha-globin gene domain. Nucleic Acids Res 32, 1354-1362.

Vassaux, G., Hurst, H. C., and Lemoine, N. R. (1999). Insulation of a conditionally expressed transgene in an adenoviral vector. Gene Ther 6, 1192-1197.

Wagner, E. F., Stewart, T. A., and Mintz, B. (1981). The human beta-globin gene and a functional viral thymidine kinase gene in developing mice. Proc Natl Acad Sci USA 78, 5016-5020.

Werner, M., Kraunus, J., Baum, C., and Brocker, T. (2004). B-cell-specific transgene expression using a self-inactivating retroviral vector with human CD19 promoter and viral post-transcriptional regulatory element. Gene Ther 11, 992-100.

Xu, Z. L., Mizuguchi, H., Ishii-Watabe, A., Uchida, E., Mayumi, T., and Hayakawa, T. (2002) Strength evaluation of transcriptional regulatory elements for transgene expression by adenovirus vector. J Control Release 81, 155-163.

Xu, Z. L., Mizuguchi, H., Mayumi, T., and Hayakawa, T. (2003). Woodchuck hepatitis virus post-transcriptional regulation element enhances transgene expression from adenovirus vectors. Biochim Biophys Acta 1621, 266-271.

Yam, P. Y., Li, S., Wu, J., Hu, J., Zaia, J. A., and Yee, J. K. (2002). Design of HIV vectors for efficient gene delivery into human hematopoietic cells. Mol Ther 5, 479-484.

Yamamoto, T., de Crombrugghe, B., and Pastan, I. (1980). Identification of a functional promoter in the long terminal repeat of Rous sarcoma virus. Cell 22, 787-797.

Yannaki, E., Tubb, J., Aker, M., Stamatoyannopoulos, G., and Emery, D. W. (2002). Topological constraints governing the use of the chicken HS4 chromatin insulator in oncoretrovirus vectors. Mol Ther 5, 589-598.

Yao, S., Osborne, C. S., Bharadwaj, R. R., Pasceri, P., Sukonnik, T., Pannell, D., Recillas-Targa, F., West, A. G., and Ellis, J. (2003). Retrovirus silencer blocking by the cHS4 insulator is CTCF independent. Nucleic Acids Res 31, 5317-5323.

Ye, X., Liang, M., Meng, X., Ren, X., Chen, H., Li, Z. Y., Ni, S., Lieber, A., and Hu, F. (2003). Insulation from viral transcriptional regulatory elements enables improvement to hepatoma-specific gene expression from adenovirus vectors, Biochem Biophys Res Commun 307, 759-764.

Youil, R., Toner, T. J., Su, Q., Casimiro, D., Shiver. J. W., Chen, L., Bett, A. J., Rogers, B. M., Burden, E. C., Tang, A., et al. (2003). Comparative analysis of the effects of packaging signal, transgene orientation, promoters, polyadenylation signals, and E3 region on growth properties of first-generation adenoviruses. Hum Gene Ther 14, 1017-1034.

Yusufzai, T. M., and Felsenfeld, G. (2004). The 5'-HS4 chicken beta-globin insulator is a CTCF-dependent nuclear matrix-associated element. Proc Natl Acad Sci USA 101, 8620-8624.

Yusufzai, T. M., Tagami, H., Nakatani, Y., and Felsenfeld, G. (2004). CTCF tethers an insulator to subnuclear sites, suggesting shared insulator mechanisms across species. Mol Cell 13, 291-298.

Zhang, R., Burke, L. J., Rasko, J. E., Lobanenkov, V., and Renkawitz, R. (2004). Dynamic association of the mammalian insulator protein CTCF with centrosomes and the midbody. Exp Cell Res 294, 86-93.

Zhao, H., and Dean, A. (2004). An insulator blocks spreading of histone acetylation and interferes with RNA polymerase it transfer between an enhancer and gene. Nucleic Acids Res 32, 4903-4919.

Zufferey, R., Donello J. E., Trono, D., and Hope. T. J. (1999). Woodchuck hepatitis virus posttranscriptional regulatory element enhances expression of transgenes delivered by retroviral vectors. J Virol 73, 2886-2892.

---

I claim:

1. A recombinant adenoviral vector comprising
   (a) an expression cassette inserted into the E1 region of the adenoviral vector; and
   (b) a mutation that deletes or inactivates the activity of the E2B polymerase, wherein the vector comprises the sequence set forth in SEQ ID NO.:3.

2. A method for treating bladder cancer comprising administering a therapeutically effective amount of a recombinant adenoviral vector comprising
   (a) an expression cassette inserted into the E1 region of the adenoviral vector; and
   (b) a mutation that deletes or inactivates the activity of the E2B polymerase, wherein the vector comprises the sequence set forth in SEQ ID NO.:3 wherein the method comprises intravesicular administration of the vector into the bladder of a subject in need of such treatment, wherein the vector is administered in conjunction with an enhancing agent, wherein the enhancing agent is Syn3.

3. The method of claim 2, wherein the vector is administered in the range of between about $1 \times 10^8$ particles/ml to about $1 \times 10^{12}$ particles/ml.

4. The method of claim 3, wherein the vector is administered in the range of between about $1 \times 10^9$ particles/ml to about $1 \times 10^{11}$ particles/ml.

* * * * *

SEQUENCE LISTING

```
<160> NUMBER OF SEQ ID NOS: 3

<210> SEQ ID NO 1
<211> LENGTH: 2700
<212> TYPE: DNA
<213> ORGANISM: Artificial sequence
<220> FEATURE:
<223> OTHER INFORMATION: T8BF transgene cassette
<220> FEATURE:
<221> NAME/KEY: CDS
<222> LOCATION: (970)..(1536)

<400> SEQUENCE: 1
atgtacgggc cagatatacg cgttgacatt gattattgac tagttattaa tagtaatcaa      60
ttacggggtc attagttcat agcccatata tggagttccg cgttacataa cttacggtaa     120
atggcccgcc tggctgaccg cccaacgacc cccgcccatt gacgtcaata atgacgtatg     180
ttcccatagt aacgccaata gggactttcc attgacgtca atgggtggag tatttacggt     240
aaactgccca cttggcagta catcaagtgt atcatatgcc aagtacgccc cctattgacg     300
tcaatgacgg taaatggccc gcctggcatt atgcccagta catgacctta tgggactttc     360
ctacttggca gtacatctac gtattagtca tcgctattac catgatgatg cggttttggc     420
agtacatcaa tgggcgtgga tagcggtttg actcacgggg atttccaagt ctccacccca     480
ttgacgtcaa tgggagtttg ttttgactag taaatcaacg ggactttcca aaatgtcgta     540
acaactccgc cccattgacg caaatgggcg gtaggcgtgt acggtgggag gtctatataa     600
gcagagctcg tttagtgaac cgtcagataa gcttcgcgcg ggtaccactc tcttcgcatc     660
gctgtctgca agggccagct gttgggctcg cggttgagga caaactcttc gcggtctttc     720
cagtactctt ggatcggaaa cccgtcggcc tccgaacggt actccgccac cgagggacct     780
gagcgagtcc gcatcgaccg gatcggaaaa cctctcgagt ctagaggtaa gtgtcttcct     840
cctgtttcct tcccctgcta ttctgctcaa ccttcctatc agaaactgca gtatctgtat     900
ttttgctagc acaagtttgt acaaaaaagc aggctctttt tttctcttca caggctccag     960 tcgaccacc atg gcc ttg acc ttt gct tta cta gtg gcc ctc ctg gtg ctc    1011
           Met Ala Leu Thr Phe Ala Leu Leu Val Ala Leu Leu Val Leu
            1               5                  10 agc tgc aag agc tcc tgc agc gtg ggc tgt gat ctg cct caa acc cac    1059
Ser Cys Lys Ser Ser Cys Ser Val Gly Cys Asp Leu Pro Gln Thr His
 15                  20                  25                  30 agc ctg ggt agc agg agg acc ttg atg ctc ctg gca cag atg agg aga    1107
Ser Leu Gly Ser Arg Arg Thr Leu Met Leu Leu Ala Gln Met Arg Arg
                 35                  40                  45 atc tct ctt ttc tcc tgc ttg aag gac aga cat gac ttt gga ttt ccc    1155
Ile Ser Leu Phe Ser Cys Leu Lys Asp Arg His Asp Phe Gly Phe Pro
             50                  55                  60 cag gag gag ttt ggc aac cag ttc caa aag gct gaa acc atc cct gtc    1203
Gln Glu Glu Phe Gly Asn Gln Phe Gln Lys Ala Glu Thr Ile Pro Val
         65                  70                  75 ctc cat gag atg atc cag cag atc ttc aat ctc ttc agc aca aag gac    1251
Leu His Glu Met Ile Gln Gln Ile Phe Asn Leu Phe Ser Thr Lys Asp
     80                  85                  90 tca tct gct gct tgg gat gag acc ctc cta gac aaa ttc tac act gaa    1299
```

```
Ser Ser Ala Ala Trp Asp Glu Thr Leu Leu Asp Lys Phe Tyr Thr Glu
 95                 100                 105                 110 ctc tac cag cag ctg aat gac ctg gaa gcc tgt gtg ata cag ggg gtg    1347
Leu Tyr Gln Gln Leu Asn Asp Leu Glu Ala Cys Val Ile Gln Gly Val
                115                 120                 125 ggg gtg aca gag act ccc ctg atg aag gag gac tcc att ctg gct gtg    1395
Gly Val Thr Glu Thr Pro Leu Met Lys Glu Asp Ser Ile Leu Ala Val
            130                 135                 140 agg aaa tac ttc caa aga atc act ctc tat ctg aaa gag aag aaa tac    1443
Arg Lys Tyr Phe Gln Arg Ile Thr Leu Tyr Leu Lys Glu Lys Lys Tyr
        145                 150                 155 agc cct tgt gcc tgg gag gtt gtc aga gca gaa atc atg aga tct ttt    1491
Ser Pro Cys Ala Trp Glu Val Val Arg Ala Glu Ile Met Arg Ser Phe
    160                 165                 170 tct ttg tca aca aac ttg caa gaa agt tta aga agt aag gaa tga        1536
Ser Leu Ser Thr Asn Leu Gln Glu Ser Leu Arg Ser Lys Glu
175                 180                 185 attcctgcag cccgggtcta gaggatccag cggccgctgt taatcaacct ctggattaca  1596
aaatttgtga agattgact  ggtattctta actatgttgc tccttttacg ctatgtggat  1656
acgctgcttt aatgcctttg tatcatgcta ttgcttcccg tatggctttc attttctcct  1716
ccttgtataa atcctggttg ctgtctcttt atgaggagtt gtggcccgtt gtcaggcaac  1776
gtggcgtggt gtgcactgtg tttgctgacg caaccccac  tggttggggc attgccacca  1836
cctgtcagct cctttccggg actttcgctt tcccctccc  tattgccacg cggaactca   1896
tcgccgcctg ccttgcccgc tgctggacag gggctcggct gttgggcact gacaattccg  1956
tggtgttgtc ggggaagctg acgtcctttc catggctgct cgcctgtgtt gccacctgga  2016
ttctgcgcgg gacgtccttc tgctacgtcc ttcggccct  caatccagcg accttcctt   2076
cccgcggcct gctgccggct ctgcggcctc ttccgcgtct tcgccttcgc cctcagacga  2136
gtcggatctc cctttgggcc gcctcccgc  ctgtttctag ttgatccgag ctcggtacca  2196
agcttaagtt taaaccgctg atcagcctcg actgtgcctt ctagttgcca gccatctgtt  2256
gtttgcccct cccccgtgcc ttccttgacc ctggaaggtg ccactcccac tgtccttttcc 2316
taataaaatg aggaaattgc atcgcattgt ctgagtaggt gtcattctat tctgggggt   2376
ggggtggggc aggacagcaa gggggaggat tgggaagaca atagcaggca tgctggggat  2436
gcggtgggct ctatggcttc tgaggcggaa agaaccatct agtgggcaga tcccccaggg  2496
atgtaattac gtcccccccc cgctagggggg cagcaagatc ccccaggat gtaattacgt  2556
ccctccccccg ctaggggggca gcaagatccc ccagggatgt aattacgtcc ctccccgct  2616
aggggcagc aagatccccc agggatgtaa ttacgtccct ccccgctag ggggcagcag   2676
gatcctcgaa tgcatcgcgc tcta                                        2700
```

<210> SEQ ID NO 2
<211> LENGTH: 188
<212> TYPE: PRT
<213> ORGANISM: Artificial sequence
<220> FEATURE:
<223> OTHER INFORMATION: Synthetic Construct

<400> SEQUENCE: 2

Met Ala Leu Thr Phe Ala Leu Leu Val Ala Leu Leu Val Leu Ser Cys
1               5                   10                  15

Lys Ser Ser Cys Ser Val Gly Cys Asp Leu Pro Gln Thr His Ser Leu
            20                  25                  30

Gly Ser Arg Arg Thr Leu Met Leu Leu Ala Gln Met Arg Arg Ile Ser

```
                35                  40                  45
Leu Phe Ser Cys Leu Lys Asp Arg His Asp Phe Gly Phe Pro Gln Glu
 50                  55                  60

Glu Phe Gly Asn Gln Phe Gln Lys Ala Glu Thr Ile Pro Val Leu His
 65                  70                  75                  80

Glu Met Ile Gln Gln Ile Phe Asn Leu Phe Ser Thr Lys Asp Ser Ser
                 85                  90                  95

Ala Ala Trp Asp Glu Thr Leu Leu Asp Lys Phe Tyr Thr Glu Leu Tyr
            100                 105                 110

Gln Gln Leu Asn Asp Leu Glu Ala Cys Val Ile Gln Gly Val Gly Val
        115                 120                 125

Thr Glu Thr Pro Leu Met Lys Glu Asp Ser Ile Leu Ala Val Arg Lys
130                 135                 140

Tyr Phe Gln Arg Ile Thr Leu Tyr Leu Lys Glu Lys Lys Tyr Ser Pro
145                 150                 155                 160

Cys Ala Trp Glu Val Val Arg Ala Glu Ile Met Arg Ser Phe Ser Leu
                165                 170                 175

Ser Thr Asn Leu Gln Glu Ser Leu Arg Ser Lys Glu
            180                 185

<210> SEQ ID NO 3
<211> LENGTH: 32554
<212> TYPE: DNA
<213> ORGANISM: Artificial Sequence
<220> FEATURE:
<223> OTHER INFORMATION: T8BF adenovirus vector

<400> SEQUENCE: 3
taacatcatc aataatatac cttatttggg attgaagcca atatgataat gagggggtgg    60
agtttgtgac gtggcgcggg gcgtgggaac ggggcgggtg acgtagtagt gtggcggaag   120
tgtgatgttg caagtgtggc ggaacacatg taagcgacgg atgtggcaaa agtgacgttt   180
ttggtgtgcg ccggtgtaca caggaagtga caattttcgc gcggttttag gcggatgttg   240
tagtaaattt gggcgtaacc gagtaagatt tggccatttt cgcgggaaaa ctgaataaga   300
ggaagtgaaa tctgaataat tttgtgttac tcatagcgcg taatatttgt ctagggccgc   360
ggcgatgtac gggccagata tacgcgttga cattgattat tgactagtta ttaatagtaa   420
tcaattacgg ggtcattagt tcatagccca tatatggagt tccgcgttac ataacttacg   480
gtaaatggcc cgcctggctg accgcccaac gacccccgcc cattgacgtc aataatgacg   540
tatgttccca tagtaacgcc aatagggact ttccattgac gtcaatgggt ggagtattta   600
cggtaaactg cccacttggc agtacatcaa gtgtatcata tgccaagtac gccccctatt   660
gacgtcaatg acggtaaatg gcccgcctgg cattatgccc agtacatgac cttatgggac   720
tttcctactt ggcagtacat ctacgtatta gtcatcgcta ttaccatgat gatgcggttt   780
tggcagtaca tcaatgggcg tggatagcgg tttgactcac ggggatttcc aagtctccac   840
cccattgacg tcaatgggag tttgttttga ctagtaaatc aacgggactt tccaaaatgt   900
cgtaacaact ccgccccatt gacgcaaatg ggcggtaggc gtgtacggtg gaggtctat    960 ataagcagag ctcgtttagt gaaccgtcag ataagcttcg cgcgggtacc actctcttcg  1020
catcgctgtc tgcgagggcc agctgttggg ctcgcggttg aggacaaact cttcgcggtc  1080 ttteccagtac tcttggatcg gaaacccgtc ggcctccgaa cggtactccg ccaccgaggg  1140
acctgagcga gtccgcatcg accggatcgg aaaacctctc gagtctagag gtaagtgtct  1200
tcctcctgtt tccttcccct gctattctgc tcaacctttcc tatcagaaac tgcagtatct  1260
```

```
gtattttgc  tagcacaagt  ttgtacaaaa  aagcaggctc  ttttttctc  ttcacaggct    1320 ccagtcgacc  accatggcct  tgacctttgc  tttactagtg  gccctcctgg  tgctcagctg    1380
caagagctcc  tgcagcgtgg  gctgtgatct  gcctcaaacc  cacagcctgg  gtagcaggag    1440
gaccttgatg  ctcctggcac  agatgaggag  aatctctctt  ttctcctgct  tgaaggacag    1500
acatgacttt  ggatttcccc  aggaggagtt  tggcaaccag  ttccaaaagg  ctgaaaccat    1560
ccctgtcctc  catgagatga  tccagcagat  cttcaatctc  ttcagcacaa  aggactcatc    1620
tgctgcttgg  gatgagaccc  tcctagacaa  attctacact  gaactctacc  agcagctgaa    1680
tgacctggaa  gcctgtgtga  tacagggggt  gggggtgaca  gagactcccc  tgatgaagga    1740
ggactccatt  ctggctgtga  ggaaatactt  ccaaagaatc  actctctatc  tgaaagagaa    1800
gaaatacagc  ccttgtgcct  gggaggttgt  cagagcagaa  atcatgagat  cttttctt     1860 gtcaacaaac  ttgcaagaaa  gtttaagaag  taaggaatga  attcctgcag  cccgggtcta    1920
gaggatccag  cggccgctgt  taatcaacct  ctggattaca  aaatttgtga  aagattgact    1980
ggtattctta  actatgttgc  tccttttacg  ctatgtggat  acgctgcttt  aatgcctttg    2040
tatcatgcta  ttgcttcccg  tatggctttc  attttctcct  ccttgtataa  atcctggttg    2100
ctgtctcttt  atgaggagtt  gtggcccgtt  gtcaggcaac  gtggcgtggt  gtgcactgtg    2160
tttgctgacg  caaccccac  tggttggggc  attgccacca  cctgtcagct  cctttccggg    2220
actttcgctt  tccccctccc  tattgccacg  gcggaactca  tcgccgcctg  ccttgcccgc    2280
tgctggacag  gggctcggct  gttgggcact  gacaattccg  tggtgttgtc  ggggaagctg    2340
acgtcctttc  catggctgct  cgcctgtgtt  gccacctgga  ttctgcgcgg  acgtccttc     2400 tgctacgtcc  cttcggccct  caatccagcg  gaccttcctt  cccgcggcct  gctgccggct    2460
ctgcggcctc  ttccgcgtct  tcgccttcgc  cctcagacga  gtcggatctc  cctttgggcc    2520
gcctccccgc  ctgtttctag  ttgatccgag  ctcggtacca  agcttaagtt  taaaccgctg    2580
atcagcctcg  actgtgcctt  ctagttgcca  gccatctgtt  gtttgcccct  ccccgtgcc     2640 ttccttgacc  ctggaaggtg  ccactcccac  tgtcctttcc  taataaaatg  aggaaattgc    2700
atcgcattgt  ctgagtaggt  gtcattctat  tctgggggt  ggggtggggc  aggacagcaa    2760
gggggaggat  tgggaagaca  atagcaggca  tgctggggat  gcggtgggct  ctatggcttc    2820
tgaggcggaa  agaaccatct  agtgggcaga  tcccccaggg  atgtaattac  gtccctcccc    2880
cgctaggggg  cagcaagatc  ccccaggga  gtaattacgt  ccctccccg   ctagggggca   2940 gcaagatccc  ccaggatgt  aattacgtcc  ctccccgct  aggggcagc  aagatccccc    3000 aggatgtaa  ttacgtccct  ccccgctag  ggggcagcag  gatcctcgaa  tgcatcgcgc    3060
tctagatacg  taggatccat  cgattaacta  taacggtcct  aaggtagcga  tttaaatgat    3120
cccatggccc  aaaacataaa  taaaaaccag  actctgttg  gattttgatc  aagcaagtgt    3180
cttgctgtct  ttatttaggg  gttttgcgcg  cgcggtaggc  ccgggaccag  cggtctcggt    3240
cgttgagggt  cctgtgtatt  ttttccagga  cgtggtaaag  gtgactctgg  atgttcagat    3300
acatgggcat  aagcccgtct  ctgggtgga  ggtagcacca  ctgcagagct  tcatgctgcg    3360
gggtggtgtt  gtagatgatc  cagtcgtagc  aggagcgctg  ggcgtggtgc  ctaaaaatgt    3420 cttttcagtag  caagctgatt  gccagggca  ggcccttggt  gtaagtgttt  acaaagcggt    3480
taagctggga  tgggtgcata  cgtggggata  tgagatgcat  cttggactgt  attttaggt     3540 tggctatgtt  cccagccata  tccctccggg  gattcatgtt  gtgcagaacc  accagcacag    3600
tgtatccggt  gcacttggga  aatttgtcat  gtagcttaga  aggaaatgcg  tggaagaact    3660
```

```
tggagacgcc cttgtgacct ccgagatttt ccatgcattc gtccataatg atggcaatgg   3720
gcccacgggc ggcggcctgg gcgaagatat ttctgggatc actaacgtca tagttgtgtt   3780
ccaggatgag atcgtcatag gccatttta caaagcgcgg gcggagggtg ccagactgcg    3840
gtataatggt tccatccggc ccaggggcgt agttaccctc acagatttgc atttcccacg   3900
ctttgagttc agatgggggg atcatgtcta cctgcgggc gatgaagaaa accgtttccg    3960
gggtaggga gatcagctgg gaagaaagca ggttcctgag cagctgcgac ttaccgcagc    4020
cggtgggccc gtaaatcaca cctattaccg gctgcaactg gtagttaaga gagctgcagc   4080
tgccgtcatc cctgagcagg ggggccactt cgttaagcat gtccctgact tgcatgtttt   4140
ccctgaccaa atgcgccaga aggcgctcgc cgcccagcga tagcagttct tgcaaggaag   4200
caaagttttt caacggtttg aggccgtccg ccgtaggcat gcttttgagc gtttgaccaa   4260
gcagttccag gcggtcccac agctcggtca cgtgctctac ggcatctcga tccagcatat   4320
ctcctcgttt cgcgggttgg ggcggctttc gctgtacggc agtagtcggt gctcgtccag   4380
acgggccagg gtcatgtctt ccacgggcg cagggtcctc gtcagcgtag tctgggtcac    4440
ggtgaagggg tgcgctccgg gctgcgcgct ggccagggtg cgcttgaggc tggtcctgct   4500
ggtgctgaag cgctgccggt cttcgccctg cgcgtcggcc aggtagcatt tgaccatggt   4560
gtcatagtcc agcccctccg cggcgtggcc cttggcgcgc agcttgccct ggaggaggc    4620
gccgcacgag gggcagtgca gacttttaag ggcgtagagc ttgggcgcga gaataccga    4680
ttccggggag taggcatccg cgccgcaggc cccgcagacg gtctcgcatt ccacgagcca   4740
ggtgagctct ggccgttcgg ggtcaaaaac caggtttccc ccatgctttt tgatgcgttt   4800
cttacctctg gtttccatga gccggtgtcc acgtcggtg acgaaaaggc tgtccgtgtc    4860
cccgtataca gacttgagag gcctgtcctc gagcggtgtt ccgcggtcct cctcgtatag   4920
aaactcggac cactctgaga cgaaggctcg cgtccaggcc agcacgaagg aggctaagtg   4980
ggaggggtag cggtcgttgt ccactagggg gtccactcgc tccagggtgt gaagacacat   5040
gtcgccctct tcggcatcaa ggaaggtgat tggtttatag gtgtaggcca cgtgaccggg   5100
tgttcctgaa ggggggctat aaaaggggt gggggcgcgt tcgtcctcac tctcttccgc    5160
atcgctgtct gcgagggcca gctgttgggg tgagtactcc ctctcaaaag cgggcatgac   5220
ttctgcgcta agattgtcag tttccaaaaa cgaggaggat ttgatattca cctggcccgc   5280
ggtgatgcct ttgagggtgg ccgcgtccat ctggtcagaa aagacaatct ttttgttgtc   5340
aagcttggtg gcaaacgacc cgtagagggc gttggacagc aacttggcga tggagcgcag   5400
ggttggtttt ttgtcgcgat cggcgcgctc cttggccgcg atgtttagct gcacgtattc   5460
gcgcgcaacg caccgccatt cgggaaagac ggtggtgcgc tcgtcgggca ccaggtgcac   5520
gcgccaaccg cggttgtgca gggtgacaag gtcaacgctg gtggctacct ctccgcgtag   5580
gcgctcgttg gtccagcaga ggcggccgcc cttgcgcgag cagaatggcg gtaggggtc    5640
tagctgcgtc tcgtccgggg ggtctgcgtc cacggtaaag accccgggca gcaggcgcgc   5700
gtcgaagtag tctatcttgc atccttgcaa gtctagcgcc tgctgccatg cgcgggcggc   5760
aagcgcgcgc tcgtatgggt tgagtggggg accccatggc atgggtggg tgagcgcgga    5820
ggcgtacatg ccgcaaatgt cgtaaacgta gaggggctct ctgagtattc caagatatgt   5880
agggtagcat cttccaccgc ggatgctggc gcgcacgtaa tcgtatagtt cgtgcgaggg   5940
agcgaggagg tcgggaccga ggttgctacg ggcgggctgc tctgctcgga agactatctg   6000
cctgaagatg gcatgtgagt tggatgatat ggttggacgc tggaagacgt tgaagctggc   6060
```

```
gtctgtgaga cctaccgcgt cacgcacgaa ggaggcgtag gagtcgcgca gcttgttgac    6120
cagctcggcg gtgacctgca cgtctagggc gcagtagtcc agggtttcct tgatgatgtc    6180
atacttatcc tgtcccttt ttttccacag ctcgcggttg aggacaaact cttcgcggtc     6240
tttccagtac tcttggatcg gaaacccgtc ggcctccgaa cggtaagagc ctagcatgta    6300
gaactggttg acggcctggt aggcgcagca tcccttttct acgggtagcg cgtatgcctg    6360
cgcggccttc cggcatgacc agcatgaagg gcacgagctg cttcccaaag gcccccatcc    6420
aagtataggt ctctacatcg taggtgacaa agagacgctc ggtgcgagga tgcgagccga    6480
tcgggaagaa ctggatctcc cgccaccaat tggaggagtg gctattgatg tggtgaaagt    6540
agaagtccct gcgacgggcc gaacactcgt gctggctttt gtaaaaacgt gcgcagtact    6600
ggcagcggtg cacgggctgt acatcctgca cgaggttgac ctgacgaccg cgcacaagga    6660
agcagagtgg gaatttgagc ccctcgcctg gcgggtttgg ctggtggtct tctacttcgg    6720
ctgcttgtcc ttgaccgtct ggctgctcga ggggagttac ggtggatcgg accaccacgc    6780
cgcgcgagcc caaagtccag atgtccgcgc gcggcggtcg gagcttgatg acaacatcgc    6840
gcagatggga gctgtccatg gtctggagct cccgcggcgt caggtcaggc gggagctcct    6900
gcaggtttac ctcgcataga cgggtcaggg cgcgggctag atccaggtga tacctaattt    6960
ccaggggctg gttggtggcg gcgtcgatgg cttgcaagag gccgcatccc cgcggcgcga    7020
ctacggtacc gcgcggcggg cggtgggccg cggggggtgtc cttggatgat gcatctaaaa   7080
gcggtgacgc gggcgagccc ccggaggtag gggggggctcc ggacccgccg ggagaggggg   7140
caggggcacg tcggcgccgc gcgcgggcag gagctggtgc tgcgcgcgta ggttgctggc    7200
gaacgcgacg acgcggcggt tgatctcctg aatctggcgc ctctgcgtga agacgacggg    7260
cccggtgagc ttgagcctga aagagagttc gacagaatca atttcggtgt cgttgacggc    7320
ggcctggcgc aaaatctcct gcacgtctcc tgagttgtct tgataggcga tctcggccat    7380
gaactgctcg atctcttcct cctggagatc tccgcgtccg gctcgctcca cggtggcggc    7440
gaggtcgttg gaaatgcggg ccatgagctg cgagaaggcg ttgaggcctc cctcgttcca    7500
gacgcggctg tagaccacgc cccctcggc atcgcgggcg cgcatgacca cctgcgcgag    7560
attgagctcc acgtgccggg cgaagacggc gtagtttcgc aggcgctgaa agaggtagtt    7620
gagggtggtg gcggtgtgtt ctgccacgaa gaagtacata acccagcgtc gcaacgtgga    7680
ttcgttgata tccccaagg cctcaaggcg ctccatggcc tcgtagaagt ccacggcgaa     7740
gttgaaaaac tgggagttgc gcgccgacac ggttaactcc tcctcagaa gacggatgag     7800 ctcggcgaca gtgtcgcgca cctcgcgctc aaaggctaca ggggcctctt cttcttcttc    7860
aatctcctct tccataaggg cctccccttc ttcttcttct ggcggcggtg ggggagggg     7920 gacacggcgg cgacgacggc gcaccggag gcgtcgaca aagcgctcga tcatctcccc      7980
gcggcgacgg cgcatggtct cggtgacggc gcggccgttc tcgcggggc gcagttggaa     8040 gacgccgccc gtcatgtccc ggttatgggt tggcggggg ctgccatgcg gcagggatac     8100
ggcgctaacg atgcatctca acaattgttg tgtaggtact ccgccgccga gggacctgag    8160
cgagtccgca tcgaccggat cggaaaacct ctcgagaaag gcgtctaacc agtcacagtc    8220
gcaaggtagg ctgagcaccg tggcgggcgg cagcgggcgg cggtcgggt tgtttctggc     8280 ggaggtgctg ctgatgatgt aattaaagta ggcggtcttg agacggcgga tggtcgacag    8340
aagcaccatg tccttgggtc cggcctgctg aatgcgcagg cggtcggcca tgccccaggc    8400
ttcgttttga catcggcgca ggtctttgta gtagtcttgc atgagccttt ctaccggcac    8460
```

```
ttcttcttct ccttcctctt gtcctgcatc tcttgcatct atcgctgcgg cggcggcgga   8520
gtttggccgt aggtggcgcc ctcttcctcc catgcgtgtg accccgaagc ccctcatcgg   8580
ctgaagcagg gctaggtcgg cgacaacgcg ctcggctaat atggcctgct gcacctgcgt   8640
gagggtagac tggaagtcat ccatgtccac aaagcggtgg tatgcgcccg tgttgatggt   8700
gtaagtgcag ttggccataa cggaccagtt aacggtctgg tgacccggct gcagagctc    8760
ggtgtacctg agacgcgagt aagccctcga gtcaaatacg tagtcgttgc aagtccgcac   8820
caggtactgg tatcccacca aaaagtgcgg cggcggctgg cggtagaggg gccagcgtag   8880
ggtggccggg gctccggggg cgagatcttc aacataagg cgatgatatc cgtagatgta    8940
cctggacatc caggtgatgc cggcggcggt ggtggaggcg cgcggaaagt cgcggacgcg   9000
gttccagatg ttgcgcagcg gcaaaaagtg ctccatggtc gggacgctct ggccggtcag   9060
gcgcgcgcaa tcgttgacgc tctagaccgt gcaaaaggag agcctgtaag cgggcactct   9120
tccgtggtct ggtggataaa ttcgcaaggg tatcatggcg gacgacaggg gttcgagccc   9180
cgtatccggc cgtccgccgt gatccatgcg gttaccgccc gcgtgtcgaa cccaggtgtg   9240
cgacgtcaga caacgcggga gtgctccttt tggcttcctt ccaggcgcgg cggctgctgc   9300
gctagctttt ttggccactg gccgcgcgca gcgtaagcgg ttaggctgga aagcgaaagc   9360
attaagtggc tcgctccctg tagccggagg gttattttcc aagggttgag tcgcgggacc   9420
cccggttcga gtctcggacc ggccggactg cggcgaacgg gggtttgcct ccccgtcatg   9480
caagaccccg cttgcaaatt cctccggaaa cagggacgag cccctttttt gcttttccca   9540
gatgcatccg gtgctgcggc agatgcgccc ccctcctcag cagcggcaag agcaagagca   9600
gcggcagaca tgcagggcac cctcccctcc tcctaccgcg tcaggagggg cgacatccgc   9660
ggttgacgcg gcagcagatg gtgattacga accccgcgg cgccgggccc ggcactacct    9720
ggacttggag gagggcgagg gcctggcgcg gctaggagcg ccctctcctg agcggtaccc   9780
aagggtgcag ctgaagcgtg atacgcgtga ggcgtacgtg ccgcggcaga acctgtttcg   9840
cgaccgcgag ggagaggagc ccgaggagat gcgggatcga aagttccacg cagggcgcga   9900
gctgcggcat ggcctgaatc gcgagcggtt gctgcgcgag gaggactttg agcccgacgc   9960
gcgaaccggg attagtcccg cgcgcgcaca cgtggcggcc gccgacctgg taaccgcata  10020
cgagcagacg gtgaaccagg agattaactt tcaaaaaagc tttaacaacc acgtgcgtac  10080
gcttgtggcg cgcgaggagg tggctatagg actgatgcat ctgtgggact ttgtaagcgc  10140
gctggagcaa aacccaaata gcaagccgct catggcgcag ctgttcctta tagtgcagca  10200
cagcagggac aacgaggcat tcagggatgc gctgctaaac atagtagagc ccagggccg   10260
ctggctgctc gatttgataa acatcctgca gagcatagtg gtgcaggagc gcagcttgag  10320
cctggctgac aaggtggccg ccatcaacta ttccatgctt agcctgggca gttttacgc   10380
ccgcaagata taccatacc cttacgttcc catagacaag gaggtaaaga tcgagggtt    10440
ctacatgcgc atggcgctga aggtgcttac cttgagcgac gacctgggcg tttatcgcaa  10500
cgagcgcatc cacaaggccg tgagcgtgag ccggcggcgc gagctcagcg accgcgagct  10560
gatgcacagc ctgcaaaggg ccctggctgg cacgggcagc ggcgatagag aggccgagtc  10620
ctactttgac gcgggcgctg acctgcgctg gccccaagc cgacgcgccc tggaggcagc   10680
tggggccgga cctgggctgg cggtggcacc cgcgcgcgct ggcaacgtcg cggcgtgga   10740
ggaatatgac gaggacgatg agtacagacc agaggacggc gagtactaag cggtgatgtt  10800
tctgatcaga tgatgcaaga cgcaacggac ccggcggtgc gggcggcgct gcagagccag  10860
```

```
ccgtccggcc ttaactccac ggacgactgg cgccaggtca tggaccgcat catgtcgctg    10920
actgcgcgca atcctgacgc gttccggcag cagccgcagg ccaaccggct ctccgcaatt    10980
ctggaagcgg tggtcccggc gcgcgcaaac cccacgcacg agaaggtgct ggcgatcgta    11040
aacgcgctgg ccgaaaacag ggccatccgg cccgacgagg ccggcctggt ctacgacgcg    11100
ctgcttcagc gcgtggctcg ttacaacagc ggcaacgtgc agaccaacct ggaccggctg    11160
gtgggggatg tgcgcgaggc cgtggcgcag cgtgagcgcg cgcagcagca gggcaacctg    11220
ggctccatgg ttgcactaaa cgccttcctg agtacacagc ccgccaacgt gccgcgggga    11280
caggaggact acaccaactt tgtgagcgca ctgcggctaa tggtgactga gacaccgcaa    11340
agtgaggtgt accagtctgg gccagactat ttttccaga ccagtagaca aggcctgcag     11400
accgtaaacc tgagccaggc tttcaaaaac ttgcaggggc tgtgggggt gcgggctccc     11460 acaggcgacc gcgcgaccgt gtctagcttg ctgacgccca actcgcgcct gttgctgctg    11520
ctaatagcgc ccttcacgga cagtggcagc gtgtcccggg acacatacct aggtcacttg    11580
ctgacactgt accgcgaggc cataggtcag gcgcatgtgg acgagcatac tttccaggag    11640
attacaagtg tcagccgcgc gctggggcag gaggacacgg gcagcctgga ggcaacccta    11700
aactacctgc tgaccaaccg gcggcagaag atcccctcgt tgcacagttt aaacagcgag    11760
gaggagcgca ttttgcgcta cgtgcagcag agcgtgagcc ttaacctgat gcgcgacggg    11820
gtaacgccca gcgtggcgct ggacatgacc gcgcgcaaca tggaaccggg catgtatgcc    11880
tcaaaccggc cgtttatcaa ccgcctaatg gactacttgc atcgcgcggc cgccgtgaac    11940
cccgagtatt tcaccaatgc catcttgaac ccgcactggc taccgccccc tggtttctac    12000
accgggggat tcgaggtgcc cgagggtaac gatggattcc tctgggacga catagacgac    12060
agcgtgtttt ccccgcaacc gcagaccctg ctagagttgc aacagcgcga gcaggcagag    12120
gcggcgctgc gaaaggaaag cttccgcagg ccaagcagct tgtccgatct aggcgctgcg    12180
gccccgcggt cagatgctag tagcccattt ccaagcttga taggtctct taccagcact     12240 cgcaccaccc gcccgcgcct gctgggcgag gaggagtacc taaacaactc gctgctgcag    12300
ccgcagcgcg aaaaaaacct gcctccggca tttcccaaca acgggataga gagcctagtg    12360
gacaagatga gtagatggaa gacgtacgcg caggagcaca gggacgtgcc aggcccgcgc    12420
ccgcccaccc gtcgtcaaag gcacgaccgt cagcggggtc tggtgtggga ggacgatgac    12480
tcggcagacg acagcagcgt cctggatttg gagggagtg gcaacccgtt tgcgcacctt    12540
cgccccaggc tggggagaat gttttaaaaa aaaaaagca tgatgcaaaa taaaaaactc    12600
accaaggcca tggcaccgag cgttggtttt cttgtattcc ccttagtatg cggcgcgcgg    12660
cgatgtatga ggaaggtcct cctccctcct acgagagtgt ggtgagcgcg cgccagtgg    12720 cggcggcgct gggttctccc ttcgatgctc ccctggaccc gccgtttgtg cctccgcggt    12780
acctgcggcc taccggggg agaaacagca tccgttactc tgagttggca cccctattcg    12840
acaccacccg tgtgtacctg gtggacaaca agtcaacgga tgtggcatcc ctgaactacc    12900
agaacgacca cagcaacttt ctgaccacgg tcattcaaaa caatgactac agcccggggg    12960
aggcaagcac acagaccatc aatcttgacg accggtcgca ctggggcggc gacctgaaaa    13020
ccatcctgca taccaacatg ccaaatgtga acgagttcat gtttaccaat aagtttaagg    13080
cgcgggtgat ggtgtcgcgc ttgcctacta aggacaatca ggtggagctg aaatacgagt    13140
gggtggagtt cacgctgccc gagggcaact actccgagac catgaccata gaccttatga    13200
acaacgcgat cgtggagcac tacttgaaag tgggcagaca gaacggggtt ctggaaagcg    13260
```

```
acatcggggt aaagtttgac acccgcaact tcagactggg gtttgacccc gtcactggtc   13320
ttgtcatgcc tggggtatat acaaacgaag ccttccatcc agacatcatt ttgctgccag   13380
gatgcggggt ggacttcacc cacagccgcc tgagcaactt gttgggcatc cgcaagcggc   13440
aacccttcca ggagggcttt aggatcacct acgatgatct ggagggtggt aacattcccg   13500
cactgttgga tgtggacgcc taccaggcga gcttgaaaga tgacaccgaa cagggcgggg   13560
gtggcgcagg cggcagcaac agcagtggca gcggcgcgga agagaactcc aacgcggcag   13620
ccgcggcaat gcagccggtg gaggacatga acgatcatgc cattcgcggc gacaccttctg  13680 ccacacgggc tgaggagaag cgcgctgagg ccgaagcagc ggccgaagct gccgccccg    13740 ctgcgcaacc cgaggtcgag aagcctcaga gaaaccggt gatcaaaccc ctgacagagg    13800
acagcaagaa acgcagttac aacctaataa gcaatgacag caccttcacc cagtaccgca   13860
gctggtacct tgcatacaac tacggcgacc ctcagaccgg aatccgctca tggaccctgc   13920
tttgcactcc tgacgtaacc tgcggctcgg agcaggtcta ctggtcgttg ccagacatga   13980
tgcaagaccc cgtgaccttc cgctccacgc gccagatcag caactttccg gtggtgggcg   14040
ccgagctgtt gcccgtgcac tccaagagct tctacaacga ccaggccgtc tactcccaac   14100
tcatccgcca gtttacctct ctgacccacg tgttcaatcg ctttcccgag aaccagattt   14160
tggcgcgccc gccagccccc accatcacca ccgtcagtga aaacgttcct gctctcacag   14220
atcacgggac gctaccgctg cgcaacagca tcggaggagt ccagcgagtg accattactg   14280
acgccagacg ccgcacctgc ccctacgttt acaaggccct gggcatagtc tcgccgcgcg   14340
tcctatcgag ccgcactttt tgagcaagca tgtccatcct tatatcgccc agcaataaca   14400
caggctgggg cctgcgcttc ccaagcaaga tgtttggcgg ggccaagaag cgctccgacc   14460
aacacccagt gcgcgtgcgc gggcactacc gcgcgccctg gggcgcgcac aaacgcggcc   14520
gcactgggcg caccaccgtc gatgacgcca tcgacgcggt ggtggaggag gcgcgcaact   14580
acacgcccac gccgccacca gtgtccacag tggacgcggc cattcagacc gtggtgcgcg   14640
gagcccggcg ctatgctaaa atgaagagac ggcggaggcg cgtagcacgt cgccaccgcc   14700
gccgacccgg cactgccgcc caacgcgcgg cggcggccct gcttaaccgc gcacgtcgca   14760
ccggccgacg ggcggccatg cgggccgctc gaaggctggc cgcgggtatt gtcactgtgc   14820
cccccaggtc caggcgacga gcggccgccg cagcagccgc ggccattagt gctatgactc   14880
agggtcgcag gggcaacgtg tattgggtgc gcgactcggt tagcggcctg cgcgtgcccg   14940
tgcgcacccg ccccccgcgc aactagattg caagaaaaaa ctacttagac tcgtactgtt   15000
gtatgtatcc agcggcggcg gcgcgcaacg aagctatgtc caagcgcaaa atcaaagaag   15060
agatgctcca ggtcatcgcg ccggagatct atggccccc gaagaaggaa gagcaggatt    15120
acaagccccg aaagctaaag cgggtcaaaa agaaaaagaa agatgatgat gatgaacttg   15180
acgacgaggt ggaactgctg cacgctaccg cgcccaggcg acgggtacag tggaaaggtc   15240
gacgcgtaaa acgtgttttg cgaccccgca ccaccgtagt ctttacgccc ggtgagcgct   15300 ccaccccgcac ctacaagcgc gtgtatgatg aggtgtacgg cgacgaggac ctgcttgagc   15360
aggccaacga gcgcctcggg gagtttgcct acggaaagcg gcataaggac atgctggcgt   15420
tgccgctgga cgagggcaac ccaacaccta gcctaaagcc cgtaacactg cagcaggtgc   15480
tgcccgcgct tgcaccgtcc gaagaaaagc gcggcctaaa gcgcgagtct ggtgacttgg   15540
cacccaccgt gcagctgatg gtaccaagc gccagcgact ggaagatgtc ttggaaaaaa   15600
tgaccgtgga acctgggctg gagcccgagg tccgcgtgcg gccaatcaag caggtggcgc   15660
```

```
cgggactggg cgtgcagacc gtggacgttc agatacccac taccagtagc accagtattg    15720
ccaccgccac agagggcatg gagacacaaa cgtccccggt tgcctcagcg gtggcggatg    15780
ccgcggtgca ggcggtcgct gcggccgcgt ccaagacctc tacggagtg caaacggacc     15840
cgtggatgtt tcgcgtttca gcccccggc gcccgcgcgg ttcgaggaag tacggcgccg     15900
ccagcgcgct actgcccgaa tatgccctac atccttccat tgcgcctacc cccggctatc    15960
gtggctacac ctaccgcccc agaagacgag caactacccg acgccgaacc accactggaa    16020
cccgccgccg ccgtcgccgt cgccagcccg tgctggcccc gatttccgtg cgcagggtgg    16080
ctcgcgaagg aggcaggacc ctggtgctgc aacagcgcg ctaccacccc agcatcgttt     16140
aaaagccggt ctttgtggtt cttgcagata tggccctcac ctgccgcctc cgtttcccgg    16200
tgccgggatt ccgaggaaga atgcaccgta ggaggggcat ggcggccac ggcctgacgg     16260
gcggcatgcg tcgtgcgcac caccggcggc ggcgcgcgtc gcaccgtcgc atgcgcggcg    16320
gtatcctgcc cctccttatt ccactgatcg ccgcggcgat tggcgccgtg cccggaattg    16380
catccgtggc cttgcaggcg cagagacact gattaaaaac aagttgcatg tggaaaaatc    16440
aaaataaaaa gtctggactc tcacgctcgc ttggtcctgt aactattttg tagaatggaa    16500
gacatcaact ttgcgtctct ggccccgcga cacggctcgc gcccgttcat gggaaactgg    16560
caagatatcg gcaccagcaa tatgagcggt ggcgccttca gctggggctc gctgtggagc    16620
ggcattaaaa atttcggttc caccgttaag aactatggca gcaaggcctg aacagcagc    16680
acaggccaga tgctgaggga taagttgaaa gagcaaaatt ccaacaaaa ggtggtagat     16740
ggcctggcct ctggcattag cggggtggtg gacctggcca accaggcagt gcaaaataag    16800
attaacagta agcttgatcc ccgccctccc gtagaggagc ctccaccggc cgtgagaca     16860
gtgtctccag aggggcgtgg cgaaaagcgt ccgcgccccg acagggaaga aactctggtg    16920
acgcaaatag acgagcctcc ctcgtacgag gaggcactaa agcaaggcct gcccaccacc    16980
cgtcccatcg cgcccatggc taccggagtg ctgggccagc acacacccgt aacgctggac    17040
ctgcctcccc ccgccgacac ccagcagaaa cctgtgctgc caggcccgac cgccgttgtt    17100
gtaacccgtc ctagccgcgc gtccctgcgc gcgcgccgcca gcggtccgcg atcgttgcgg    17160
cccgtagcca gtggcaactg gcaaagcaca ctgaacagca tcgtgggtct ggggggtgcaa   17220
tccctgaagc gccgacgatg cttctgaata gctaacgtgt cgtatgtgtg tcatgtatgc    17280
gtccatgtcg ccgccagagg agctgctgag ccgccgcgcg cccgctttcc aagatggcta    17340
ccccttcgat gatgccgcag tggtcttaca tgcacatctc gggccaggac gcctcggagt    17400
acctgagccc cgggctggtg cagtttgccc gcgccaccga gacgtacttc agcctgaata    17460
acaagtttag aaaccccacg gtggcgccta cgcacgacgt gaccacagac cggtcccagc    17520
gtttgacgct gcggttcatc cctgtggacc gtgaggatac tgcgtactcg tacaaggcgc    17580
ggttcacccct agctgtgggt gataaccgtg tgctggacat ggcttccacg tactttgaca    17640
tccgcgcgt gctggacagg ggccctactt ttaagcccta ctctggcact gcctacaacg    17700
ccctggctcc caagggtgcc ccaaatcctt gcgaatggga tgaagctgct actgctcttg    17760
aaataaacct agaagaagag gacgatgaca acgaagacga agtagacgag caagctgagc    17820
agcaaaaaac tcacgtattt gggcaggcgc ttattctgg tataaatatt acaaggagg     17880
gtattcaaat aggtgtcgaa ggtcaaacac ctaaatatgc cgataaaaca tttcaacctg    17940
aacctcaaat aggagaatct cagtggtacg aaactgaaat taatcatgca gctgggagag    18000
tccttaaaaa gactaccccca atgaaaccat gttacggttc atatgcaaaa cccacaaatg    18060
```

```
aaaatggagg gcaaggcatt cttgtaaagc aacaaaatgg aaagctagaa agtcaagtgg    18120
aaatgcaatt tttctcaact actgaggcga ccgcaggcaa tggtgataac ttgactccta    18180
aagtggtatt gtacagtgaa gatgtagata tagaaacccc agacactcat atttcttaca    18240
tgcccactat taaggaaggt aactcacgag aactaatggg ccaacaatct atgcccaaca    18300
ggcctaatta cattgctttt agggacaatt ttattggtct aatgtattac aacagcacgg    18360
gtaatatggg tgttctggcg ggccaagcat cgcagttgaa tgctgttgta gatttgcaag    18420
acagaaacac agagctttca taccagcttt tgcttgattc cattggtgat agaaccaggt    18480
acttttctat gtggaatcag gctgttgaca gctatgatcc agatgttaga attattgaaa    18540
atcatggaac tgaagatgaa cttccaaatt actgctttcc actgggaggt gtgattaata    18600
cagagactct taccaaggta aaacctaaaa caggtcagga aaatggatgg gaaaaagatg    18660
ctacagaatt ttcagataaa aatgaaataa gagttggaaa taattttgcc atggaaatca    18720
atctaaatgc caacctgtgg agaaatttcc tgtactccaa catagcgctg tatttgcccg    18780
acaagctaaa gtacagtcct tccaacgtaa aaatttctga taacccaaac acctacgact    18840
acatgaacaa gcgagtggtg gctcccgggt tagtggactg ctacattaac cttggagcac    18900
gctggtccct tgactatatg gacaacgtca acccatttaa ccaccaccgc aatgctggcc    18960
tgcgctaccg ctcaatgttg ctgggcaatg gtcgctatgt gcccttccac atccaggtgc    19020
ctcagaagtt cttttgccatt aaaaaacctcc ttctcctgcc gggctcatac acctacgagt    19080
```

```
actcaagcag gtttaccagt ttgagtacga gtcactcctg cgccgtagcg ccattgcttc    20520
ttcccccgac cgctgtataa cgctggaaaa gtccacccaa agcgtacagg ggcccaactc    20580
ggccgcctgt ggactattct gctgcatgtt tctccacgcc tttgccaact ggccccaaac    20640
tcccatggat cacaacccca ccatgaacct tattaccggg gtacccaact ccatgctcaa    20700
cagtccccag gtacagccca ccctgcgtcg caaccaggaa cagctctaca gcttcctgga    20760
gcgccactcg ccctacttcc gcagccacag tgcgcagatt aggagcgcca cttcttttg    20820 tcacttgaaa aacatgtaaa aataatgtac tagagacact ttcaataaag gcaaatgctt    20880
ttatttgtac actctcgggt gattatttac ccccacccett gccgtctgcg ccgtttaaaa    20940
atcaaagggg ttctgccgcg catcgctatg cgccactggc agggacacgt tgcgatactg    21000
gtgtttagtg ctccacttaa actcaggcac aaccatccgc ggcagctcgg tgaagttttc    21060
actccacagg ctgcgcacca tcaccaacgc gtttagcagg tcgggcgccg atatcttgaa    21120
gtcgcagttg gggcctccgc cctgcgcgcg cgagttgcga tacacagggt tgcagcactg    21180
gaacactatc agcgccgggt ggtgcacgct ggccagcacg ctcttgtcgg agatcagatc    21240
cgcgtccagg tcctccgcgt tgctcagggc gaacggagtc aactttggta gctgccttcc    21300 caaaagggc gcgtgcccag gctttgagtt gcactcgcac cgtagtggca tcaaaaggtg    21360
accgtgcccg gtctgggcgt taggatacag cgcctgcata aaagccttga tctgcttaaa    21420
agccacctga gcctttgcgc cttcagagaa gaacatgccg caagacttgc cggaaaactg    21480
attggccgga caggccgcgt cgtgcacgca gcaccttgcg tcggtgttgg agatctgcac    21540
cacatttcgg ccccaccggt tcttcacgat cttggccttg ctagactgct ccttcagcgc    21600
gcgctgcccg ttttcgctcg tcacatccat ttcaatcacg tgctccttat ttatcataat    21660
gcttccgtgt agacacttaa gctcgccttc gatctcagcg cagcggtgca gccacaacgc    21720
gcagcccgtg ggctcgtgat gcttgtaggt cacctctgca aacgactgca ggtacgcctg    21780
caggaatcgc cccatcatcg tcacaaaggt cttgttgctg gtgaaggtca gctgcaaccc    21840
gcggtgctcc tcgttcagcc aggtcttgca tacggccgcc agagcttcca cttggtcagg    21900
cagtagtttg aagttcgcct ttagatcgtt atccacgtgg tacttgtcca tcagcgcgcg    21960
cgcagcctcc atgcccttct cccacgcaga cacgatcggc acactcagcg ggttcatcac    22020
cgtaatttca ctttccgctt cgctgggctc ttcctcttcc tcttgcgtcc gcataccacg    22080
cgccactggg tcgtcttcat tcagccgccg cactgtgcgc ttacctcctt tgccatgctt    22140
gattagcacc ggtgggttgc tgaaacccac catttgtagc gccacatctt ctctttcttc    22200
ctcgctgtcc acgattacct ctggtgatgg cgggcgctcg ggcttgggag aagggcgctt    22260 cttttttcttc ttgggcgcaa tggccaaatc cgccgccgag gtcgatggcc gcgggctggg    22320
tgtgcgcggc accagcgcgt cttgtgatga gtcttcctcg tcctcggact cgatacgccg    22380
cctcatccgc ttttttgggg gcgcccgggg aggcggcggc gacggggacg gggacgacac    22440
gtcctccatg gttggggggac gtcgcgccgc accgcgtccg cgctcggggg tggtttcgcg    22500
ctgctcctct tcccgactgg ccatttcctt ctcctatagg cagaaaaga tcatggagtc    22560 agtcgagaag aaggacagcc taaccgcccc ctctgagttc gccaccaccg cctccaccga    22620
tgccgccaac gcgcctacca ccttcccgt cgaggcaccc ccgcttgagg aggaggaagt    22680
gattatcgag caggacccag gttttgtaag cgaagacgac gaggaccgct cagtaccaac    22740
agaggataaa aagcaagacc aggacaacgc agaggcaaac gaggaacaag tcgggcgggg    22800
ggacgaaagg catggcgact acctagatgt gggagacgac gtgctgttga agcatctgca    22860
```

```
gcgccagtgc gccattatct gcgacgcgtt gcaagagcgc agcgatgtgc ccctcgccat    22920
agcggatgtc agccttgcct acgaacgcca cctattctca ccgcgcgtac cccccaaacg    22980
ccaagaaaac ggcacatgcg agcccaaccc gcgcctcaac ttctaccccg tatttgccgt    23040
gccagaggtg cttgccacct atcacatctt tttccaaaac tgcaagatac ccctatcctg    23100
ccgtgccaac cgcagccgag cggacaagca gctggccttg cggcagggcg ctgtcatacc    23160
tgatatcgcc tcgctcaacg aagtgccaaa aatctttgag ggtcttggac gcgacgagaa    23220
gcgcgcggca aacgctctgc aacaggaaaa cagcgaaaat gaaagtcact ctggagtgtt    23280
ggtggaactc gagggtgaca acgcgcgcct agccgtacta aaacgcagca tcgaggtcac    23340
ccactttgcc tacccggcac ttaacctacc ccccaaggtc atgagcacag tcatgagtga    23400
gctgatcgtg cgccgtgcgc agcccctgga gagggatgca aatttgcaag aacaaacaga    23460
ggagggccta cccgcagttg gcgacgagca gctagcgcgc tggcttcaaa cgcgcgagcc    23520
tgccgacttg gaggagcgac gcaaactaat gatggccgca gtgctcgtta ccgtggagct    23580
tgagtgcatg cagcggttct ttgctgaccc ggagatgcag cgcaagctag aggaaacatt    23640
gcactacacc tttcgacagg gctacgtacg ccaggcctgc aagatctcca acgtggagct    23700
ctgcaacctg gtctcctacc ttggaatttt gcacgaaaac cgccttgggc aaaacgtgct    23760
tcattccacg ctcaagggcg aggcgcgccg cgactacgtc cgcgactgcg tttacttatt    23820
tctatgctac acctggcaga cggccatggg cgtttggcag cagtgcttgg aggagtgcaa    23880
cctcaaggag ctgcagaaac tgctaaagca aaacttgaag gacctatgga cggccttcaa    23940
cgagcgctcc gtggccgcgc acctggcgga catcattttc cccgaacgcc tgcttaaaac    24000
cctgcaacag ggtctgccag acttcaccag tcaaagcatg ttgcagaact ttaggaactt    24060
tatcctagag cgctcaggaa tcttgcccgc cacctgctgt gcacttccta gcgactttgt    24120
gcccattaag taccgcgaat gccctccgcc gctttgggc cactgctacc ttctgcagct    24180
agccaactac cttgcctacc actctgacat aatggaagac gtgagcggtg acggtctact    24240
ggagtgtcac tgtcgctgca acctatgcac cccgcaccgc tccctggttt gcaattcgca    24300
gctgcttaac gaaagtcaaa ttatcggtac ctttgagctg cagggtccct cgcctgacga    24360
aaagtccgcg gctccggggt tgaaactcac tccggggctg tggacgtcgg cttaccttcg    24420
caaatttgta cctgaggact accacgccca cgagattagg ttctacgaag accaatcccg    24480
cccgcctaat gcggagctta ccgcctgcgt cattacccag ggccacattc ttggccaatt    24540
gcaagccatc aacaaagccc gccaagagtt tctgctacga aagggacggg gggtttactt    24600 ggaccccag tccggcgagg agctcaaccc aatcccccg ccgccgcagc cctatcagca    24660
gcagccgcgg gcccttgctt cccaggatgg cacccaaaaa gaagctgcag ctgccgccgc    24720
cacccacgga cgaggaggaa tactgggaca gtcaggcaga ggaggttttg gacgaggagg    24780
aggaggacat gatggaagac tgggagagcc tagacgagga agcttccgag gtcgaagagg    24840
tgtcagacga acaccgtca ccctcggtcg cattcccctc gccggcgccc cagaaatcgg    24900
caaccggttc cagcatggct acaacctccg ctcctcaggc gccgccggca ctgcccgttc    24960
gccgacccaa ccgtagatgg gacaccactg gaaccagggc cggtaagtcc aagcagccgc    25020
cgccgttagc ccaagagcaa caacagcgcc aaggctaccg ctcatggcgc gggcacaaga    25080
acgccatagt tgcttgcttg caagactgtg ggggcaacat ctccttcgcc cgccgctttc    25140
ttctctacca tcacgcgtg gccttcccc gtaacatcct gcattactac cgtcatctct    25200
acagcccata ctgcaccggc ggcagcggca gcaacagcag cggccacaca gaagcaaagg    25260
```

```
cgaccggata gcaagactct gacaaagccc aagaaatcca cagcggcggc agcagcagga   25320
ggaggagcgc tgcgtctggc gcccaacgaa cccgtatcga cccgcgagct tagaaacagg   25380 attttttccca ctctgtatgc tatatttcaa cagagcaggg gccaagaaca agagctgaaa   25440
ataaaaaaca ggtctctgcg atccctcacc cgcagctgcc tgtatcacaa aagcgaagat   25500
cagcttcggc gcacgctgga agacgcggag gctctcttca gtaaatactg cgcgctgact   25560
cttaaggact agtttcgcgc cctttctcaa atttaagcgc gaaaactacg tcatctccag   25620
cggccacacc cggcgccagc acctgttgtc agcgccatta tgagcaagga aattcccacg   25680
ccctacatgt ggagttacca gccacaaatg ggacttgcgg ctggagctgc ccaagactac   25740
tcaacccgaa taaactacat gagcgcggga ccccacatga tatcccgggt caacggaata   25800
cgcgcccacc gaaaccgaat tctcctggaa caggcggcta ttaccaccac acctcgtaat   25860
aaccttaatc cccgtagttg gcccgctgcc ctggtgtacc aggaaagtcc cgctcccacc   25920
actgtggtac ttcccagaga cgcccaggcc gaagttcaga tgactaactc aggggcgcag   25980
cttgcgggcg gctttcgtca cagggtgcgg tcgcccgggc agggtataac tcacctgaca   26040
atcagagggc gaggtattca gctcaacgac gagtcggtga gctcctcgct tggtctccgt   26100
ccggacggga catttcagat cggcggcgcc ggccgctctt cattcacgcc tcgtcaggca   26160
atcctaactc tgcagacctc gtcctctgag ccgcgctctg gaggcattgg aactctgcaa   26220
tttattgagg agtttgtgcc atcggtctac tttaaccccct tctcgggacc tcccggccac   26280
tatccggatc aatttattcc taactttgac gcggtaaagg actcggcgga cggctacgac   26340
tgaatgttaa gtggagaggc agagcaactg cgcctgaaac acctggtcca ctgtcgccgc   26400
cacaagtgct tgcccgcga ctccggtgag ttttgctact ttgaattgcc cgaggatcat   26460
atcgagggcc cggcgcacgg cgtccggctt accgcccagg gagagcttgc ccgtagcctg   26520
attcgggagt ttacccagcg ccccctgcta gttgagcggg acaggggacc ctgtgttctc   26580
actgtgattt gcaactgtcc taaccctgga ttacatcaag atctttgttg ccatctctgt   26640
gctgagtata ataatacag aaattaaaat atactggggc tcctatcgcc atcctgtaaa   26700
cgccaccgtc ttcacccgcc caagcaaacc aaggcgaacc ttacctggta cttttaacat   26760 ctctcccctct gtgatttaca acagtttcaa cccagacgga gtgagtctac gagagaacct   26820
ctccgagctc agctactcca tcagaaaaaa caccaccctc cttacctgcc gggaacgtac   26880
gagtgcgtca ccggccgctg caccacacct accgcctgac cgtaaaccag acttttttccg   26940 gacagacctc aataactctg tttaccagaa caggaggtga gcttagaaaa cccttagggt   27000
attaggccaa aggcgcagct actgtggggt ttatgaacaa ttcaagcaac tctacgggct   27060
attctaattc aggtttctct agtagaaatg gacggaatta ttacagagca gcgcctgcta   27120
gaaagacgca gggcagcggc cgagcaacag cgcatgaatc aagagctcca agacatggtt   27180
aacttgcacc agtgcaaaag gggtatcttt tgtctggtaa agcaggccaa agtcacctac   27240
gacagtaata ccaccggaca ccgccttagc tacaagttgc caaccaagcg tcagaaattg   27300
gtggtcatgg tgggagaaaa gcccattacc ataactcagc actcggtaga aaccgaaggc   27360
tgcattcact caccttgtca aggacctgag gatctctgca cccttattaa gaccctgtgc   27420
ggtctcaaag atcttattcc ctttaactaa taaaaaaaaa taataagca tcacttactt   27480 aaaatcagtt agcaaatttc tgtccagttt attcagcagc acctccttgc cctcctccca   27540
gctctggtat tgcagcttcc tcctggctgc aaactttctc cacaatctaa atggaatgtc   27600
agtttcctcc tgttcctgtc catccgcacc cactatcttc atgttgttgc agatgaagcg   27660
```

```
cgcaagaccg tctgaagata ccttcaaccc cgtgtatcca tatgacacgg aaaccggtcc    27720
tccaactgtg cctttctta ctcctcccct tgtatccccc aatgggtttc aagagagtcc     27780
ccctggggta ctctctttgc gcctatccga acctctagtt acctccaatg gcatgcttgc    27840
gctcaaaatg ggcaacggcc tctctctgga cgaggccggc aaccttacct cccaaaatgt    27900
aaccactgtg agcccacctc tcaaaaaaac caagtcaaac ataaacctgg aaatatctgc    27960 accccctcaca gttacctcag aagccctaac tgtggctgcc gccgcacctc taatggtcgc    28020
gggcaacaca ctcaccatgc aatcacaggc cccgctaacc gtgcacgact ccaaacttag    28080
cattgccacc caaggacccc tcacagtgtc agaaggaaag ctagccctgc aaacatcagg    28140
ccccctcacc accaccgata gcagtaccct tactatcact gcctcacccc ctctaactac    28200
tgccactggt agcttgggca ttgacttgaa agagcccatt tatacacaaa atggaaaact    28260
aggactaaag tacggggctc ctttgcatgt aacagacgac ctaaacactt tgaccgtagc    28320
aactggtcca ggtgtgacta ttaataatac ttccttgcaa actaaagtta ctggagcctt    28380
gggttttgat tcacaaggca atatgcaact taatgtagca ggaggactaa ggattgattc    28440
tcaaaacaga cgccttatac ttgatgttag ttatccgttt gatgctcaaa accaactaaa    28500
tctaagacta ggacagggcc ctctttttat aaactcagcc cacaacttgg atattaacta    28560
caacaaaggc ctttacttgt ttacagcttc aaacaattcc aaaaagcttg aggttaacct    28620
aagcactgcc aaggggttga tgtttgacgc tacagccata gccattaatg caggagatgg    28680
gcttgaattt ggttcaccta atgcaccaaa cacaaatccc ctcaaaacaa aaattggcca    28740
tggcctagaa tttgattcaa acaaggctat ggttcctaaa ctaggaactg ccttagttt     28800 tgacagcaca ggtgccatta cagtaggaaa caaaaataat gataagctaa ctttgtggac    28860
cacaccagct ccatctccta actgtagact aaatgcagag aaagatgcta aactcacttt    28920
ggtcttaaca aaatgtggca gtcaaatact tgctacagtt tcagttttgg ctgttaaagg    28980
cagtttggct ccaatatctg gaacagttca aagtgctcat cttattataa gatttgacga    29040
aaatggagtg ctactaaaca attccttcct ggacccagaa tattggaact ttagaaatgg    29100
agatcttact gaaggcacag cctatacaaa cgctgttgga tttatgccta acctatcagc    29160
ttatccaaaa tctcacggta aaactgccaa aagtaacatt gtcagtcaag tttacttaaa    29220
cggagacaaa actaaacctg taacactaac cattacacta aacggtacac aggaaacagg    29280
agacacaact ccaagtgcat actctatgtc attttcatgg gactggtctg cccacaacta    29340
cattaatgaa atatttgcca catcctctta cactttttca tacattgccc aagaataaag    29400
aatcgtttgt gttatgtttc aacgtgttta tttttcaatt gcagaaaatt tcaagtcatt    29460
tttcattcag tagtatagcc ccaccaccac atagcttata cagatcaccg taccttaatc    29520
aaactcacag aaccctagta ttcaacctgc cacctccctc ccaacacaca gagtacacag    29580
tcctttctcc ccggctggcc ttaaaaagca tcatatcatg ggtaacagac atattcttag    29640
gtgttatatt ccacacggtt tcctgtcgag ccaaacgctc atcagtgata ttaataaact    29700 cccccgggcag ctcacttaag ttcatgtcgc tgtccagctg ctgagccaca ggctgctgtc    29760
caacttgcgg ttgcttaacg ggcggcgaag gagaagtcca cgcctacatg ggggtagagt    29820
cataatcgtg catcaggata gggcggtggt gctgcagcag cgcgcgaata aactgctgcc    29880
gccgccgctc cgtcctgcag gaatacaaca tggcagtggt ctcctcagcg atgattcgca    29940
ccgcccgcag cataaggcgc cttgtcctcc gggcacagca gcgcaccctg atctcactta    30000
aatcagcaca gtaactgcag cacagcacca caatattgtt caaaatccca cagtgcaagg    30060
```

-continued

```
cgctgtatcc aaagctcatg gcggggacca cagaacccac gtggccatca taccacaagc    30120
gcaggtagat taagtggcga ccccctcataa acacgctgga cataaacatt acctctttg    30180 gcatgttgta attcaccacc tcccggtacc atataaacct ctgattaaac atggcgccat    30240
ccaccaccat cctaaaccag ctggccaaaa cctgcccgcc ggctatacac tgcagggaac    30300
cgggactgga acaatgacag tggagagccc aggactcgta accatggatc atcatgctcg    30360
tcatgatatc aatgttggca caacacaggc acacgtgcat acacttcctc aggattacaa    30420
gctcctcccg cgttagaacc atatcccagg gaacaaccca ttcctgaatc agcgtaaatc    30480
ccacactgca gggaagacct cgcacgtaac tcacgttgtg cattgtcaaa gtgttacatt    30540
cgggcagcag cggatgatcc tccagtatgg tagcgcgggt ttctgtctca aaaggaggta    30600
gacgatccct actgtacgga gtgcgccgag acaaccgaga tcgtgttggt cgtagtgtca    30660
tgccaaatgg aacgccggac gtagtcatat ttcctgaagc aaaaccaggt gcgggcgtga    30720
caaacagatc tgcgtctccg gtctcgccgc ttagatcgct ctgtgtagta gttgtagtat    30780
atccactctc tcaaagcatc caggcgcccc ctggcttcgg gttctatgta aactccttca    30840
tgcgccgctg ccctgataac atccaccacc gcagaataag ccacacccag ccaacctaca    30900
cattcgttct gcgagtcaca cacgggagga gcgggaagag ctggaagaac catgttttt    30960 tttttattcc aaaagattat ccaaaacctc aaaatgaaga tctattaagt gaacgcgctc    31020
ccctccggtg gcgtggtcaa actctacagc caaagaacag ataatggcat tgtaagatg     31080 ttgcacaatg gcttccaaaa ggcaaacggc cctcacgtcc aagtggacgt aaaggctaaa    31140
cccttcaggg tgaatctcct ctataaacat tccagcacct tcaaccatgc ccaaataatt    31200
ctcatctcgc caccttctca atatatctct aagcaaatcc cgaatattaa gtccggccat    31260
tgtaaaaatc tgctccagag cgccctccac cttcagcctc aagcagcgaa tcatgattgc    31320
aaaaattcag gttcctcaca gacctgtata agattcaaaa gcggaacatt aacaaaaata    31380
ccgcgatccc gtaggtccct tcgcagggcc agctgaacat aatcgtgcag gtctgcacgg    31440
accagcgcgg ccacttcccc gccaggaacc atgacaaaag aacccacact gattatgaca    31500
cgcatactcg gagctatgct aaccagcgta gccccgatgt aagcttgttg catgggcggc    31560
gatataaaat gcaaggtgct gctcaaaaaa tcaggcaaag cctcgcgcaa aaagaaagc    31620 acatcgtagt catgctcatg cagataaagg caggtaagct ccggaaccac cacagaaaaa    31680
gacaccattt ttctctcaaa catgtctgcg ggtttctgca taaacacaaa ataaaataac    31740
aaaaaaacat ttaaacatta gaagcctgtc ttacaacagg aaaaacaacc cttataagca    31800
taagacggac tacggccatg ccggcgtgac cgtaaaaaaa ctggtcaccg tgattaaaaa    31860
gcaccaccga cagctcctcg gtcatgtccg gagtcataat gtaagactcg gtaaacacat    31920
caggttgatt cacatcggtc agtgctaaaa agcgaccgaa atagcccggg ggaatacata    31980
cccgcaggcg tagagacaac attacagccc ccataggagg tataacaaaa ttaataggag    32040
agaaaaacac ataaacacct gaaaaaccct cctgcctagg caaaatagca ccctcccgct    32100
ccagaacaac atacagcgct tccacagcgg cagccataac agtcagcctt accagtaaaa    32160
aagaaaacct attaaaaaaa caccactcga cacggcacca gctcaatcag tcacagtgta    32220 aaaagggcc aagtgcagag cgagtatata taggactaaa aaatgacgta acggttaaag    32280
tccacaaaaa acaccagaa aaccgcacgc gaacctacgc ccagaaacga aagccaaaaa    32340
acccacaact tcctcaaatc gtcacttccg ttttcccacg ttacgtcact tcccatttta    32400
agaaaactac aattcccaac acatacaagt tactccgccc taaaacctac gtcacccgcc    32460
```

```
ccgttcccac gccccgcgcc acgtcacaaa ctccaccccc tcattatcat attggcttca    32520
atccaaaata aggtatatta ttgatgatgt taat                               32554
```